(12) United States Patent
Fidalgo et al.

(10) Patent No.: US 8,026,253 B2
(45) Date of Patent: Sep. 27, 2011

(54) QUINOLINE INHIBITORS OF HCV POLYMERASE

(75) Inventors: Javier de Vicente Fidalgo, Glen Ridge, NJ (US); Jim Li, San Francisco, CA (US); Ryan Craig Schoenfeld, San Jose, CA (US); Francisco Xavier Talamas, Mountain View, CA (US); Joshua Paul Gergely Taygerly, San Francisco, CA (US)

(73) Assignee: Roche Palo Alto LLC, South San Francico, CA (US)

( * ) Notice: Subject to any disclaimer, the term of this patent is extended or adjusted under 35 U.S.C. 154(b) by 0 days.

(21) Appl. No.: 12/797,308

(22) Filed: Jun. 9, 2010

(65) Prior Publication Data
US 2010/0311760 A1 Dec. 9, 2010

Related U.S. Application Data

(60) Provisional application No. 61/185,460, filed on Jun. 9, 2009, provisional application No. 61/263,351, filed on Nov. 21, 2009.

(51) Int. Cl.
*A61K 31/47* (2006.01)

(52) U.S. Cl. ........ 514/314; 544/128; 544/333; 546/167; 546/208; 546/268.1; 548/266.4; 548/518; 548/950

(58) Field of Classification Search ............ 514/314; 544/128, 333; 546/167, 208, 268.1; 548/266.4, 548/518, 950
See application file for complete search history.

(56) References Cited

FOREIGN PATENT DOCUMENTS

| GB | 558009 | * | 12/1943 |
|---|---|---|---|
| WO | 0009543 A2 | | 2/2000 |
| WO | 0185172 A1 | | 11/2001 |
| WO | 2009032116 A1 | | 3/2009 |
| WO | 2009032123 A2 | | 3/2009 |
| WO | 2009032125 A1 | | 3/2009 |
| WO | 2009039127 A1 | | 3/2009 |
| WO | 2009039134 A1 | | 3/2009 |
| WO | WO2009/039135 A1 | | 3/2009 |
| WO | 2009064848 A1 | | 5/2009 |
| WO | 2009064852 A1 | | 5/2009 |
| WO | WO2010/111436 A2 | | 9/2010 |
| WO | WO2010/111437 A1 | | 9/2010 |

* cited by examiner

*Primary Examiner* — James O Wilson
*Assistant Examiner* — Douglas M Willis
(74) *Attorney, Agent, or Firm* — Brian L. Buckwalter

(57) ABSTRACT

Compounds having the formula I wherein

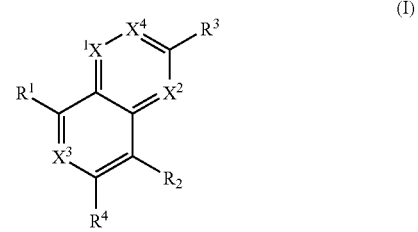

wherein $R^1$, $R^2$, $R^3$, $R^4$, $X^1$, $X^2$, $X^3$ and $X^4$ and as defined herein are Hepatitis C virus NS5b polymerase inhibitors. Also disclosed are compositions and methods for treating an HCV infection and inhibiting HCV replication.

13 Claims, No Drawings

QUINOLINE INHIBITORS OF HCV POLYMERASE

CROSS-REFERENCE TO PRIOR APPLICATIONS

This application claims the benefit of priority to U.S. Ser. No. 61/185,460 filed Jun. 9, 2009 and to U.S. Ser. No. 61/263,351 filed Nov. 21, 2009 both of which are hereby incorporated by reference in their entirety.

FIELD OF THE INVENTION

The present invention provides non-nucleoside compounds of formula I, and certain derivatives thereof, which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., *Flaviviridae*: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forms and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.,* 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.,* 1999 19:5; Di Besceglie, A. M. and Bacon, B. R., *Scientific American,* October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investing. Drugs* 2003 12(8): 1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.—Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGA-SYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release* 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase. The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up by the cell in vivo and be converted in vivo to its triphosphate form to compete as a substrate at the polymerase nucleotide binding site. This conversion to the triphosphate is commonly mediated by cellular kinases which impart additional structural limitations on any nucleoside. In addition this requirement for phosphorylation limits the direct evaluation of nucleosides as inhibitors of HCV replication to cell-based assays (J. A. Martin et al., U.S. Pat. No. 6,846,810; C. Pierra et al., *J. Med. Chem.* 2006 49(22):6614-6620; J. W. Tomassini et al., *Antimicrob. Agents and Chemother.* 2005 49(5):2050; J. L. Clark et al., *J. Med. Chem.* 2005 48(17):2005).

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

Other interferons currently in development include albinterferon-α-2b (Albuferon), IFN-omega with DUROS, LOCTERON™ and interferon-α-2b XL. As these and other interferons reach the marketplace their use in combination therapy with compounds of the present invention is anticipated.

HCV polymerase inhibitors are another target for drug discovery and compounds in development include R-1626, R-7128, IDX184/IDX102, PF-868554 (Pfizer), VCH-759 (ViroChem), GS-9190 (Gilead), A-837093 and A-848837 (Abbot), MK-3281 (Merck), GSK949614 and GSK625433 (Glaxo), ANA598 (Anadys), VBY 708 (ViroBay).

Inhibitors of the HCV NS3 protease also have been identified as potentially useful for treatment of HCV. Protease inhibitors in clinical trials include VX-950 (Telaprevir, Vertex), SCH503034 (Broceprevir, Schering), TMC435350 (Tibotec/Medivir) and ITMN-191 (Intermune). Other protease inhibitors in earlier stages of development include MK7009 (Merck), BMS-790052 (Bristol Myers Squibb), VBY-376 (Virobay), IDXSCA/IDXSCB (Idenix), BI12202 (Boehringer), VX-500 (Vertex), PHX1766 Phenomix).

Other targets for anti-HCV therapy under investigation include cyclophilin inhibitors which inhibit RNA binding to NS5b, nitazoxanide, Celgosivir (Migenix), an inhibitor of α-glucosidase-1, caspase inhibitors, Toll-like receptor agonists and immunostimulants such as Zadaxin (SciClone).

SUMMARY OF THE INVENTION

There is currently no preventive treatment of Hepatitis C virus (HCV) and currently approved therapies, which exist only against HCV, are limited. Design and development of new pharmaceutical compounds is essential. In one aspect of the present invention there is provided a compound according to formula I wherein:

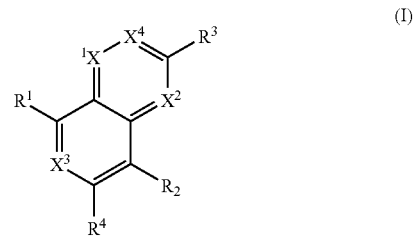

$X^1$ is N and $X^2$, $X^3$ and $X^4$ are $CR^5$; or
$X^1$ and $X^2$ are N, and $X^3$ and $X^4$ are $CR^5$; or
$X^1$, $X^2$ and $X^4$ are $CR^5$ and $X^3$ is N; or
$X^2$ and $X^4$ are N and $X^2$ and $X^3$ are $CR^5$; or
$X^1$, $X^2$, $X^3$ and $X^4$ are $CR^5$.

$R^1$ is (a) a heteroaryl radical selected from the group consisting of pyridinyl, 2-oxo-1,2-dihydro-pyridin-3-yl, 3-oxo-3,4-dihydro-pyrazin-2-yl, 3-oxo-2,3-dihydro-pyridazin-4-yl, 2-oxo-1,2-dihydro-pyrimidin-4-one-5-yl, 6-oxo-1,6-dihydro-[1,2,4]triazin-5-yl, 2,4-dioxo-3,4-dihydro-2H-pyrimidin-1-yl, 2-oxo-2(H)-pyridin-1-yl, 6-oxo-6H-pyridazin-1-yl, 6-oxo-6H-pyrimidin-1-yl and 2-oxo-2H-pyrazin-1-yl said heteroaryl being optionally substituted by halogen, $C_{1-6}$ alkyl, $C_{1-3}$ haloalkyl, $C_{1-6}$ hydroxyalkyl, $C_{1-3}$ alkoxy-$C_{1-3}$ alkyl, $C_{1-6}$ alkoxy, $X^1(CH_2)_{1-6}CO_2H$ or (h) $X^1$—$(CH_2)_{2-6}$ $NR^gR^h$ or; (b) a heterocyclic radical selected from the group consisting of 2-oxo-tetrahydro-pyrimidin-1-yl, 2-oxo-imidazolidin-1-yl, 2-oxo-piperidin-1-yl, 2-oxo-pyrrolidin-1-yl, 2,6-dioxo-tetrahydro-pyrimidin-1-yl, 2,4-dioxo-1,2,3,4-tetrahydro-pyrimidin-5-yl and 2,5-dioxo-imidazolidin-1-yl and 2,4-dioxo-tetrahydro-pyrimidin-1-yl.

$R^2$ is hydrogen, $C_{1-6}$ alkoxy, $C_{1-6}$ alkyl, $C_{1-6}$ haloalkyl, $C_{1-6}$ haloalkoxy or halogen.

$R^3$ is (a) aryl, (b) heteroaryl, (c) $NR^aR^b$, (d) hydrogen, (e) halogen wherein said aryl or said heteroaryl are optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_nNR^cR^d$, cyano, $C_{1-6}$ alkoxycarbonyl, carbamoyl, N-alkylcarbamoyl, N,N-dialkylcarbamoyl, $(CH_2)_{0-3}CO_2H$, $SO_2NH_2$, $C_{1-6}$ alkylsulfinyl and $C_{1-6}$ alkylsulfonyl or (f) —X($R^7$)[C($R^6$)$_{2-6}$NR$^e$R$^f$ wherein X is O or NR$^7$, R$^7$ is hydrogen or $C_{2-4}$ alkyl, $R^6$ is independently in each occurrence hydrogen, $C_{1-3}$ alkyl or two $R^6$ residues on the same carbon are $C_{2-5}$ alkylene or two $R^6$ residues on different carbons are $C_{1-4}$ alkylene.

$R^a$ and $R^b$ along with the nitrogen to which they are attached are a cyclic amine independently substituted by one to three groups independently selected from $C_{1-6}$ alkyl, halogen or $(CH_2)_nNR^eR^f$.

$R^c$ and $R^d$ are independently hydrogen, $C_{1-6}$ alkyl, $C_{1-6}$ haloalkyl, $C_{1-6}$ acyl, $SO_2R^8$ wherein $R^8$ is (a) $C_{1-6}$ alkyl, (b) $C_{1-6}$ haloalkyl, (c) $C_{3-7}$ cycloalkyl, (d) $C_{3-7}$ cycloalkyl-$C_{1-3}$ alkyl, (e) $C_{1-6}$ alkoxy-$C_{1-6}$ alkyl or (f) $SO_2[C(R^9)_2]_{0-6}NR^kR^l$, $C_{1-3}$ alkylcarbamoyl or $C_{1-3}$ dialkylcarbamoyl.

$R^e$ and $R^f$, are independently hydrogen, $C_{1-6}$ alkyl, $C_{1-6}$ haloalkyl, $C_{1-6}$ acyl, $SO_2R^8$ wherein $R^8$ is (a) $C_{1-6}$ alkyl, (b) $C_{1-6}$ haloalkyl, (c) $C_{3-7}$ cycloalkyl, (d) $C_{3-7}$ cycloalkyl-$C_{1-3}$ alkyl, (e) $C_{1-6}$ alkoxy-$C_{1-6}$ alkyl or (f) $SO_2[C(R^9)_2]_{0-6}NR^kR^l$.

$R^i$ and $R^j$ are (i) independently hydrogen, $C_{1-3}$ alkyl or $(CH_2)_{2-6}NR^gR^h$ or (ii) together with the nitrogen to which they are attached are $(CH_2)_2X^5(CH_2)_2$ wherein $X^5$ is O or $NR^k$ and $R^k$ is hydrogen, $C_{1-3}$ alkyl, $C_{1-3}$ acyl or $C_{1-3}$ alkylsulfonyl.

$R^4$ is hydrogen, $CF_3$, $CH_2CF_3$, $C_{3-5}$ cycloalkyl, halogen, $C_{1-6}$ alkoxy, $C_{1-3}$ haloalkoxy, $CHR^{4a}R^{4b}$ or $CR^{4a}R^{4b}R^{4c}$ wherein (i) $R^{4a}$, $R^{4b}$ and $R^{4c}$ are independently selected from $C_{1-3}$ alkyl, $CD_3$, $C_{1-2}$ alkoxy, $C_{1-2}$ fluoroalkyl, $C_{1-3}$ hydroxyalkyl, cyano or hydroxy; or, (ii) when taken together, $R^{4a}$ and $R^{4b}$ together are $C_{2-4}$ alkylene and $R^{4c}$ is hydrogen, $C_{1-3}$ alkyl, $C_{1-2}$ alkoxy, halogen, $C_{1-3}$ hydroxyalkyl, cyano or $C_{1-2}$ fluoroalkyl or $R^{4a}$ and $R^{4b}$ together with the carbon to which they are attached are 3-oxetanyl, or tetrahydrofuran-2-yl.

$R^5$ is independently in each occurrence hydrogen, halogen, $C_{1-6}$ alkoxy, or $C_{1-6}$ alkyl.

$R^8$, $R^g$ and $R^h$ are independently in each occurrence hydrogen or $C_{1-3}$ alkyl.

$R^k$ and $R^l$ are (i) independently in each occurrence hydrogen or $C_{1-6}$ alkyl or (ii) together with the nitrogen to which they are attached $R^k$ and $R^l$ form a cyclic amine.

n is independently in each occurrence zero to three.

Compounds of general formula I can be either neutral compounds or a pharmaceutically acceptable salt thereof.

The present invention also provides a method for treating a disease a Hepatitis C Virus (HCV) virus infection by administering a therapeutically effective quantity of a compound according to formula I to a patient in need thereof. The compound can be administered alone or co-administered with other antiviral compounds or immunomodulators.

The present invention also provides a method for inhibiting replication of HCV in a cell by administering a compound according to formula I in an amount effective to inhibit HCV.

The present invention also provides a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least".

When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such combinations result in stable compounds.

The symbols "*" at the end of a bond or "- - - -" drawn through a bond each refer to the point of attachment of a functional group or other chemical moiety to the rest of the molecule of which it is a part. Thus, for example:

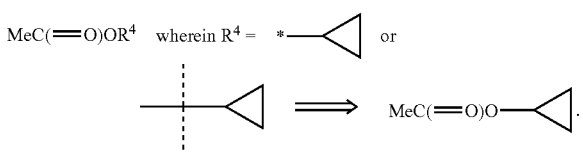

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formulae I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, .alpha.-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxiliary) to produce diastereomers which can be separated by chromatography or by fractional crystallization after which time the chiral auxiliary is chemically removed to afford the pure enantiomers.

The compounds of formula I may contain a basic center and suitable acid addition salts are formed from acids which form non-toxic salts. Examples of salts of inorganic acids include the hydrochloride, hydrobromide, hydroiodide, chloride, bromide, iodide, sulfate, bisulfate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

The term "isotopologue" has been used to distinguish species that differ only in the isotopic composition thereof (IUPAC Compendium of Chemical Terminology $2^{nd}$ Edition 1997). Isotopologues can differ in the level of isotopic enrichment at one or more positions and/or in the positions(s) of isotopic enrichment.

Variations from the natural isotopic abundance can occur in a synthesized compound depending upon the source of chemical precursors used in the synthesis and form isotope exchange during the synthesis. Thus isotopic enrichment factor of each deuterium present at a site designated as a site of deuteration is independent of deuteration at other sites and some variation in the deuterium content at other then the designated sites may occur and these variations can result in the formation of isotopologues are within the scope of the compounds claimed. Deuterium enrichment factor at sites not designated as deuterium or "D" will be less than 49.5% and typically significantly less than 49.5% and more commonly less than 20%

Since the natural abundance of deuterium is 0.015%, these variations from the naturally observed levels of deuterium will not have a material effect on observed biological properties of the compounds.

Unless otherwise stated, when a position is explicitly or implicitly designated as "H" or "hydrogen", the isotope ratio is presumed to have hydrogen at its natural abundance isotopic composition with the provision that some adventitious variations can result from the synthetic processes.

The term "isotopic enrichment factor" as used herein means the ratio between the isotopic abundance of D at a specified position in a compound of this invention and the naturally occurring abundance of that isotope. In one embodiment of the present invention there is provided a compound according to formula I wherein the isotopic enrichment factor of the tert-butyl moiety is at least 3300 (49.5%). To avoid any ambiguity, the isotopic enrichment factor for the tert-butyl refers to the aggregate of the three methyl groups and the methyl groups are not assessed independently.

In other embodiments, there is provided a compound according to formula I with an isotopic enrichment factor for each deuterium present at a site designated as a potential site of deuteration on the compound of at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

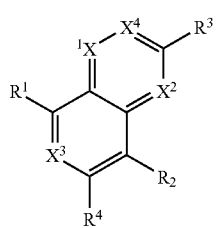

(I)

In one embodiment of the present invention there is provided a compound according to formula I wherein $R^1$, $R^2$, $R^3$, $R^4$, $X^1$, $X^2$, $X^3$ and $X^4$ are as defined herein above.

In an embodiment of the present invention there is provided a compound according to formula I wherein $X^1$ is N and $X^2$, $X^3$ and $X^4$ are $CR^5$; or $X^1$ and $X^2$ are N, and $X^3$ and $X^4$ are $CR^5$; or $X^1$, $X^2$ and $X^4$ are $CR^5$ and $X^3$ is N; or $X^1$ and $X^4$ are N and $X^2$ and $X^3$ are $CR^5$; or $X^1$, $X^2$, $X^3$ and $X^4$ are $CR^5$; $R^1$ is (a) a heteroaryl radical selected from the group consisting of pyridinyl, 2-oxo-1,2-dihydro-pyridin-3-yl, 3-oxo-3,4-dihydro-pyrazin-2-yl, 3-oxo-2,3-dihydro-pyridazin-4-yl, 2-oxo-1,2-dihydro-pyrimidin-4-one-5-yl, 6-oxo-1,6-dihydro-[1,2,4]triazin-5-yl, 2,4-dioxo-1,2,3,4-tetrahydro-pyrimidin-5-yl, 2,4-dioxo-3,4-dihydro-2H-pyrimidin-1-yl, 2-oxo-2 (H)-pyridin-1-yl, 6-oxo-6H-pyridazin-1-yl, 6-oxo-6H-pyrimidin-1-yl; 2-oxo-2H-pyrazin-1-yl said heteroaryl being optionally substituted by halogen, $C_{1-6}$ alkyl, $C_{1-3}$ haloalkyl, $C_{1-6}$ alkoxy, X—$(CH_2)_{1-6}CO_2H$ or X—$(CH_2)_{2-6}NR^gR^h$ or; (b) a heterocyclic radical selected from the group consisting of 2-oxo-tetrahydro-pyrimidin-1-yl, 2-oxo-imidazolidin-1-yl, 2-oxo-piperidin-1-yl, 2-oxo-pyrrolidin-1-yl, 2,6-dioxo-tetrahydro-pyrimidin-1-yl and 2,5-dioxo-imidazolidin-1-yl; $R^2$ is hydrogen, $C_{1-6}$ alkoxy, $C_{1-6}$ alkyl, $C_{1-6}$ haloalkyl, $C_{1-6}$ haloalkoxy or halogen; $R^3$ is (a) aryl, (b) heteroaryl, (c) $NR^aR^b$, (d) hydrogen, (e) halogen wherein said aryl or said heteroaryl are optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_nNR^cR^d$, cyano, $C_{1-6}$ alkoxycarbonyl, carbamoyl, N-alkylcarbamoyl, N,N-dialkylcarbamoyl, $(CH_2)_nCO_2H$, $SO_2NH_2$, $C_{1-6}$ alkylsulfinyl and $C_{1-6}$ alkylsulfonyl, or (f) —X($R^g$)[C($R^6$)]$_p$NR$^e$R$^f$ wherein $R^6$ is independently in each occurrence hydrogen, $C_{1-3}$ alkyl or two $R^6$ residues on the same carbon are $C_{2-5}$ alkylene or two $R^6$ residues on different carbons are $C_{1-4}$ alkylene; $R^a$ and $R^b$ along with the nitrogen to which they are attached are a cyclic amine independently substituted by, $C_{1-6}$ alkyl, halogen or $(CH_2)_nNR^eR^f$; $R^c$ and $R^d$ are independently hydrogen, $C_{1-6}$ alkyl, $C_{1-6}$ haloalkyl, $C_{1-6}$ acyl, $C_{1-6}$ sulfonyl, $C_{1-6}$ haloalkylsulfonyl, $C_{3-7}$ cycloalkyl-sulfonyl, $C_{3-7}$ cycloalkyl-$C_{1-3}$ alkylsulfonyl, $C_{1-6}$ alkoxy-$C_{1-6}$ alkylsulfonyl, —SO$_2$—NR$^i$R$^j$, $C_{1-3}$ alkylcarbamoyl or $C_{1-3}$ dialkylcarbamoyl; $R^e$ and $R^f$ are independently hydrogen, $C_{1-6}$ alkyl, $C_{1-6}$ halo alkyl, $C_{1-6}$ acyl, $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl, $C_{1-6}$ alkoxy-$C_{1-6}$ alkylsulfonyl, —SO$_2$—NR$^i$R$^j$; $R^i$ and $R^j$ are (i) independently hydrogen, $C_{1-3}$ alkyl or $(CH_2)_{2-6}NR^gR^h$ or (ii) together with the nitrogen to which they are attached are $(CH_2)_2X^5(CH_2)_2$ wherein $X^5$ is O or $NR^k$ and $R^k$ is hydrogen, $C_{1-3}$ alkyl, $C_{1-3}$ acyl or $C_{1-3}$ alkylsulfonyl; $R^g$ and $R^h$ are independently in each occurrence hydrogen or $C_{1-3}$ alkyl; $R^4$ is hydrogen, $C_{1-6}$ alkyl, $C_{1-6}$ halo alkyl, $C_{3-5}$ cycloalkyl, halogen, $C_{1-6}$ alkoxy, $C_{1-3}$ haloalkoxy or $CR^{4a}R^{4b}R^{4c}$ wherein: (i) $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxy; or (ii) when taken together, $R^{4a}$ and $R^{4b}$ together are $C_{2-4}$ alkylene and $R^{4c}$ is hydrogen, $C_{1-3}$ alkyl, $C_{1-2}$ alkoxy, halogen, $C_{1-3}$ hydroxyalkyl, cyano or $C_{1-2}$ fluoroalkyl or $R^{4a}$ and $R^{4b}$ together with the carbon to which they are attached are 3-oxetanyl, or tetrahydrofuran-2-yl; $R^5$ is independently in each occurrence hydrogen, halogen$C_{1-6}$ alkoxy, or $C_{1-6}$ alkyl; X is independently in each occurrence O or $NR^g$; n is independently in each occurrence zero to three; or a pharmaceutically acceptable salt thereof.

In another embodiment of the present invention there is provided a compound according to formula wherein $X^1$ is N and $X^2$, $X^3$ and $X^4$ are $CR^5$ or $X^1$ and $X^2$ are N, and $X^3$ and $X^4$ are $CR^5$. $R^1$ is a heteroaryl radical selected from the group consisting of pyridinyl, 2-oxo-1,2-dihydro-pyridin-3-yl, 2,4-dioxo-1,2,3,4-tetrahydro-pyrimidin-5-yl and 2,4-dioxo-3,4-dihydro-2H-pyrimidin-1-yl said heteroaryl being optionally substituted by halogen, $C_{1-6}$ alkyl, or $C_{1-6}$ alkoxy. $R^2$ is hydrogen or $C_{1-6}$ alkoxy or $R^1$ is 2-oxo-tetrahydro-pyrimidin-1-yl. $R^3$ is aryl, $NR^aR^b$, hydrogen or halogen wherein said aryl is optionally independently substituted with one to three substitutents selected from the group consisting of halogen, $(CH_2)_nNR^cR^d$, wherein n is one. $R^a$ and $R^b$ along with the nitrogen to which they are attached are a cyclic amine optionally substituted by one to three groups independently selected from $(CH_2)_nNR^eR^f$ wherein n is zero to two, $C_{1-6}$ alkyl or halogen. $R^e$ is hydrogen and $R^f$ is $C_{1-6}$ sulfonyl. $R^c$ is hydrogen and $R^d$ is $C_{1-6}$ sulfonyl. $R^4$ is trifluoromethyl, 3,3,3-trifluoroethyl or $CR^{4a}R^{4b}R^{4c}$ wherein $R^{4a}$, $R^{4b}$ and $R^{4c}$ are $CH_3$ or $CD_3$. $R^5$ is independently in each occurrence hydrogen, halogen, $C_{1-6}$ alkoxy, or $C_{1-6}$ alkyl. This embodiment includes a pharmaceutically acceptable salt of a compound included herein In an embodiment of the invention there is provided a compound according to formula I wherein $R^3$ is (a) aryl or (b) heteroaryl wherein said aryl or said heteroaryl are optionally independently substituted with one to three substitutents selected from the group consisting of hydroxy, $C_{1-6}$ alkoxy, $C_{1-6}$ alkyl, $C_{1-6}$ hydroxyalkyl, halogen, cyano, $C_{1-6}$ alkoxycarbonyl, carbamoyl, N-alkylcarbamoyl, N,N-dialkylcarbamoyl, carboxyl, $SO_2NH_2$, $C_{1-6}$ alkylsulfinyl and $C_{1-6}$ alkylsulfonyl wherein n is zero to three.

In another embodiment of the present invention there is provided a compound according to formula I wherein $X^1$ is N and $X^2$, $X^3$ and $X^4$ are $CR^5$; $R^3$ is (a) phenyl substituted at least by $(CH_2)_nNR^cR^d$ at the 4-position wherein n is zero or (b) $NR^aR^b$. The phrase "phenyl substituted at least by $(CH_2)_n$ $NR^cR^d$ at the 4-position refers to (i) wherein unsubstituted positions can be further optionally substituted. The phrase" phenyl substituted at least by $(CH_2)_nNR^cR^d$ at the 4-position refers to (i) wherein unsubstituted positions can be further optionally substituted.

In another embodiment of the present invention there is provided a compound according to formula I wherein $R^1$ is 2-oxo-1,2-dihydro-pyridin-3-yl or 2,4-dioxo-3,4-dihydro-2H-pyrimidin-1-yl or 2,4-dioxo-1,2,3,4-tetrahydro-pyrimidin-5-yl optionally substituted by halogen, $C_{1-6}$ alkyl, $C_{1-3}$ haloalkyl or $C_{1-6}$ alkoxy; $X^1$ is N and $X^2$, $X^3$ and $X^4$ are $CR^5$ and $R^3$ is phenyl substituted at least by $(CH_2)_nNR^cR^d$ at the 4-position wherein n is zero.

In another embodiment of the present invention there is provided a compound according to formula I wherein $R^1$ is 2-oxo-1,2-dihydro-pyridin-3-yl, 2,4-dioxo-3,4-dihydro-2H-pyrimidin-1-y or 2,4-dioxo-1,2,3,4-tetrahydro-pyrimidin-5-yl optionally substituted by halogen, $C_{1-6}$ alkyl, $C_{1-3}$ haloalkyl or $C_{1-6}$ alkoxy; $X^1$ is N and $X^2$, $X^3$ and $X^4$ are $CR^5$; $R^3$ is phenyl substituted at least by $(CH_2)_nNR^cR^d$ at the 4-position wherein n is zero and $R^4$ is $CR^{4a}R^{4b}R^{4c}$ wherein (a) $R^{4a}$, $R^{4b}$ and $R^{4c}$ are $CH_3$, $CD_3$ or fluorine or $R^{4a}$ and $R^{4b}$ together are $C_2$ alkylene and (b) $R^{4c}$ is $C_{1-3}$ alkyl, $C_{1-2}$ alkoxy, halogen, $C_{1-3}$ hydroxyalkyl, cyano or $C_{1-2}$ fluoroalkyl.

In another embodiment of the present invention there is provided a compound according to formula I wherein $R^1$ is 2-oxo-1,2-dihydro-pyridin-3-yl, 2,4-dioxo-3,4-dihydro-2H-pyrimidin-1-y or 2,4-dioxo-1,2,3,4-tetrahydro-pyrimidin-5-yl optionally substituted by halogen, $C_{1-6}$ alkyl, $C_{1-3}$ haloalkyl or $C_{1-6}$ alkoxy; $X^1$ is N and $X^2$, $X^3$ and $X^4$ are $CR^5$; $R^3$ is $NR^aR^b$; and $R^4$ is $CR^{4a}R^{4b}R^{4c}$ wherein (a) $R^{4a}$, $R^{4b}$ and $R^{4c}$ are $CH_3$, $CD_3$ or fluorine or $R^{4a}$ and $R^{4b}$ together are $C_2$ alkylene and (b) $R^{4c}$ is $C_{1-3}$ alkyl, $C_{1-2}$ alkoxy, halogen, $C_{1-3}$ hydroxyalkyl, cyano or $C_{1-2}$ fluoroalkyl.

In another embodiment of the present invention there is provided a compound according to formula I wherein $R^1$ is 2-oxo-1,2-dihydro-pyridin-3-yl, 2,4-dioxo-3,4-dihydro-2H-pyrimidin-1-y or 2,4-dioxo-1,2,3,4-tetrahydro-pyrimidin-5-yl optionally substituted by halogen, $C_{1-6}$ alkyl, $C_{1-3}$ haloalkyl or $C_{1-6}$ alkoxy; $X^1$ is N and $X^2$, $X^3$ and $X^4$ are $CR^5$; $R^3$ is $NR^aR^b$; wherein $NR^aR^b$ together is cyclic amine substituted by $(CH_2)_nNR^eR^f$ wherein n is zero to two; and $R^e$ and $R^f$ are independently hydrogen, $C_{1-6}$ alkyl, $C_{1-6}$ haloalkyl, $SO_2R^8$ wherein $R^8$ is (a) $C_{1-6}$ alkyl, (b) $C_{1-6}$ haloalkyl, (c) $C_{3-7}$ cycloalkyl, (d) $C_{3-7}$ cycloalkyl-$C_{1-3}$ alkyl, (e) $C_{1-6}$ alkoxy-$C_{1-6}$ alkyl and $R^4$ is $CR^{4a}R^{4b}R^{4c}$ and (a) $R^{4a}$, $R^{4b}$ and $R^{4c}$ are $CH_3$, $CD_3$ or fluorine or $R^{4a}$ and $R^{4b}$ together are $C_2$ alkylene and (b) $R^{4c}$ is $C_{1-3}$ alkyl, $C_{1-2}$ alkoxy, halogen, $C_{1-3}$ hydroxyalkyl, cyano or $C_{1-2}$ fluoroalkyl.

In another embodiment of the present invention there is provided a compound according to formula I wherein $R^1$ is 6-oxo-1,6-dihydro-[1,2,4]triazin-5-yl; $X^1$ is N and $X^2$, $X^3$ and $X^4$ are $CR^5$ and $R^3$ is phenyl substituted at least by $(CH_2)_n NR^cR^d$ at the 4-position wherein n is zero.

In another embodiment of the present invention there is provided a compound according to formula I wherein $R^1$ is 2-oxo-tetrahydro-pyrimidin-1-yl; $X^1$ is N and $X^2$, $X^3$ and $X^4$ are $CR^5$ and $R^3$ is phenyl substituted at least by $(CH_2)_nNR^cR^d$ at the 4-position wherein n is zero.

In another embodiment of the present invention there is provided a compound according to formula I wherein $X^1$ and $X^2$ are N, and $X^3$ and $X^4$ are $CR^5$; $R^3$ is (a) phenyl substituted at least by $(CH_2)_nNR^cR^d$ at the 4-position wherein n is zero or (b) $NR^aR^b$.

In another embodiment of the present invention there is provided a compound according to formula I wherein $R^1$ is 2-oxo-1,2-dihydro-pyridin-3-yl or 2,4-dioxo-3,4-dihydro-2H-pyrimidin-1-yl or 2,4-dioxo-1,2,3,4-tetrahydro-pyrimidin-5-yl optionally substituted by halogen, $C_{1-6}$ alkyl, $C_{1-3}$ haloalkyl or $C_{1-6}$ alkoxy; $X^1$ and $X^2$ are N, and $X^3$ and $X^4$ are $CR^5$ and $R^3$ is phenyl substituted at least by $(CH_2)_nNR^cR^d$ at the 4-position wherein n is zero or one.

In another embodiment of the present invention there is provided a compound according to formula I wherein $R^1$ is 2-oxo-1,2-dihydro-pyridin-3-yl, 2,4-dioxo-3,4-dihydro-2H-pyrimidin-1-y or 2,4-dioxo-1,2,3,4-tetrahydro-pyrimidin-5-yl optionally substituted by halogen, $C_{1-6}$ alkyl, $C_{1-3}$ haloalkyl or $C_{1-6}$ alkoxy; $X^1$ and $X^2$ are N, and $X^3$ and $X^4$ are $CR^5R^3$ is phenyl substituted at least by $(CH_2)_nNR^cR^d$ at the 4-position wherein n is zero and $R^4$ is $CR^{4a}R^{4b}R^{4c}$ and (a) $R^{4a}$, $R^{4b}$ and $R^{4c}$ are $CH_3$, $CD_3$ or fluorine or $R^{4a}$ and $R^{4b}$ together are $C_2$ alkylene and (b) $R^{4c}$ is $C_{1-3}$ alkyl, $C_{1-2}$ alkoxy, halogen, $C_{1-3}$ hydroxyalkyl, cyano or $C_{1-2}$ fluoroalkyl.

In another embodiment of the present invention there is provided a compound according to formula I wherein $R^1$ is 2-oxo-1,2-dihydro-pyridin-3-yl, 2,4-dioxo-3,4-dihydro-2H-pyrimidin-1-y or 2,4-dioxo-1,2,3,4-tetrahydro-pyrimidin-5-yl optionally substituted by halogen, $C_{1-6}$ alkyl, $C_{1-3}$ haloalkyl or $C_{1-6}$ alkoxy; $X^1$ and $X^2$ are N, and $X^3$ and $X^4$ are $CR^5$; $R^3$ is $NR^aR^b$; wherein $NR^aR^b$ together is cyclic amine substituted by $(CH_2)_nNR^eR^f$ wherein n is zero to two; and $R^e$ and $R^f$ are independently hydrogen, $C_{1-6}$ alkyl, $C_{1-6}$ haloalkyl, $SO_2R^8$ wherein $R^8$ is (a) $C_{1-6}$ alkyl, (b) $C_{1-6}$ haloalkyl, (c) $C_{3-7}$ cycloalkyl, (d) $C_{3-7}$ cycloalkyl-$C_{1-3}$ alkyl, (e) $C_{1-6}$ alkoxy-$C_{1-6}$ alkyl and $R^4$ is $CR^{4a}R^{4b}R^{4c}$ and (a) $R^{4a}$, $R^{4b}$ and $R^{4c}$ are $CH_3$, $CD_3$ or fluorine or $R^{4a}$ and $R^{4b}$ together are $C_2$ alkylene and (b) $R^{4c}$ is $C_{1-3}$ alkyl, $C_{1-2}$ alkoxy, halogen, $C_{1-3}$ hydroxyalkyl, cyano or $C_{1-2}$ fluoroalkyl.

In another embodiment of the present invention there is provided a compound according to formula I wherein $X^1$, $X^2$ and $X^4$ are $CR^5$ and $X^3$ is N In another embodiment of the present invention wherein $X^1$, $X^2$ and $X^4$ are $CR^5$ and $X^3$ is N; $R^3$ is (a) phenyl substituted at least by $(CH_2)_nNR^cR^d$ at the 4-position wherein n is zero or (b) $NR^aR^b$. The phrase "phenyl substituted at least by $(CH_2)_n NR^cR^d$ at the 4-position refers to (i) wherein unsubstituted positions can be further optionally substituted. The phrase" phenyl substituted at least by $(CH_2)_nNR^cR^d$ at the 4-position refers to (i) wherein unsubstituted positions can be further optionally substituted.

In another embodiment of the present invention there is provided a compound according to formula I wherein $X^1$ and $X^4$ are N and $X^2$ and $X^3$ are $CR^5$.

In another embodiment of the present invention there is provided a compound according to formula I where $X^1$ and $X^4$ are N and $X^2$ and $X^3$ are $CR^5$; $R^3$ is (a) phenyl substituted at least by $(CH_2)_nNR^cR^d$ at the 4-position wherein n is zero or (b) $NR^aR^b$. The phrase "phenyl substituted at least by $(CH_2)_n NR^cR^d$ at the 4-position refers to (i) wherein unsubstituted positions can be further optionally substituted. The phrase" phenyl substituted at least by $(CH_2)_nNR^cR^d$ at the 4-position refers to (i) wherein unsubstituted positions can be further optionally substituted.

In another embodiment of the present invention there is provided a compound according to formula I wherein $X^1$, $X^2$, $X^3$ and $X^4$ are $CR^5$ In another embodiment of the present invention there is provided a compound according to formula I where $X^1$, $X^2$, $X^3$ and $X^4$ are $CR^5$; $R^3$ is (a) phenyl substituted at least by $(CH_2)_nNR^cR^d$ at the 4-position wherein n is zero or (b) $NR^aR^b$. The phrase "phenyl substituted at least by $(CH_2)_n NR^cR^d$ at the 4-position refers to (i) wherein unsubstituted positions can be further optionally substituted. The phrase "phenyl substituted at least by $(CH_2)_nNR^cR^d$ at the 4-position refers to (i) wherein unsubstituted positions can be further optionally substituted.

In another embodiment of the present invention there is provided a compound according to of formula I wherein $X^1$ is N and $X^2$, $X^3$ and $X^4$ are $CR^5$, $R^1$ is 2,6-dioxo-tetrahydro-pyrimidin-1-yl, 2,5-dioxo-imidazolidin-1-yl or 2,4-dioxo-tetrahydro-pyrimidin-1-yl; and $R^3$ is (a) phenyl substituted at least by $(CH_2)_nNR^cR^d$ at the 4-position and wherein n is zero or (b) $NR^aR^b$.

In another embodiment of the present invention there is provided a compound selected from I-1 to I-31 of TABLE I.

In another embodiment of the present invention there is provided a compound selected from I-1 to I-33 of TABLE I.

In another embodiment of the present invention there is provide a method of treating a HCV infection in a patient in need thereof comprising administering a therapeutically effective amount of a compound according to formula I wherein $R^1$, $R^2$, $R^3$, $R^4$, $X^1$, $X^2$, $X^3$ and $X^4$ are as defined herein above.

In another embodiment of the present invention there is provide a method of treating a HCV infection in a patient in need thereof comprising co-administering a therapeutically effective amount of a compound according to formula I wherein $R^1$, $R^2$, $R^3$, $R^4$, $X^1$, $X^2$, $X^3$ and $X^4$ are as defined herein above and at least one immune system modulator and/or at least one antiviral agent that inhibits replication of HCV.

In another embodiment of the present invention there is provide a method of treating a disease caused by HCV in a patient in need thereof comprising co-administering a therapeutically effective amount of a compound according to formula I wherein $R^1$, $R^2$, $R^3$, $R^4$, $X^1$, $X^2$, $X^3$ and $X^4$ are as defined herein above and at least one immune system modulator selected from interferon, interleukin, tumor necrosis factor or colony stimulating factor.

In another embodiment of the present invention there is provide a method of treating a HCV infection in a patient in need thereof comprising co-administering a therapeutically effective amount of a compound according to formula I wherein $R^1$, $R^2$, $R^3$, $R^4$, $X^1$, $X^2$, $X^3$ and $X^4$ are as defined herein above and an interferon or chemically derivatized interferon.

In another embodiment of the present invention there is provide a method of treating a HCV infection in a patient in need thereof comprising co-administering a therapeutically effective amount of a compound according to formula I wherein $R^1$, $R^2$, $R^3$, $R^4$, $X^1$, $X^2$, $X^3$ and $X^4$ are as defined herein above and another antiviral compound selected from the group consisting of a HCV protease inhibitor, another HCV polymerase inhibitor, a HCV helicase inhibitor, a HCV primase inhibitor and a HCV fusion inhibitor.

In a another embodiment of the present invention there is provided a method for inhibiting viral replication in a cell by delivering a therapeutically effective amount of a compound of the formula I wherein $R^1$, $R^2$, $R^3$, $R^4$, $X^1$, $X^2$, $X^3$ and $X^4$ are as defined herein above admixed with at least one pharmaceutically acceptable carrier, diluent or excipient.

In a another embodiment of the present invention there is provided a composition comprising a compound according to formula I wherein $R^1$, $R^2$, $R^3$, $R^4$, $X^1$, $X^2$, $X^3$ and $X^4$ are as defined herein above with at least one pharmaceutically acceptable carrier, diluent or excipient.

The term "alkyl" as used herein without further limitation alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, lower alkyl groups include methyl, ethyl, propyl, iso-propyl, n-butyl, iert-butyl, tent-butyl, neopentyl, hexyl, and octyl. Any carbon hydrogen bond can be replaced by a carbon deuterium bond with departing from the scope of the invention.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (hetero)aryl refers to either an aryl or a heteroaryl group.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —$CH_2$CH(i-Pr)$CH_2$—), unless otherwise indicated. $C_{0-4}$ alkylene refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 12-fluoroethyl, 2-chloroethyl, 2-bromoethyl, 2,2-dichloroethyl, 3-bromopropyl or 2,2,2-trifluoroethyl. The term "fluoroalkyl" as used herein refers to a haloalkyl moiety wherein fluorine is the halogen.

The term "haloalkoxy" as used herein refers to a group —OR where R is haloalkyl as defined herein. The term "haloalkylthio" as used herein refers to a group —SR where R is haloalkyl as defined herein.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "halogen" or "halo" as used herein means fluorine, chlorine, bromine, or iodine.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The terms "alkoxycarbonyl" and "aryloxycarbonyl" as used herein denotes a group of formula —C(=O)OR wherein R is alkyl or aryl respectively and alkyl and aryl are as defined herein.

The term "cyano" as used herein refers to a carbon linked to a nitrogen by a triple bond, i.e., —C≡N. The term "nitro"

as used herein refers to a group —NO$_2$. The term "carboxy" as used herein refers to a group —CO$_2$H.

The term oxo refers to a doubly bonded oxygen (=O), i.e. a carbonyl group.

The term "acyl" (or "alkanoyl") as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term C$_{1-6}$ acyl or "alkanoyl" refers to a group —C(=O)R contain 1 to 6 carbon atoms. The C$_1$ acyl group is the formyl group wherein R=H and a C6 acyl group refers to hexanoyl when the alkyl chain is unbranched. The term "arylcarbonyl" or "aroyl" as used herein means a group of formula C(=O)R wherein R is an aryl group; the term "benzoyl" as used herein an "arylcarbonyl" or "aroyl" group wherein R is phenyl.

The term "cyclic amine" as used herein refers to a saturated carbon ring, containing from 3 to 6 carbon atoms as defined above, and wherein at least one of the carbon atoms is replaced by a heteroatom selected from the group consisting of N, O and S, for example, piperidine, piperazine, morpholine, thiomorpholine, di-oxo-thiomorpholine, pyrrolidine, pyrazoline, imidazolidine, azetidine wherein the cyclic carbon atoms are optionally substituted by one or more substituents, selected from the group consisting of halogen, hydroxy, phenyl, lower alkyl, lower alkoxy or 2-hydrogen atoms on a carbon are both replace by oxo (=O). When the cyclic amine is a piperazine, one nitrogen atom can be optionally substituted by C$_{1-6}$ alkyl, C$_{1-6}$ acyl, C$_{1-6}$ alkylsulfonyl.

The terms "alkylsulfonyl" and "arylsulfonyl" as used herein denotes a group of formula —S(=O)$_2$R wherein R is alkyl or aryl respectively and alkyl and aryl are as defined herein. The term C$_{1-3}$ alkylsulfonylamino as used herein refers to a group RSO$_2$NH— wherein R is a C$_{1-3}$ alkyl group as defined herein. The terms C$_{1-6}$ haloalkylsulfonyl, C$_{3-7}$ cycloalkylsulfonyl, C$_{3-7}$ cycloalkyl-C$_{1-3}$ alkyl-sulfonyl or C$_{1-6}$ alkoxy-C$_{1-6}$ alkylsulfonyl refer to a compound, S(=O)$_2$R wherein R is C$_{1-6}$ haloalkyl, C$_{3-7}$ cycloalkyl, C$_{3-7}$ cycloalkyl-C$_{1-3}$ alkyl and C$_{1-6}$ alkoxy-C$_{1-6}$ alkyl, respectively.

The terms "alkylsulfonylamido" and "arylsulfonylamido" as used herein denotes a group of formula —NR'S(=O)$_2$R wherein R is alkyl or aryl respectively, R' is hydrogen or C$_{1-3}$ alkyl, and alkyl and aryl are as defined herein. The term "sulfonylamino" may be use as a prefix while "sulfonylamide" is the corresponding suffix.

The term "sulfamoyl" as used herein refers to the radical —S(O)$_2$NH$_2$. The terms "N-alkylsulfamoyl" and "N,N-dialkylsulfamoyl" as used herein refers to the radical —S(O)$_2$NR'R", wherein R' and R" are hydrogen and lower alkyl and R' and R" are independently lower alkyl respectively. Examples of N-alkylsulfamoyl substituents include, but are not limited to methylaminosulfonyl, iso-propylaminosulfonyl. Examples of N,N-dialkylsulfamoyl substituents include, but are not limited to dimethylaminosulfonyl, iso-propyl-methylaminosulfonyl.

The term "carbamoyl" as used herein means the radical —CONH$_2$. The prefix "N-alkylcabamoyl" and "N,N-dialkylcarbamoyl" means a radical CONHR' or CONR'R" respectively wherein the R' and R" groups are independently alkyl as defined herein. The prefix N-arylcarbamoyl" denotes the radical CONHR' wherein R' is an aryl radical as defined herein.

The term "benzyl" as used herein refers to a C$_6$H$_5$CH$_2$ radical wherein the phenyl ring which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylamino sulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated.

The term "heteroaryl" as used herein without additional definition or limitation refers to "pyridinyl", "pyrazinyl" and "pyridazinyl" rings. The term "pyridine" ("pyridinyl") refers to a six-membered heteroaromatic ring with one nitrogen atom. The terms "pyrimidine" (pyrimidinyl), "pyrazine" ("pyrazinyl") and "pyridazine" ("pyridazinyl") refer to a six-membered nonfused heteroaromatic ring with two nitrogen atoms disposed in a 1,3, a 1,4 and a 1,2 relationship respectively. The respective radical names are in parentheses.

The terms "oxetane" (oxetanyl), "tetrahydrofuran" (tetrahydrofuranyl) and "tetrahydropyran" (tetrahydropyranyl") refer to a four, five and six-membered non-fused heterocyclic ring respectively, each containing one oxygen atom.

The term "aryl" as used herein refers to phenyl.

The terms (i) 3-oxo-3,4-dihydro-pyrazin-2-yl, (ii) 3-oxo-2,3-dihydro-pyridazin-4-yl, (iii) 2-oxo-1,2-dihydro-pyrimidin-4-one-5-yl, (iv) 2-oxo-1,2-dihydro-pyridin-3-yl, (v) 6-oxo-1,6-dihydro-[1,2,4]triazin-5-yl and (vi) 2,4-dioxo-1,2,3,4-tetrahydro-pyrimidin-5-yl refer to the following moieties:

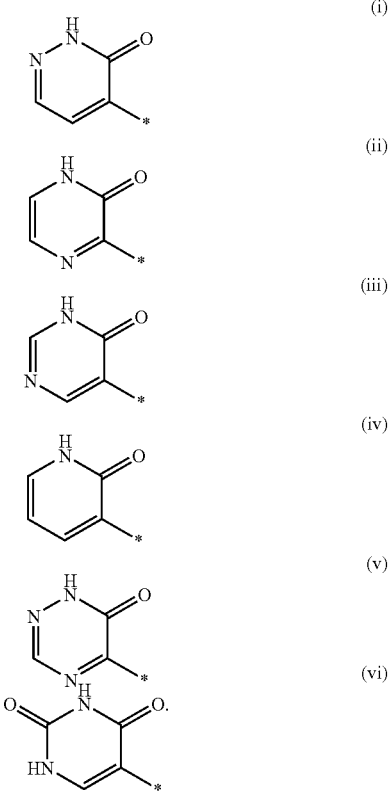

The terms (vii) 2,4-dioxo-3,4-dihydro-2H-pyrimidin-1-yl, (viii) 2-oxo-tetrahydro-pyrimidin-1-yl, (ix) 2-oxo-imidazolidin-1-yl, (x) 2-oxo-piperidin-1-yl, (xi) 2-oxo-pyrrolidin-1-yl (xii) 2,6-dioxo-tetrahydro-pyrimidin-1-yl and (xiii) 2,5-di-oxo-imidazolidin-1-yl refer to the following moieties:

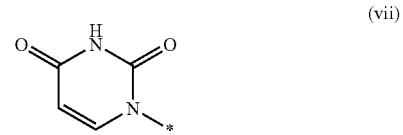

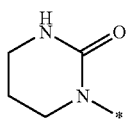
(viii)

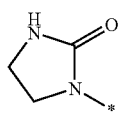
(ix)

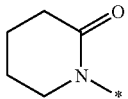
(x)

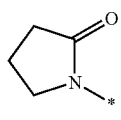
(xi)

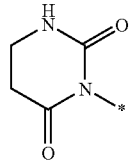
(xii)

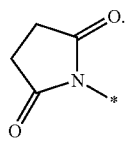
(xiii)

The terms (xiv) 2-oxo-2(H)-pyridin-1-yl, (xv) 6-oxo-6H-pyridazin-1-yl, (xvi) 6-oxo-6H-pyrimidin-1-yl, (xvii) 2-oxo-2H-pyrazin-1-yl and (xviii) 2,4-dioxo-tetrahydro-pyrimidin-1-yl refer to the following moieties:

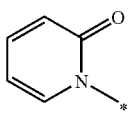
(xiv)

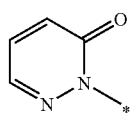
(xv)

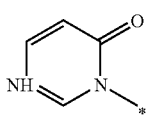
(xvi)

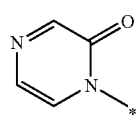
(xvii)

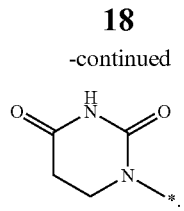
(xviii)

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and anti-infective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

In one embodiment, the compounds of the present invention according to formula I are used in combination with other active therapeutic ingredients or agents to treat patients with an HCV viral infection. According to the present invention, the active therapeutic ingredient used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, nucleoside inhibitors of HCV polymerase, non-nucleoside inhibitors of HCV polymerase, and other drugs for treating HCV, or mixtures thereof.

Examples of the nucleoside NS5b polymerase inhibitors include, but are not limited to NM-283, valopicitabine, R1626, PSI-6130 (R1656), IDX184 and IDX102 (Idenix) BILB 1941.

Examples of the non-nucleoside NS5b polymerase inhibitors include, but are not limited to HCV-796 (ViroPharma and Wyeth), MK-0608, MK-3281 (Merck), NM-107, R7128 (R4048), VCH-759, GSK625433 and GSK625433 (Glaxo), PF-868554 (Pfizer), GS-9190 (Gilead), A-837093 and A848837 (Abbot Laboratories), ANA598 (Anadys Pharmaceuticals); GL100597 (GNLB/NVS), VBY 708 (ViroBay), benzimidazole derivatives (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1), benzo-1,2,4-thiadiazine derivatives (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed Oct. 31, 2003), 1,1-dioxo-4H-benzo[1,4]thiazin-3-yl derivatives (J. F. Blake et al. in U.S. Patent Publication US20060252785 and 1,1-dioxo-benzo[d]isothazol-3-yl compounds (J. F. Blake et al. in U.S. Patent Publication 2006040927).

Examples of the HCV NS3 protease inhibitors include, but are not limited to SCH-503034 (Schering, SCH-7), VX-950 (telaprevir, Vertex), BILN-2065 (Boehringer-Ingelheim, BMS-605339 (Bristol Myers Squibb), and ITMN-191 (Intermune).

Examples of the interferons include, but are not limited to pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen and actimmune, IFN-omega with DUROS, albuferon, locteron, Albuferon, Rebif, oral interferon alpha, IFNalpha-2b XL, AVI-005, PEG-Infergen, and pegylated IFN-beta.

Ribavirin analogs and the ribavirin prodrug viramidine (taribavirin) have been administered with interferons to control HCV.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride (BOC2O), benzyl (Bn), butyl (Bu), Chemical Abstracts Registration Number (CASRN), benzyloxycarbonyl (CBZ or Z), carbonyl diimidazole (CDI), 1,5-diazabicyclo[4.3.0]non-5-ene (DBN), 1,8-diazabicyclo[5.4.0]undec-7-ene (DBU), N,N'-dicyclohexyl-carbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), ethyl (Et), ethanol (EtOH), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl acetate (EtOAc), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), MeSO$_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-BuMe$_2$Si (TBDMS), triethylamine (TEA or Et$_3$N), triflate or CF$_3$SO$_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n-), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The following numbering system is used herein.

TABLE I

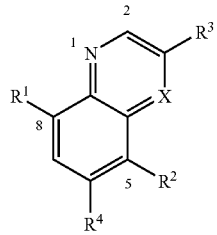

| Cmpd. No. | Structure | IC$_{50}$[1] | MP | MS |
|---|---|---|---|---|
| I-1 | 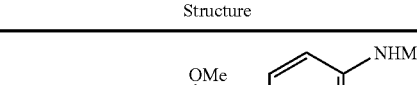 | 0.008 | 274.0-276.0 | 478 |

TABLE I-continued

| Cmpd. No. | Structure | IC$_{50}$[1] | MP | MS |
|---|---|---|---|---|
| I-2 | 5-fluoro-pyridin-2(1H)-one linked to quinoxaline bearing 7-CMe$_3$ and 3-(4-NHMs-phenyl) | 0.031 | >300 | 467 |
| I-3 | pyridin-2(1H)-one linked to quinoxaline bearing 7-CMe$_3$ and 3-(4-NHMs-piperidin-1-yl) | | 275.0–280.0 | 456 |
| I-4 | 5-fluoro-pyridin-2(1H)-one linked to quinoxaline bearing 7-CMe$_3$ and 3-(3-(MsHNCH$_2$)-pyrrolidin-1-yl) | 0.191 | 170.0–175.0 | 474 |
| I-5 | 5-fluoro-pyridin-2(1H)-one linked to quinoxaline bearing 7-CMe$_3$ and 3-(4-NHMs-piperidin-1-yl) | 0.817 | 224.0–226.0 | 474 |

TABLE I-continued

[Structure diagram: quinoxaline core with positions labeled 1, 2, 5, 8, X, and substituents R¹ (8), R² (5), R³ (adjacent to position 2), R⁴ (below position 5)]

| Cmpd. No. | Structure | IC$_{50}$[1] | MP | MS |
|---|---|---|---|---|
| I-6 | [pyridin-2(1H)-one linked to quinoxaline with CMe₃ substituent and phenyl-NHMs group] | 0.001 | 260.0-263.0 | 449 |
| I-7 | [pyridin-2(1H)-one linked to quinoxaline with CMe₃ substituent and chloro-phenyl-NHMs group] | 0.003 | 275.0-278.0 | 483/485 |
| I-8 | [pyridin-2(1H)-one linked to quinoxaline with CMe₃ substituent and fluoro-phenyl-NHMs group] | 0.004 | 467 |  |
| I-9 | [MeO-pyridin-2(1H)-one linked to quinoxaline with CMe₃ substituent and chloro-phenyl-NHMs group] | 0.001 | 513/515 |  |

TABLE I-continued
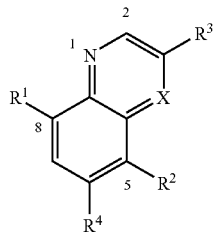
| Cmpd. No. | Structure | IC$_{50}$[1] | MP | MS |
|---|---|---|---|---|
| I-10 | 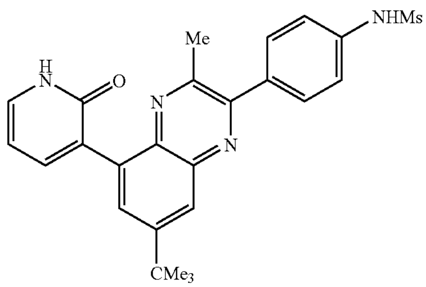 | 0.021 | | 463 |
| I-11 | 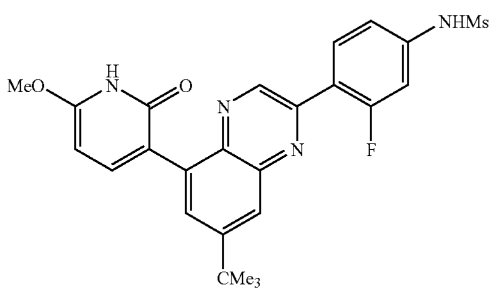 | 0.001 | | 497 |
| I-12 | 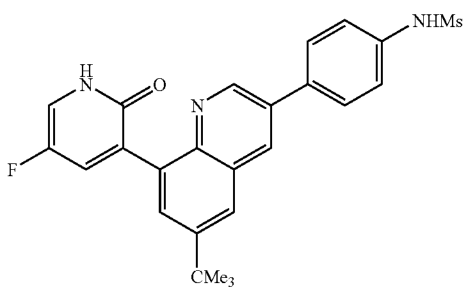 | 0.006 | 208.0-210.0 | |
| I-13 | 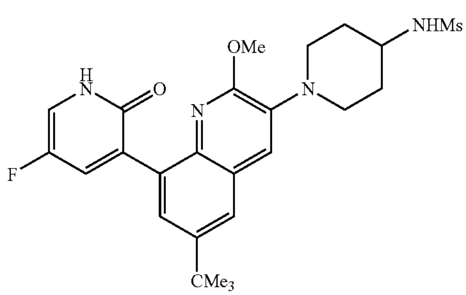 | 0.064 | 186.0-188.0 | 473 |

TABLE I-continued
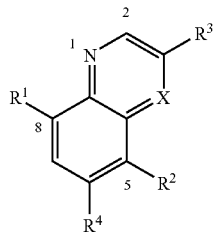
| Cmpd. No. | Structure | IC$_{50}$[1] | MP | MS |
|---|---|---|---|---|
| I-14 | 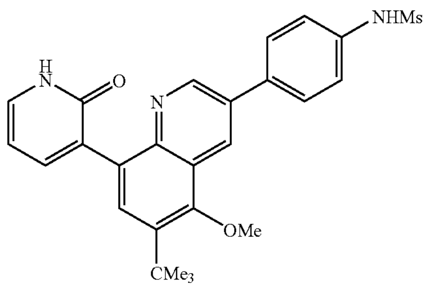 | 0.001 | | 478 |
| I-15 | 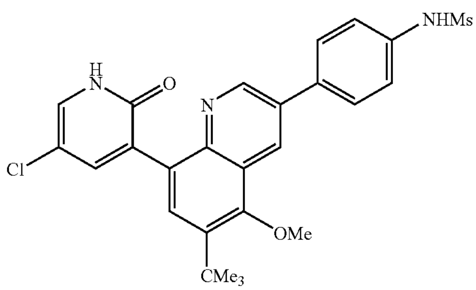 | 0.001 | | 511/513 |
| I-16 | 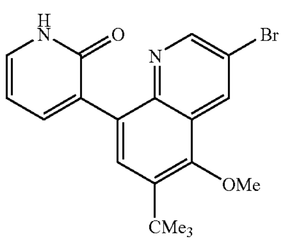 | 0.059 | | 387-389 |
| I-17 | 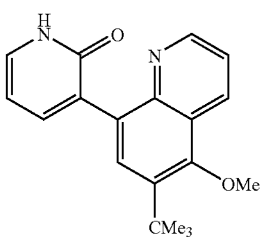 | 0.038 | | 309 |

TABLE I-continued

| Cmpd. No. | Structure | IC$_{50}$[1] | MP | MS |
|---|---|---|---|---|
| I-18 | 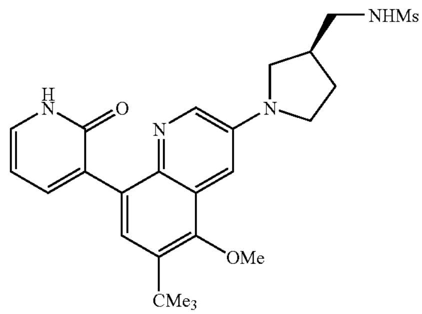 | 0.0002 | 275.0-280.0 | 485 |
| I-19 | 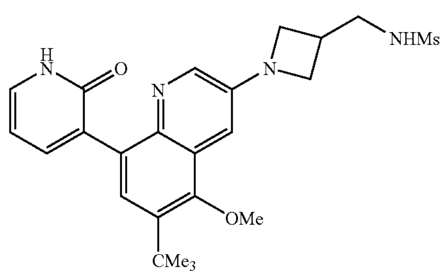 | 0.003 | 177.0-180.0 | 471 |
| I-20 | 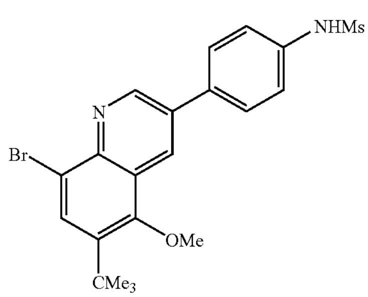 | 0.225 | | 463/465 |
| I-21 | 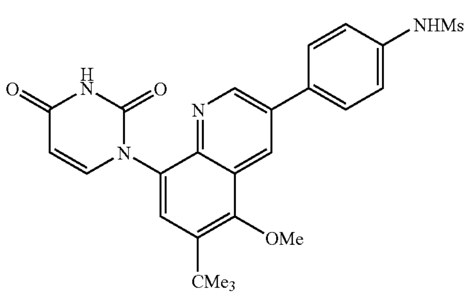 | 0.0022 | 277.0-281.0 | 495 |

TABLE I-continued

| Cmpd. No. | Structure | IC$_{50}$[1] | MP | MS |
|---|---|---|---|---|
| I-22 | 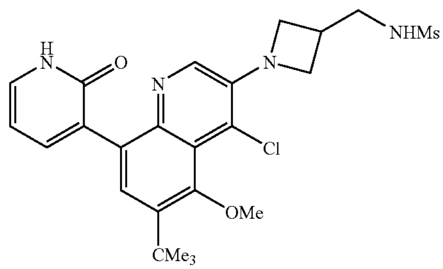 | 0.044 | | 505/507 |
| I-23 | 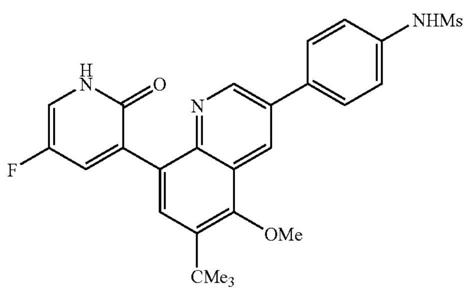 | 0.001 | | 496 |
| I-24 | 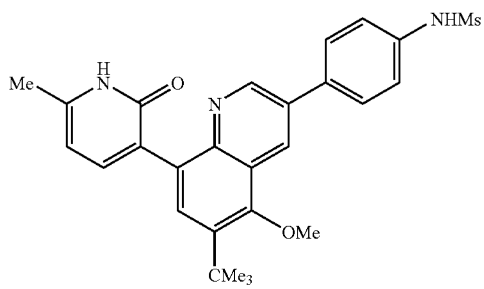 | 0.001 | | 492 |
| I-25 | 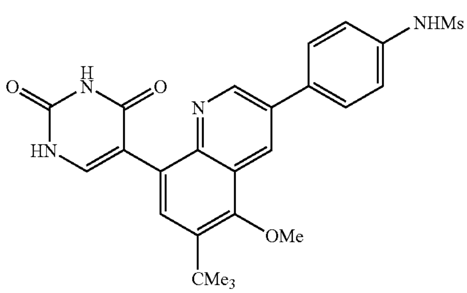 | 0.0004 | | 495 |

TABLE I-continued
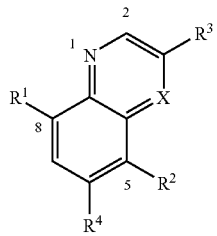
| Cmpd. No. | Structure | IC$_{50}$[1] | MP | MS |
|---|---|---|---|---|
| I-26 | 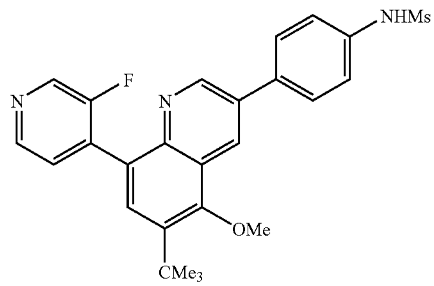 | 0.001 | | 480 |
| I-27 | 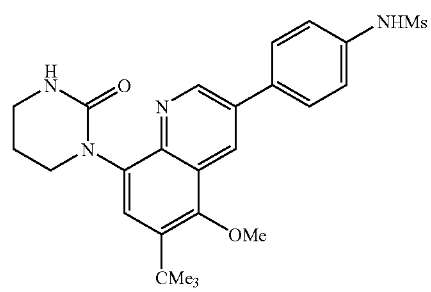 | 0.0007 | | 483 |
| I-28 | 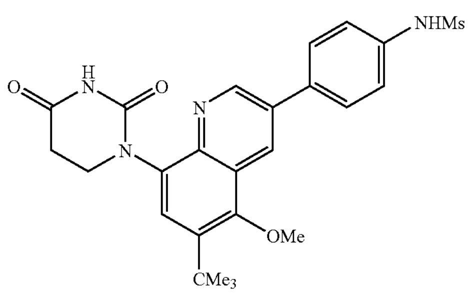 | 0.002 | | 497 |
| I-29 | 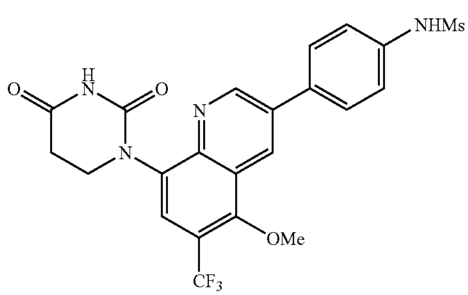 | 0.0018 | | 502 |

TABLE I-continued
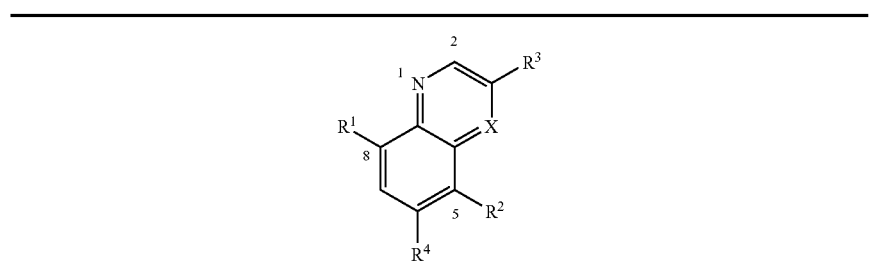
| Cmpd. No. | Structure | IC$_{50}$[1] | MP | MS |
|---|---|---|---|---|
| I-30 | 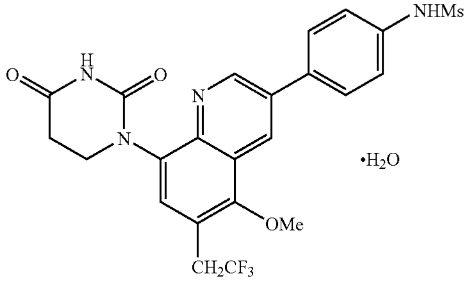 | 0.017 | | 523 |
| I-31 | 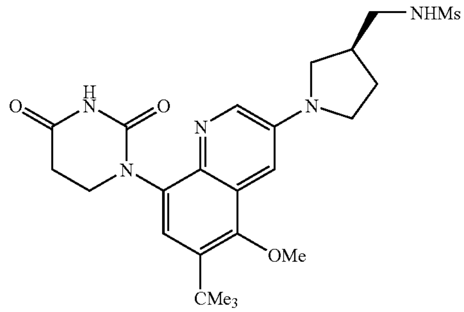 | 0.0018 | | 504 |
| I-32 | 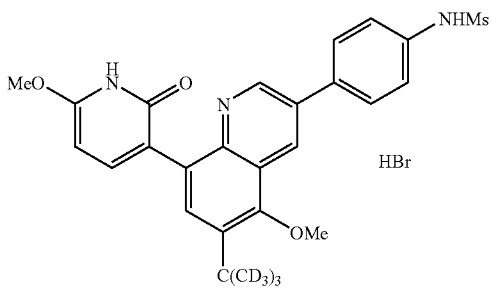 | 0.0008 | | 517.2 |
| I-33 | 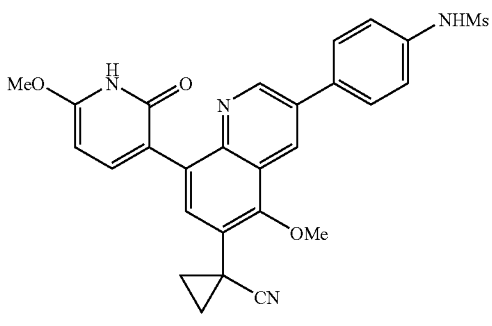 | 0.0038 | | 517 |

TABLE I-continued
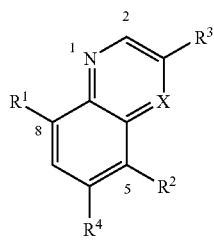
| Cmpd. No. | Structure | IC$_{50}$[1] | MP | MS |
|---|---|---|---|---|
| I-34 | 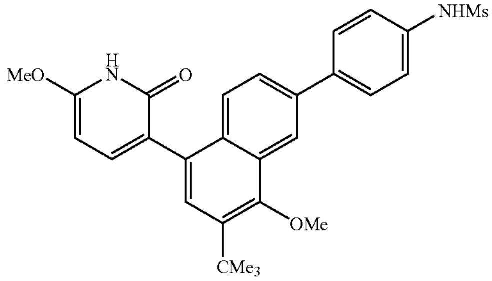 | 0.01 | | 508 |
| I-35 | 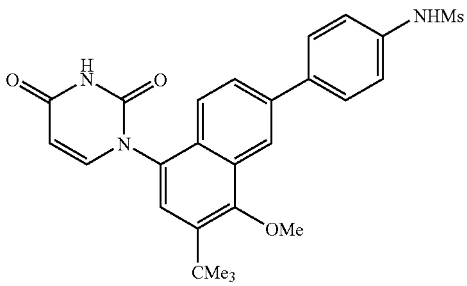 | 0.0129 | | 494 |
| I-36 | 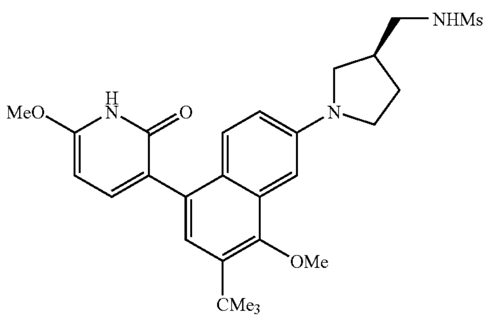 | 0.0084 | | 514 |
| I-37 | 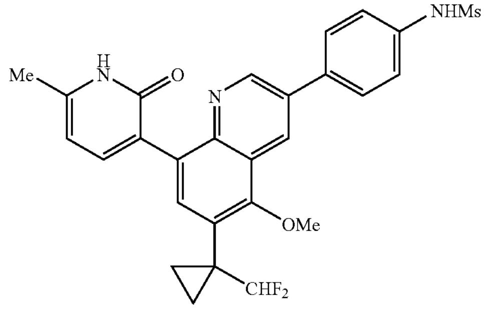 | 0.0099 | | 526 |

TABLE I-continued
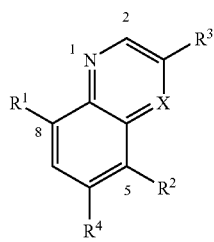
| Cmpd. No. | Structure | IC$_{50}$[1] | MP | MS |
|---|---|---|---|---|
| I-38 | 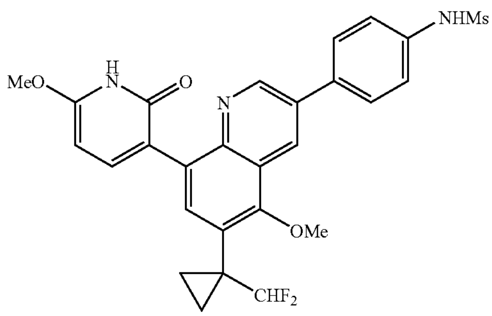 | 0.0006 | | 542 |
| I-39 | 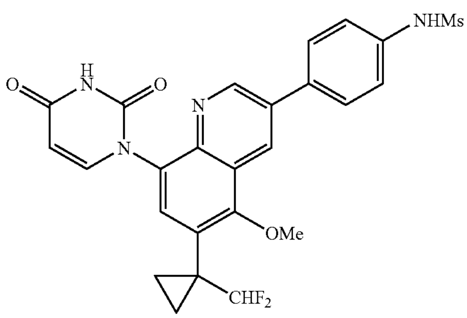 | 0.0034 | | 529 |
| I-40[2] | 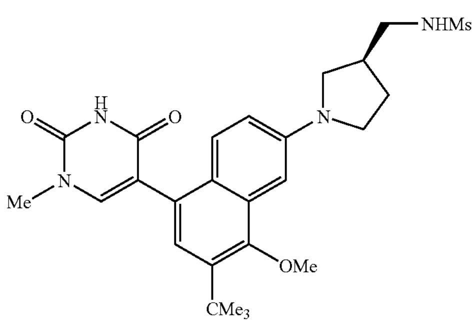 | 0.0066 | | — |
| I-41 | 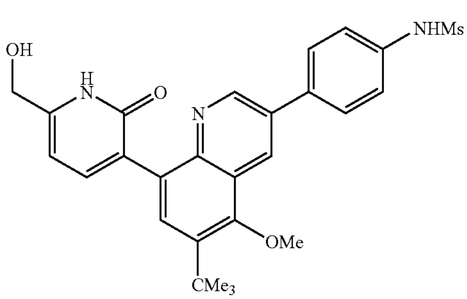 | 0.0002 | 293.0-295.0 | 508 |

TABLE I-continued
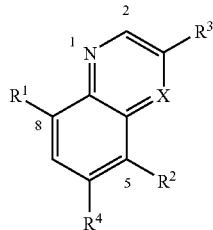
| Cmpd. No. | Structure | IC$_{50}$[1] | MP | MS |
|---|---|---|---|---|
| I-42 | 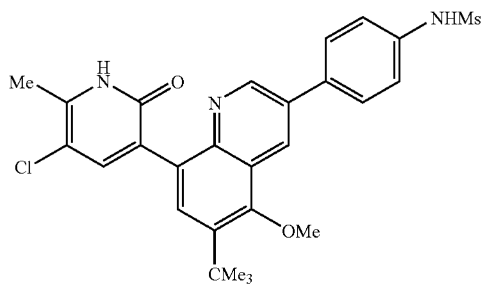 | 0.0006 | | 527 |
| I-43 | 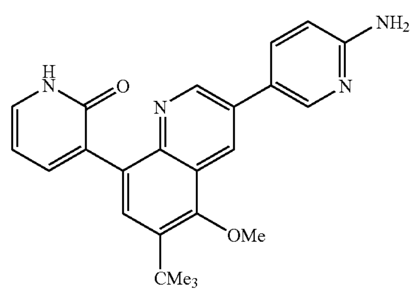 | 0.0026 | | 401 |
| I-44 | 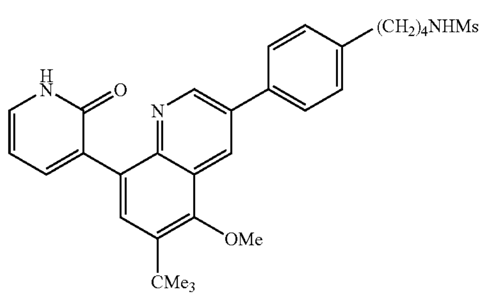 | 0.0122 | | 472 |
| I-45 | 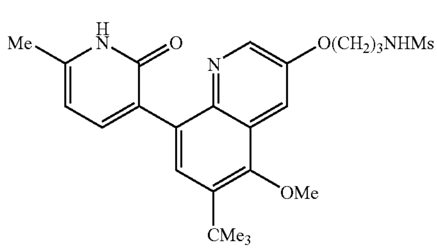 | 0.0118 | | 474 |

TABLE I-continued
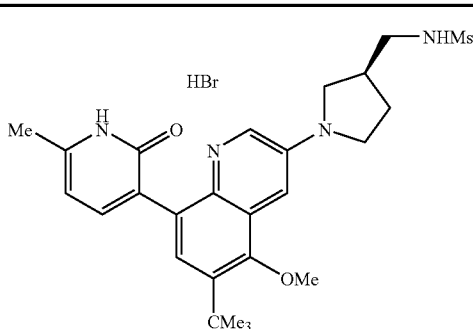
| Cmpd. No. | Structure | IC$_{50}$[1] | MP | MS |
|---|---|---|---|---|
| I-46 | 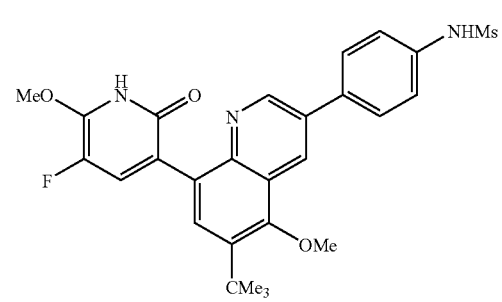 | 0.0009 | | 499 |
| I-47 | 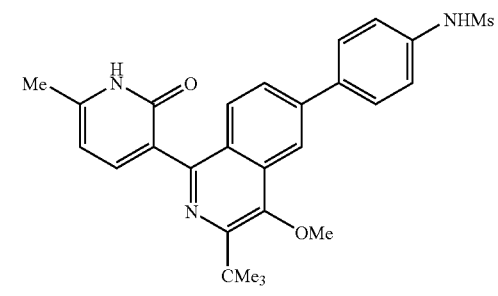 | 0.0128 | | 526 |
| I-48 | 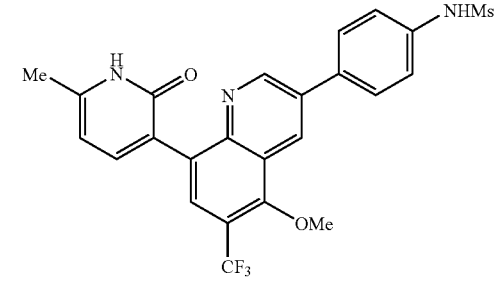 | — | | 462 |
| I-49 | 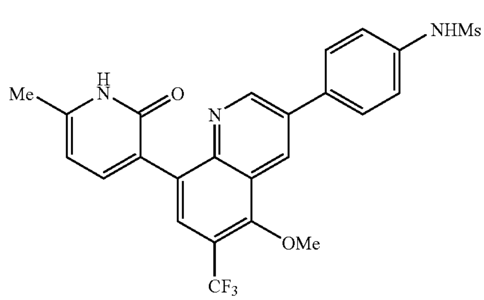 | 0.0007 | | 504 |

TABLE I-continued
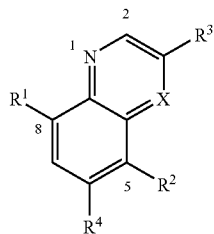
| Cmpd. No. | Structure | IC$_{50}$[1] | MP | MS |
|---|---|---|---|---|
| I-50 | 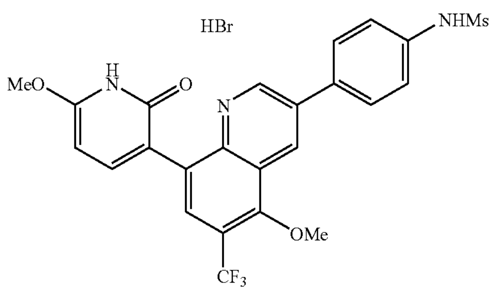 | 0.0006 | | 520 |
| I-51 | 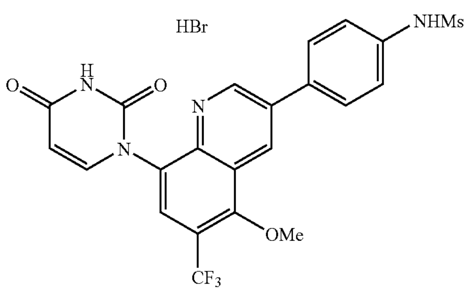 | 0.0038 | | 507 |
| I-52 | 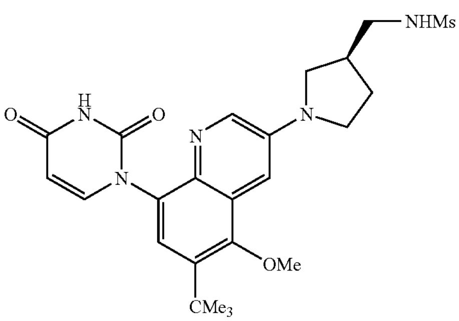 | 0.0035 | | 502 |
| I-53 | 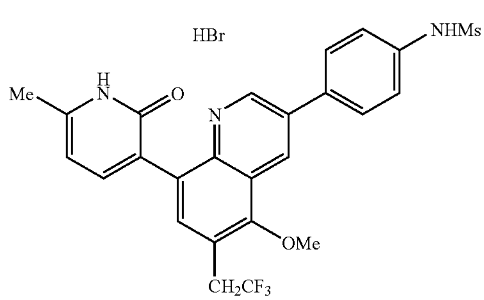 | 0.0096 | | 518 |

TABLE I-continued

| Cmpd. No. | Structure | IC$_{50}$[1] | MP | MS |
|---|---|---|---|---|
| I-54 | MeO-pyridinone-HBr / quinoline(8-linked, 5-OMe, 6-CH$_2$CF$_3$, 3-aryl-NHMs) | 0.0022 | | 534 |
| I-55 | MeO-pyridinone / quinoline(8-linked, 5-OMe, 6-CMe$_3$, 3-aryl-NHMs) | 0.0086 | | 515 |
| I-56 | pyridine-2,6-dione-HBr / quinoline(8-linked, 5-OMe, 6-CH$_2$CF$_3$, 3-aryl-NHMs) | 0.0385 | | 521 |
| I-57 | dihydropyrimidine-2,4-dione·H$_2$O / quinoline(8-N-linked, 5-OMe, 6-CH$_2$CF$_3$, 3-aryl-NHMs) | 0.0174 | | 508 |

TABLE I-continued
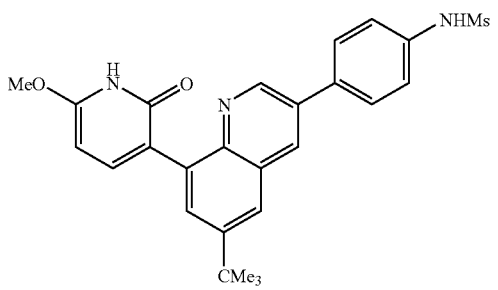
| Cmpd. No. | Structure | IC$_{50}$[1] | MP | MS |
|---|---|---|---|---|
| I-58 | 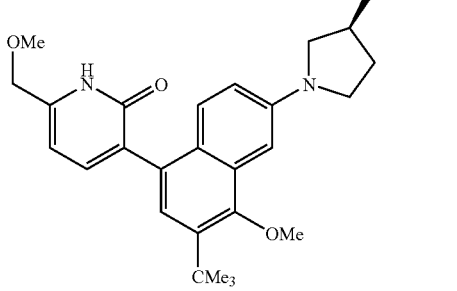 | 0.006 | | 478 |
| I-59 | 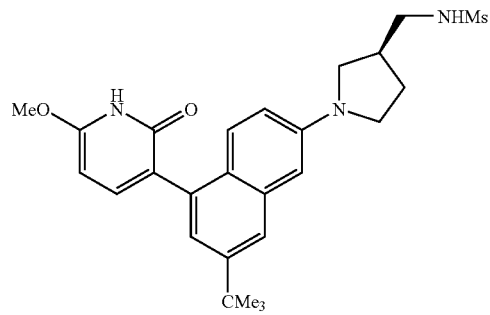 | 0.0009 | | 467 |
| I-60 | 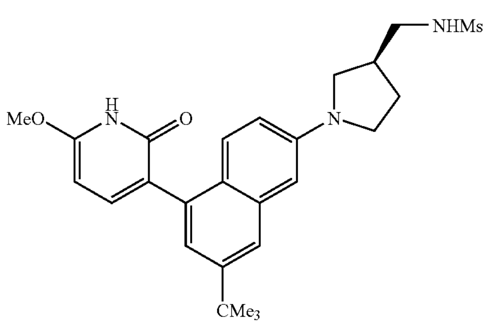 | — | | 485 |
1. HCV Polymerase Activity (μmol) See Example 37
2. $^1$H NMR: δ(CDCl$_3$) 1.486 (tert-Bu), 2.97 (SO$_2$Me), 3.438 (NMe), 3.932 (OMe)

The compounds in TABLE II exemplify further compounds within the scope of the present invention.

TABLE II

II-1
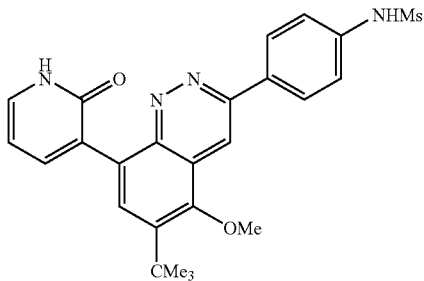

II-2
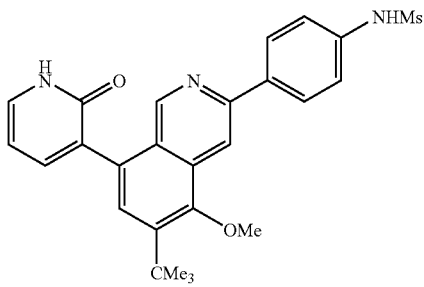

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

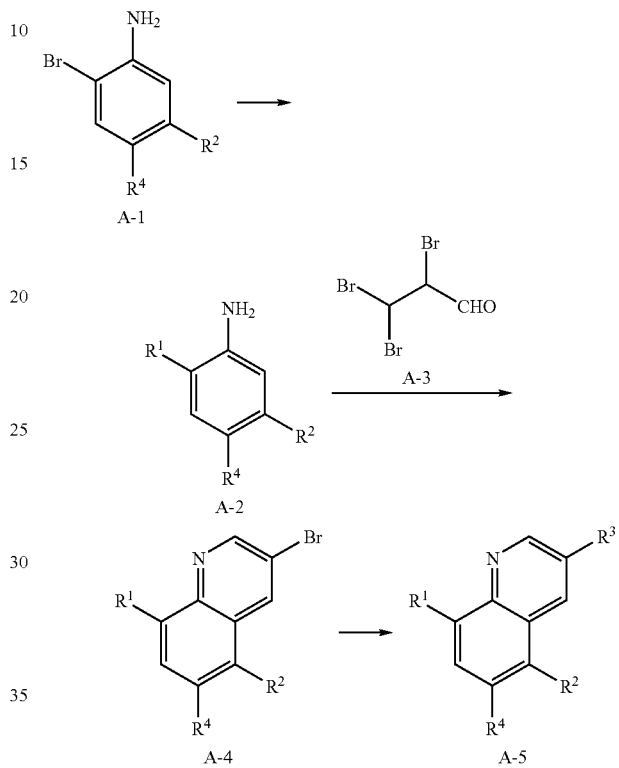

SCHEME A

Quinoline derivatives encompassed by the present invention are prepared by a modification of the Skraup quinoline synthesis wherein the acid catalyzed condensation of an aniline A-2 and 1,2,2-tribromo-acrolein (A-3) affords the bromoquinoline A-4. The condensation is typically carried out on an aniline wherein R$^1$ is a heteroaryl moiety as provided in the Summary of the Invention or a protected form thereof which is ultimately converted to said heteroaryl moiety. Introduction of the heteroaryl moiety to afford A-2 wherein R$^2$ is heteroaryl is readily accomplished by palladium-catalyzed coupling of an ortho bromoaniline A-1 and a heteroaryl boronic acid.

Boronic acids which are useful in the preparation of the compounds of the present invention include, but are not limited to, 2-methoxy-pyridin-3-yl boronic acid (CASRN 163105-90-6), 2-benzyloxy-3-pyridine boronic acid, 2-oxo-1,2-dihydropyridine-3-boronic acid (CASRN 951655-49-5), 5-fluoro-2-methoxy-3-pyridine boronic acid (CASRN 957120-32-0), 2-methoxy-6-methyl-pyridin-3-yl boronic acid (CASRN 1000802-75-4), 5-chloro-2-methoxy-pyridin-3-ylboronic acid (CASRN 943153-22-8), 2,6-dimethoxy-pyridin-3-yl boronic acid (115, CASRN 221006-70-8, B-(2,3-dihydro-3-oxo-4-pyridazinyl)-boronic acid (Example 16) or 2,4-dioxo-1,2,3,4-tetrahydropyrimidin-5-yl boronic acid (CASRN 70523-22-7). One skilled in the art will recognize that boronic acids and boronic esters such as the 4,4,5,5-tetramethyl-[1,3,2]dioxaborolan-2-yl ester can be used interchangeably in the Suzuki coupling. The oxo group can be masked as an alkyl ether requiring a subsequent dealkylation step to afford the oxo group which is readily carried out by heating in HBr/HOAc. Alternatively the benzyl ether can be used ands deprotected with in HBr/HOAc or catalytic hydrogenation.

After elaboration of the quinoline, a second Suzuki coupling with an aryl boronic acid such as 4-(methanesulfonamido)-phenyl boronic acid or 4-nitrophenyl boronic acid allows direct introduction of the 3-aryl substituent as $R^3$ and affords A-5. One of skill in the art will appreciate the availability of a wide range of aryl boronic acids which affords enormous flexibility with regard to the sequence of the requisite functional group transformations and the nature of the $R^3$ substituent.

The Skraup condensation also can be carried out on the bromoaniline to afford A-4 wherein $R^1$ is a bromine and the Suzuki-coupling to introduce the heteroaryl $R^1$ substituent is subsequently carried out on the quinoline. As demonstrated in example 13, preferential coupling takes place at the 3-position. The availability of the 8-bromo derivative (B-1) affords additional synthetic flexibility. Metallation of the 8-bromoquinoline wherein Ar is unreactive under the reaction conditions allows the introduction of a boronic acid onto the quinoline ring (B-2) which can be subjected to Suzuki coupling with heteroaryl compounds substituted by halogen or trifluoromethylsulfonyloxy substituents such as 2-chloro-3-methoxy-pyrazine (CASRN 40155-28-0) which can be demethylated to afford the 3-oxo-3,4-dihydro-pyrazin-2-yl moiety.

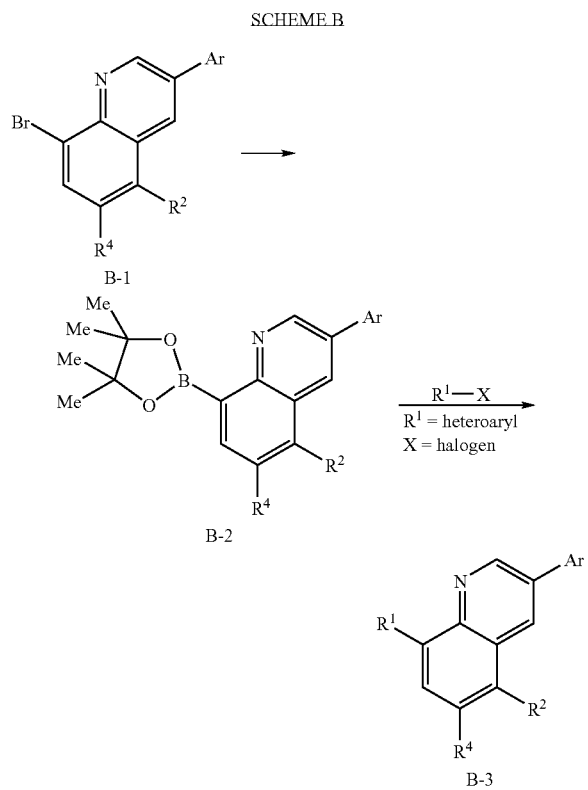

SCHEME B

The Suzuki reaction is a palladium-catalyzed coupling of a boronic acid ($R$—$B(OH)_2$) wherein R is aryl or vinyl) with an aryl or vinyl halide or triflate (R'Y wherein R'=aryl or vinyl; Y=halide or —$OSO_2CF_3$) o afford a compound R—R'. Typical catalysts include $Pd(PPh_3)_3$, $Pd(OAc)_2$ and $PdCl_2(dppf)$. With $PdCl_2(dppf)$, primary alkyl borane compounds can be coupled to aryl or vinyl halide or triflate without β-elimination. Highly active catalysts have been identified (see, e.g. J. P. Wolfe et al., *J. Am. Chem. Soc.* 1999 121(41):9550-9561 and A. F. Littke et al., *J. Am. Chem. Soc.* 2000 122(17):4020-4028). The reaction can be carried out in a variety of organic solvents including toluene, THF, dioxane, DCE, DMF, DMSO and MeCN, aqueous solvents and under biphasic conditions. Reactions are typically run from about RT to about 150° C. Additives (e.g. CsF, KF, TlOH, NaOEt and KOH) frequently accelerate the coupling. There are a large number of variables in the Suzuki reaction including the palladium source, ligand, additives and temperature and optimum conditions sometimes require optimization of the parameters for a given pair of reactants. A. F. Littke et al., supra, disclose conditions for Suzuki cross-coupling with arylboronic acids in high yield at RT utilizing $Pd_2(dba)_3$/P(tert-bu)$_3$ and conditions for cross-coupling of aryl- and vinyl triflates utilizing $Pd(OAc)_2$/$P(C_6H_{11})_3$ at RT. J. P. Wolf et al., supra, disclose efficient condition for Suzuki cross-coupling utilizing $Pd(OAc)_2$%-(di-tert-butylphosphino)biphenyl or o-(dicyclohexylyphosphino)biphenyl. One skilled in the art can determine optimal conditions without undue experimentation.

SCHEME C

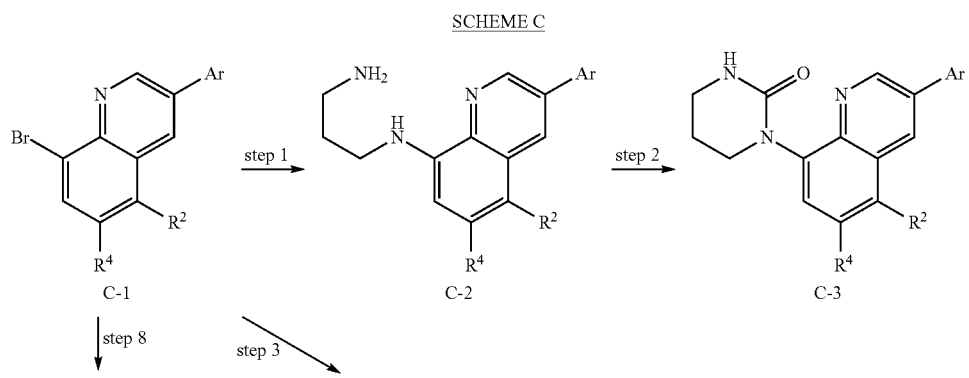

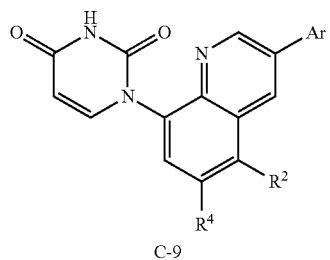

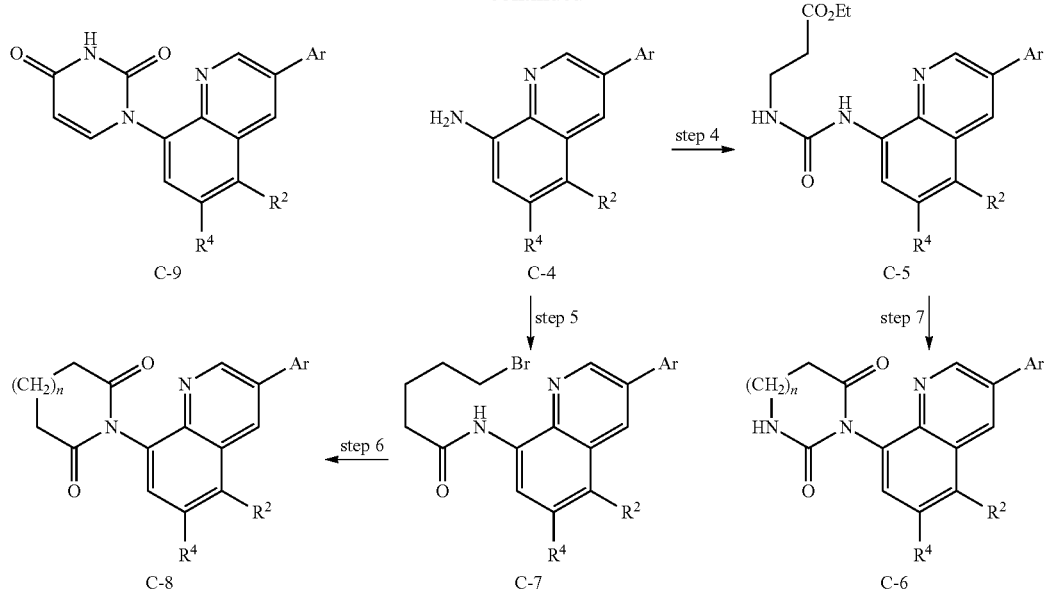

Compounds of general formula I wherein $R^1$ is a heterocycle linked by a carbon-nitrogen bond can be prepared by a copper- or palladium-catalyzed aryl amination reaction. Aryl amination procedures have been described. Introduction of 2-oxo-tetrahydro-pyrimidin-1-yl or 2-oxo-imidazolidin-1-yl substituents can be accomplished by CuI catalyzed aryl amination of a bromoquinoline with 1,3-diamino-propane (step 1) or 1,2-diamino-ethane (D. Ma et al., Org. Lett. 2003 5(14): 2453) followed by intramolecular cyclization with carbonyl diimidazole (step 2). Alternatively, a heterocyclic ring can be elaborated from the primary amine C-4. Numerous procedures have been described which introduce a primary amine onto an aryl ring by displacement of a halogen (step 3). (J. P. Wolfe et al. Tetrahedron Lett. 1997 38(36):6367; C.-Z. Tao et al., Tetrahedron Lett. 2008 49:70; Q. Shen and J. F. Hartwig, J. Am. Chem. Soc. 2006 128:10028; S. S. Surry and S. L. Buchwald, J. Am. Chem. Soc. 2007 129:10354) Acylation of C-4 with 5-bromo-pentanoic acid (step 5) or 4-bromo-butyric acid followed by intramolecular cyclization (step 6) affords the piperidone (C-8, n=1) and pyrrolidone (C-8, n=0) substituents respectively. Condensation of C-4 and ethyl 3-isocyanatopropanoate (CASRN 5100-34-5) or ethyl 4 isocyanatoacetate (CASRN 2949-22-6) (step 4) and subsequent intramolecular acylation (step 7) affords 2,5-dioxo-imidazolidin-1-yl (C-6, n=0) or 2,6-dioxo-tetrahydro-pyrimidin-1-yl moieties (C-6, n=1) moieties respectively. The 2,4-dioxo-3, 4-dihydro-2H-pyrimidin-1-yl (C-9) moiety could be introduced by CuI catalyzed displacement of the bromine with uracil. (step 8) (R. Wagner et al. WO2009/039127)

Compounds of general formula A-5 wherein aryl-$R^3$ bond is a carbon nitrogen bond can be prepared by the palladium-catalyzed displacement of the bromo substitutent in A-3 with an optionally substituted cyclic amine as illustrated in Examples 11 and 12. (J. F. Hartwig et al., J. Org. Chem. 1999 64:5575).

Substitution at the two position was introduced via the quinolone (Example 1) which was prepared by palladium catalyzed cross-coupling of methyl acrylate and 20a utilizing the Heck protocol and acid-catalyzed cyclization of the lactam, O-alkylation of the lactam affords the 2-methoxy substituent. The reaction of the quinolone and phosphorous oxyhalides will afford the 2-halo-quinoline which can be displaced to introduce other functionality.

Introduction of acyclic substituents at $R^3$ was accomplished utilizing a Heck coupling to link the heteroaryl halide and a suitable substituted alkene or alkyne (see, e.g. example 29) The Heck reaction (or Mizoroki-Heck reaction) is the palladium catalyzed coupling of an aryl, alkenyl, alkynyl or benzyl halide or triflate with an alkene styrene, acrylate ester, acrylonitrile enol ether or enol thioether. (A. se Meijere and F. E. Meyer, Angew Chem. Int. Ed. English 1994 33:2379-2411; W. Cabri and I. Candiani, Acc. Chem. Res. 1995 28(1):2-7) containing at least one proton and is often electron-deficient such as acrylate ester or an MeCN. Commonly used palladium catalysts include $Pd(PPh_3)_4$, $Pd(OAc)_2$, $PdCl_2$, $Pd_2(dba)_3$. Phosphine ligands such as $PPh_3$, $P(o\text{-}Tol)_3$ and BINAP are commonly incorporated into the reaction mixture either as preformed phosphine complexes or as free phosphines which can form complexes in situ. Bases such as TEA, 1,2,2,6,6-pentamethyl-piperidine, DBU, $K_2CO_3$, KOAc, $Ag_2CO_3$ and KO-tent-Bu are typically required. The reaction is commonly run in aprotic solvents, frequently DMF, DMSO, NMP or MeCN; however, less polar solvents and aqueous cosolvents can also be utilized. While there are several reaction variables, protocols have been identified and one skilled in the art can identify useful conditions without undue experimentation.

Analogous transformations afford compounds of general formula I wherein $R^4$ is other than tent-butyl. Dibromination of 4-(1-methylcyclopropyl)benzeneamine (CASRN 114833-72-6) or 1-(4-aminophenyl)cyclopropane carbonitrile (CASRN108858-86-2) affords intermediates which can be subjected to a completely analogous reaction sequence. Alternatively methyl 4-amino-5-bromo-2-methoxybenzoate (CASRN 111049-68-4) can be subjected to the Skraup synthesis which affords methyl 3,8-dibromo-5-methoxy-quinoline-6-carboxylate (122a) which is converted to the corresponding cyclopropanecarbonitrile (124a) by conventional methodology (see, e.g., example 25). nitrile group can be readily converted to the corresponding aldehyde (and therefore also the corresponding acid and ester) and thence to the difluoromethyl (by DAST fluorination) or the hydroxymethyl (by BH₃ reduction) substituents. Analogous transformations can be utilized to afford the corresponding des-methoxy analogues. 4-Trifluoromethyl-aniline (CASRN 455-14-1) and 3-methoxy-4-trifluoromethyl-aniline can be converted to quinolines and quinazolines analogously.

SCHEME D

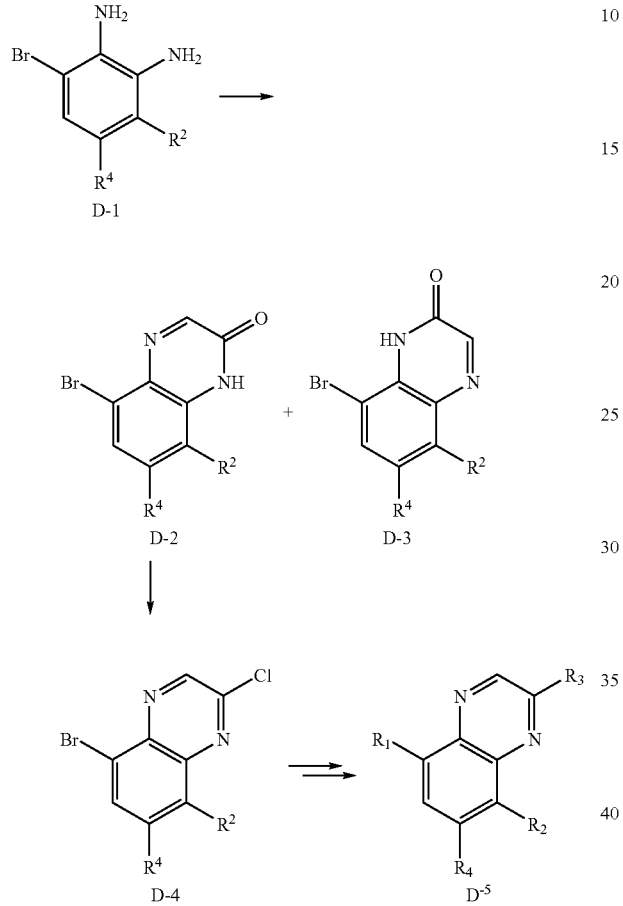

Quinazolines encompassed by the present invention were prepared by condensation of an suitable substituted ortho-diaminobenzene with a 1,2-dicarbonyl compound. For example, ethyl glyoxylate and 32 were condensed to afford a mixture of 5-bromo-7-tent-butyl-1H-quinoxalin-2-one and 8-bromo-6-tert-butyl-1H-quinoxalin-2-one. Introduction of the C-3 and C-8 substituents can be carried out by successive displacements as described previously (see, e.g., example 2).

SCHEME E

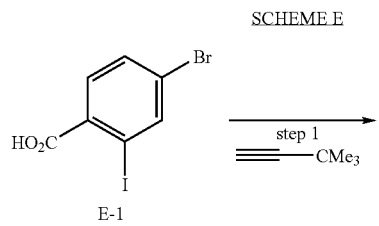

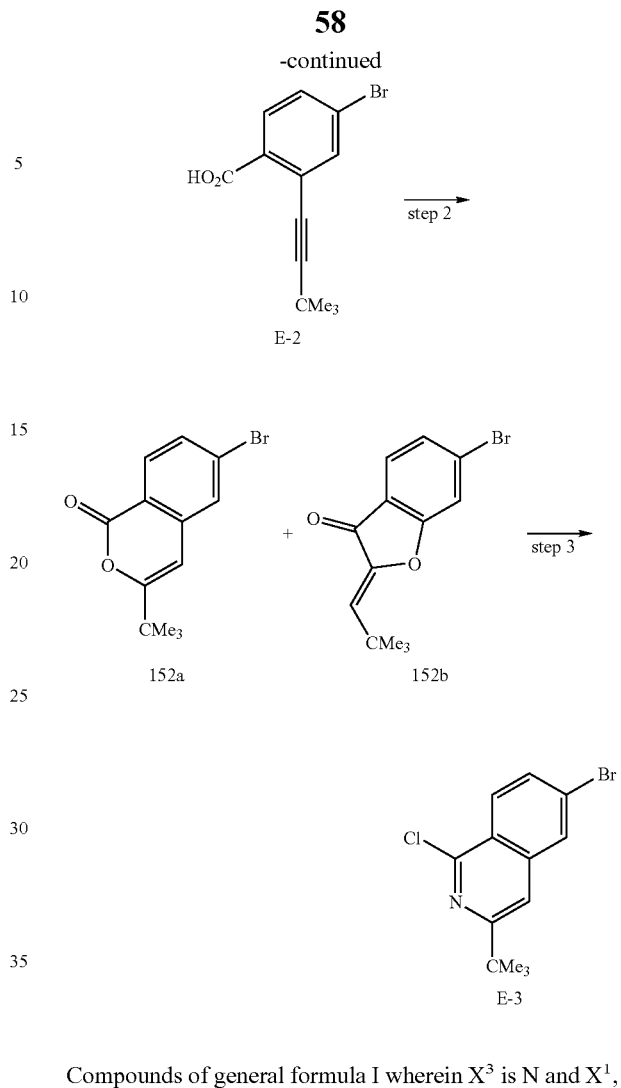

Compounds of general formula I wherein $X^3$ is N and $X^1$, $X^2$ and $X^4$ are $CR^6$ are prepared from E-3 by sequential palladium catalyzed couplings to introduce the $R^1$ and $R^3$ substituents using procedures analogous to those previously described. The conversion of E-1 to E-2 was carried out utilizing Heck palladium coupling protocols. Palladium-catalyzed intramolecular lactonization of the acetylenic acid produced a mixture of 6-endo-dig and 5-exo-dig products 152a and 152b, respectively. (H. Sashida and A. Kawamuki, *Synthesis* 1999 1145) Exposure of 152a to ammonia afforded the corresponding isoquinolone which was converted to E-3 with POCl₃. The preparation of E-1 has been described by G. C. Colossi et al. in WO2008/087057.

SCHEME F

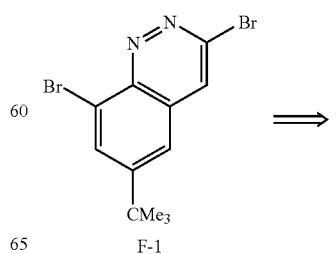

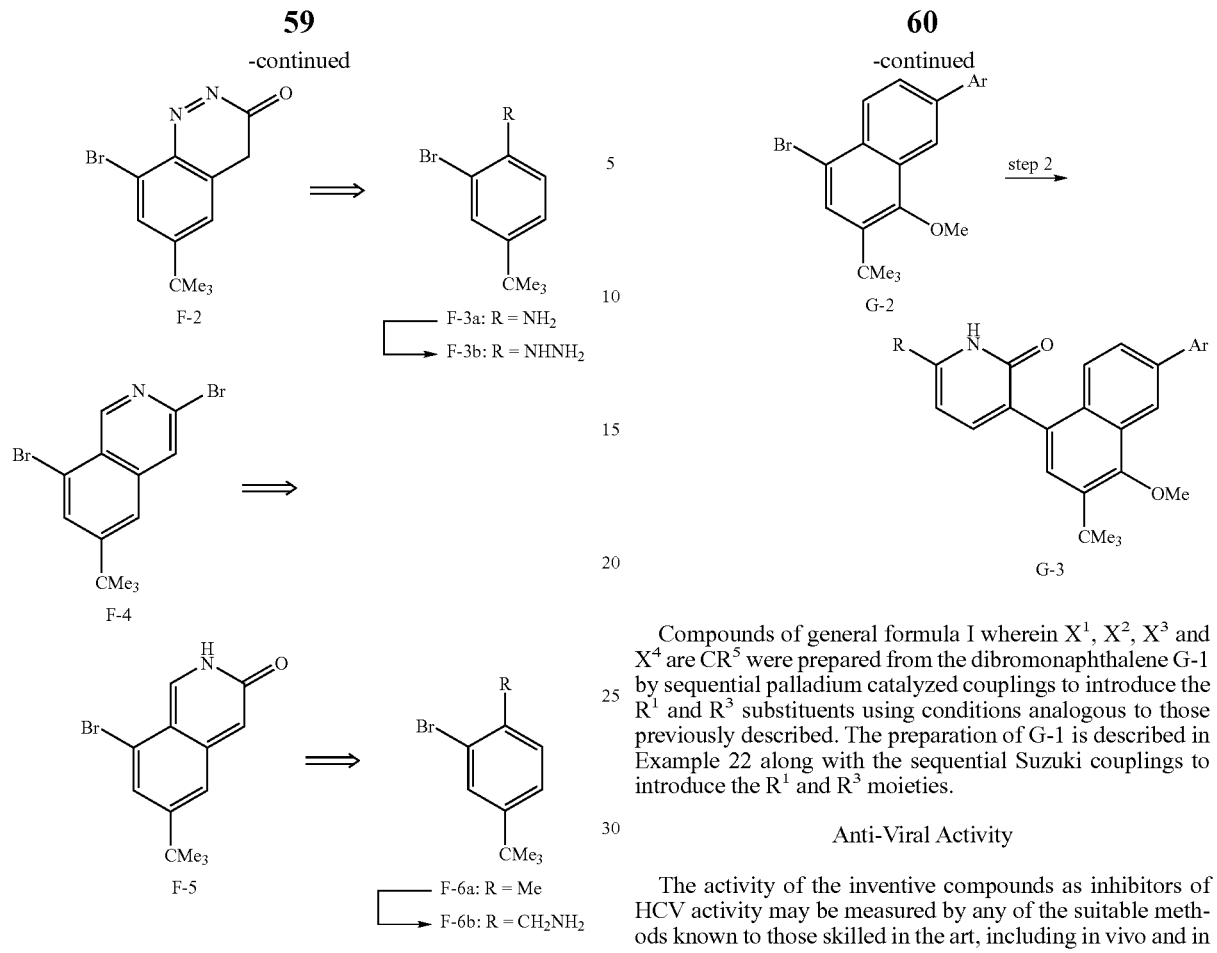

Compounds of general formula I wherein $X^3$ and $X^2$ are $CR^6$ and $X^1$ and $X^4$ are N (cinnoline derivatives) will be similarly prepared from F-1 by sequential palladium catalyzed couplings to introduce the $R^1$ and $R^3$ substituents using conditions analogous to those previously described. The conversion of F-2 to F-1 will be carried out with phosphorus oxybromide. F-2 will be prepared by treating F-3b with diethoxyacetyl chloride to acylate the hydrazine and undergo intra-molecular Friedel-Crafts acylation. Compounds of general formula I wherein $X^1$, $X^2$ and $X^3$ are $CR^6$ will be prepared analogously from F-4 which will be prepared from F-5. F-5 is prepared by an analogous intramolecular Friedel-Crafts acylation of F-6a. To avoid ambiguity it should be understood the arrows in SCHEME E ("⇒") represent retrosynthetic disconnections. (E. J. Corey Angew. Chem. Intl. Ed. Engl. 1991 30:455)

SCHEME G

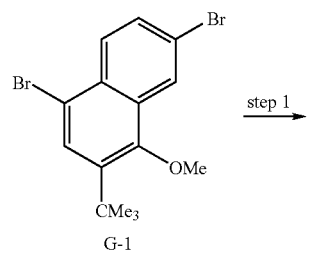

Compounds of general formula I wherein $X^1$, $X^2$, $X^3$ and $X^4$ are $CR^5$ were prepared from the dibromonaphthalene G-1 by sequential palladium catalyzed couplings to introduce the $R^1$ and $R^3$ substituents using conditions analogous to those previously described. The preparation of G-1 is described in Example 22 along with the sequential Suzuki couplings to introduce the $R^1$ and $R^3$ moieties.

Anti-Viral Activity

The activity of the inventive compounds as inhibitors of HCV activity may be measured by any of the suitable methods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 8. Cell-based replicon systems for HCV have been developed, in which the nonstructural proteins stably replicate subgenomic viral RNA in Huh7 cells (V. Lohmann et al., *Science* 1999 285:110 and K. J. Blight et al., *Science* 2000 290:1972). The cell-based replicon assay conditions used for compounds of the present invention are described in Example 42. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays.

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate. The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

A therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Example 1

N-{4-[6-tert-Butyl-2-methoxy-8-(2-oxo-1,2-dihydro-pyridin-3-yl)-quinolin-3-yl]-phenyl}-methane-sulfonamide (I-1)

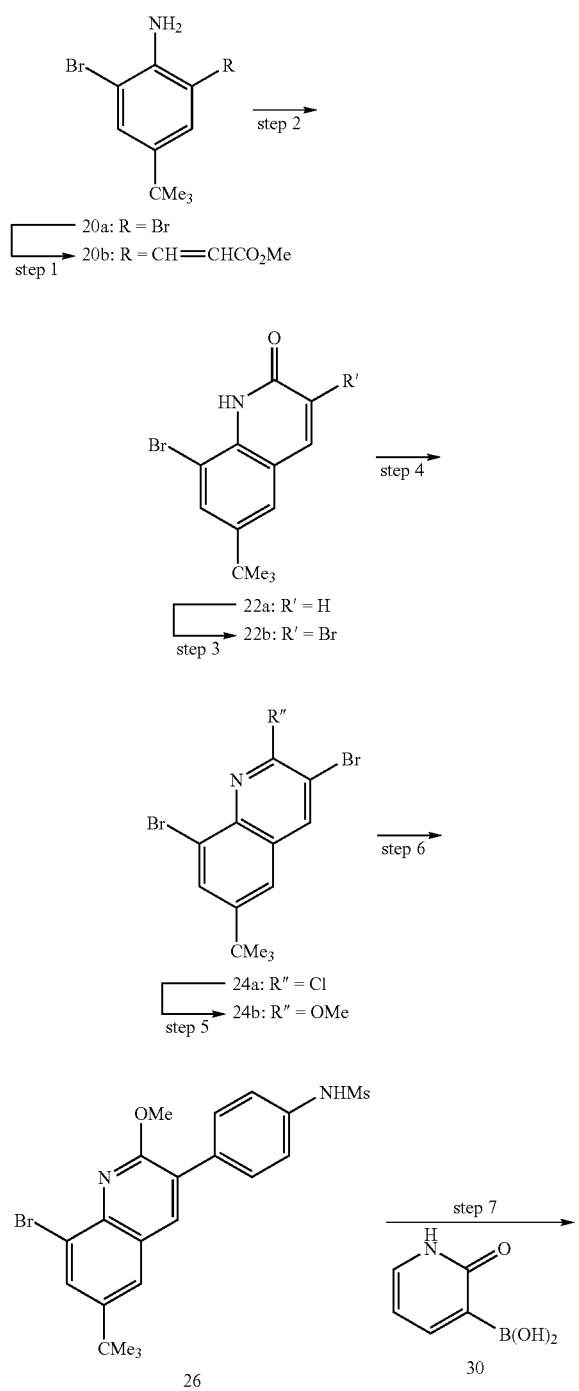

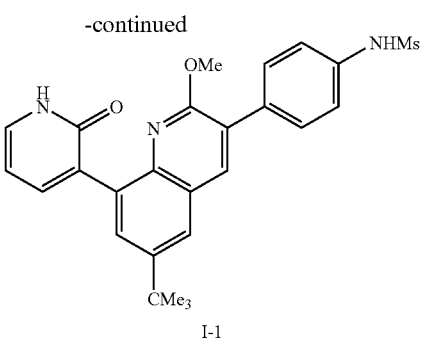

I-1 step 1—To a solution of 20a (10.0 g) and MeCN (200 mL) was added tri-(o-tolyl)phosphine (1.33 g), Pd(II)(OAc)$_2$ (0.730 g), TEA (6.8 mL) and methyl acrylate (2.35 mL). The reaction was stirred overnight at 100° C. The reaction was cooled and concentrated in vacuo. The crude product was purified by SiO$_2$ chromatography eluting with an EtOAc/hexane gradient (0% EtOAc from 0-5 min, 20% EtOAc from 5.5-15 min and 40% EtOAc from 15.5-30 min) to afford 3.02 g of 20b.

step 2—To a solution of 20b (6.73 g) and THF (150 mL) was added 6N HCl (150 mL) and the resulting solution was heated at 100° C. overnight. The solution was cooled and concentrated in vacuo. The reaction mixture was made basic with solid NaHCO$_3$ and thrice extracted with EtOAc (3×150 mL). The combined extracts were washed with brine, dried (Na$_2$SO$_4$), filtered and concentrated in vacuo. The crude product was purified by SiO$_2$ chromatography with the gradient described in step 1. The combined fractions were evaporated and triturated with Et$_2$O to afford 22a as an off white solid.

step 3—To a solution of 22a (0.500 g, 1.78 mmol) in DCM (10 mL) cooled to 0° C. (ice bath) was added Br$_2$ (90 µL, 1.78 mmol) slowly via syringe. The reaction was stirred for 3 h while warming to RT and then concentrated. The crude mixture was purified by SiO$_2$ chromatography eluting with an EtOAc/hexane gradient (stepwise 0, 20 and 40% EtOAc) to afford 0.273 g (42%) of 22b.

step 4—To a solution of 22b (0.273 g, 0.76 mmol) in MeCN (10 mL) was added POCl$_3$ (0.14 mL, 1.52 mmol). The reaction was heated at 100° C. for 8 h then concentrated and partitioned between EtOAc and water (25 mL/25 mL). The aqueous layer was separated and washed twice with EtOAc (2×25 mL). The combined extracts were washed with brine (25 mL), dried (Na$_2$SO$_4$), filtered, and concentrated to afford 0.287 g (100%) of 24a.

step 5—To a solution of 24a (0.242 g, 0.64 mmol) and DMF (2 mL) was added sodium methoxide (1.54 mL, 0.5M in MeOH, 0.769 mmol). The reaction was heated at 90° C. for 30 min, then concentrated and partitioned between EtOAc and H$_2$O (25 mL/25 mL). The aqueous layer was separated and extracted with EtOAc (2×25 mL). The combined organic layers were washed with brine (25 mL), dried (Na$_2$SO$_4$), filtered, and concentrated to afford 0.239 g (100%) of 24b.

step 6—To a vial containing 24b (0.100 g, 0.26 mmol) and MeOH/DCM (3 mL/1 mL) was added Na$_2$CO$_3$ (0.082 g, 0.78 mmol), 4-methylsulfonylamino-phenyl boronic acid (25, 0.056 g, 0.26 mmol) and Pd(PPh$_3$)$_4$ (0.030 g, 0.26 mmol). The reaction was irradiated in a microwave synthesizer at 115° C. for 30 min. The reaction was cooled, concentrated and partitioned between EtOAc/H$_2$O (25 mL/25 mL). The aqueous layer was separated and washed with EtOAc (2×25 mL). The combined organic extracts were washed with brine (25 mL), dried (Na$_2$SO$_4$), filtered and concentrated. The crude product was purified by SiO$_2$ flash eluting with an EtOAc/hexane gradient (stepwise 0% EtOAc from 0-5 min, 20% EtOAc from 5.5-15 min and 40% EtOAc from 15.5-30 min) to afford 0.068 g (57%) of 26.

step 7—To a solution of 26 (0.061 g, 0.13 mmol) dissolved in MeOH/DCM (3 mL/1 mL), was added Na$_2$CO$_3$ (0.041 g, 0.40 mmol), 30 (0.017 g, 0.16 mmol) and Pd(PPh$_3$)$_4$ (0.015 g, 0.013 mmol). The reaction was irradiated in a microwave synthesizer at 115° C. for 30 min. The reaction was cooled, concentrated and partitioned between EtOAc and H$_2$O (25 mL/25 mL). The aqueous layer was separated and washed EtOAc (2×25 mL). The combined extracts were washed with brine (25 mL), dried (Na$_2$SO$_4$), filtered and concentrated. The crude product was purified on a preparatory SiO$_2$ TLC plate developed sequentially with 40% EtOAc/hexane then dried and re-eluted with 100% EtOAc to afford 0.013 g (21%) of I-1.

Example 2

N-{4-[7-tert-Butyl-5-(5-fluoro-2-oxo-1,2-dihydro-pyridin-3-yl)-quinoxalin-2-yl]-phenyl}-methane-sulfonamide (I-2)

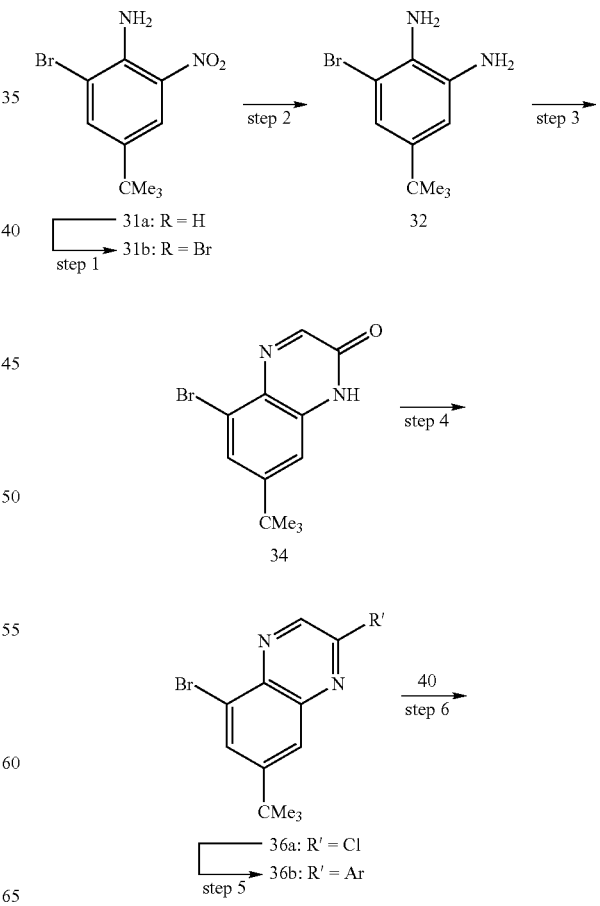

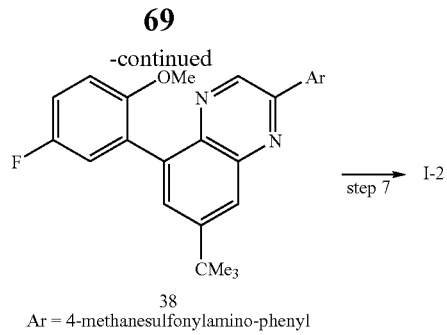

38
Ar = 4-methanesulfonylamino-phenyl step 1—To 4-tent-butyl-2-nitroaniline (31a, 5.0 g, 25.74 mmol) was added HOAc (40 mL). The reaction was heated to 50° C. until a clear orange-brown solution formed. The heating mantel was removed and bromine (1.46 mL, 28.32 mmol) was added carefully via syringe. The reaction was stirred 45 min more while cooling to RT then poured over ice (100 mL). The slurry was stirred with a glass rod and more solid precipitated out as the ice melted. The solid was collected on a glass frit and dried to afford 6.95 g (99%) of 31b.

step 2—To a solution of 31b (2.5 g, 9.15 mmol) in MeOH/H$_2$O (100 mL/25 mL) was added electrolytic iron (1.53 g, 27.46 mmol), and NH$_4$Cl (1.47 g, 27.46 mmol). The reaction was heated at reflux for 4 h then filtered through glass fiber filter paper on a Buchner funnel to remove the iron. The solid was rinsed with MeOH and the filtrate was concentrated and partitioned between EtOAc and H$_2$O (50 mL/50 mL). The aqueous layer was separated and washed with EtOAc (2×50 mL). The combined organic extracts were washed with brine (50 mL), dried (Na$_2$SO$_4$), filtered and concentrated to afford 2.23 g (100%) of 32.

step 3—To a solution of 32 (0.500 g, 1.8 mmol) in EtOH was added ethyl glyoxalate (50% by weight in toluene, 0.54 mL, 2.7 mmol). The reaction was heated at reflux overnight. More ethyl glyoxalate was added (0.54 mL, 2.7 mmol) and the reaction again heated at reflux overnight. The off-white precipitate was collected on a glass frit to afford 0.280 g (51%) of 34. (The other isomer also was present in the crude mixture, but not isolated).

step 4—To 34 (0.269 g, 0.96 mmol) suspended in MeCN (10 mL) was added POCl$_3$ (0.52 mL, 5.74 mmol). The reaction was heated at 100° C. for 3 h then concentrated and partitioned between EtOAc and H$_2$O (25 mL/25 mL). The aqueous layer was separated and washed with EtOAc (2×25 mL). The combined extracts were washed with brine (25 mL), dried (Na$_2$SO$_4$), filtered and concentrated to afford 0.286 g (quantitative) of 36a.

step 5—To a solution of 36a (0.050 g, 0.17 mmol in MeOH and DCM (3 mL/1 mL), was added Na$_2$CO$_3$ (0.053 g, 0.50 mmol), 4-methylsulfonylamino-phenyl boronic acid (0.028 g, 0.13 mmol) and Pd(PPh$_3$)$_4$ (0.019 g, 0.017 mmol). The reaction was irradiated in a microwave at 115° C. for 30 min. The reaction was cooled, concentrated and partitioned between EtOAc and H$_2$O (25 mL/25 mL). The aqueous layer was separated and washed with EtOAc (2×25 mL). The combined organic extracts were washed with brine (25 mL), dried (Na$_2$SO$_4$), filtered and concentrated. The crude product was purified by SiO$_2$ chromatography eluting with an EtOAc/hexane gradient (stepwise 0% EtOAc from 0-5 min, 20% EtOAc from 5.5-15 min and 40% EtOAc from 15.5-30 min) to afford 0.042 g (58%) of 36b.

step 6—To 36b (0.056 g, 0.13 mmol) dissolved in MeOH and DCM (3 mL/1 mL), was added Na$_2$CO$_3$ (0.041 g, 0.39 mmol), 5-fluoro-2-methoxy-3-(4,4,5,5-tetramethyl-[1,3,2]dioxaborolan-2-yl)-pyridine (40, 0.026 g, 0.16 mmol, CASRN 1083168-95-9) and Pd(PPh$_3$)$_4$ (0.015 g, 0.013 mmol). The reaction was irradiated in a microwave synthesizer at 115° C. for 30 min. The reaction was cooled, concentrated and partitioned between EtOAc and H$_2$O (25 mL/25 mL). The aqueous layer was separated and washed with EtOAc (2×25 mL). The combined organic extracts were washed with brine (25 mL), dried (Na$_2$SO$_4$), filtered and concentrated. The crude product was purified by SiO$_2$ chromatography eluting with an EtOAc/hexane gradient (stepwise 0% EtOAc from 0-5 min, 20% EtOAc from 5.5-15 min and 40% EtOAc from 15.5-30 min) to afford 0.061 g (100%) of 38.

step 7—To a solution of 38 (0.058 g, 0.148 mmol) in HOAc (2 mL) was added HBr (0.1 mL, 50% in water). The reaction was heated in a sealed tube in a sand bath at 70° C. over night. The reaction was cooled, poured over ice (25 mL) and aq. sat'd. NaHCO$_3$ (25 mL) was added slowly. The ice was allowed to melt and the resulting precipitate was collected on a glass frit to afford 0.034 g (61%) of I-2.

I-6 was prepared analogously except in step 6, 40 was replaced with 30. The crude product was adsorbed onto SiO$_2$ and purified by SiO$_2$ chromatography eluting with 10% MeOH/DCM.

Example 3

N-{1-[7-tert-Butyl-5-(2-oxo-1,2-dihydro-pyridin-3-yl)-quinoxalin-2-yl]-piperidin-4-yl}-methanesulfonamide (I-3)

step 1—To a solution of 36a (0.100 g, 0.33 mol) and N-piperidin-4-yl methane sulfonamide HCl salt (37, 0.143 g. 0.66 mmol, CASRN 70724-72-0) in DMF (2 mL) was added DIPEA (0.2 mL, 1.00 mmol). The reaction was irradiated in the microwave synthesizer at 140° C. for 30 min. The reaction mixture was cooled, concentrated and adsorbed onto SiO$_2$ and purified by SiO$_2$ chromatography eluting with 5% MeOH/DCM to afford 0.102 g (69%) of N-[1-(5-bromo-7-tert-butyl-quinoxalin-2-yl)-piperidin-4-yl]-methanesulfonamide (42).

step 2—To a solution of 42 (0.040 g, 0.10 mmol) in MeOH and DCM (3 mL/1 mL), was added Na$_2$CO$_3$ (0.029 g, 0.27 mmol), 30 (0.012 g, 0.11 mmol) and Pd(PPh$_3$)$_4$ (0.010 g, 0.010 mmol). The reaction was irradiated in a microwave synthesizer at 115° C. for 30 min. The reaction was cooled, concentrated and partitioned between EtOAc/H$_2$O (25 mL/25 mL). The aqueous layer was separated and washed EtOAc (2×25 mL). The combined organic extracts were washed with brine (25 mL), dried (Na$_2$SO$_4$), filtered and concentrated. The crude product was adsorbed onto SiO$_2$ and purified by SiO$_2$ chromatography eluting with 10% MeOH/DCM to afford 0.030 g (73%) of I-3.

I-5 was prepared analogously except in step 2, 30 was replaced with 40 and the demethylation was carried out as described in step 7 of Example 2. The crude product was purified by SiO$_2$ chromatography eluting with 10% MeOH/DCM.

Example 4

N—{(S)-1-[7-tert-Butyl-5-(5-fluoro-2-oxo-1,2-dihydro-pyridin-3-yl)-quinoxalin-2-yl]-pyrrolidin-3-ylmethyl}-methanesulfonamide (I-4)

step 1—To a solution of 36a (0.050 g, 0.13 mmol) and N—(S)-1-pyrrolidin-3-ylmethyl-methanesulfonamidemethane sulfonamide HCl salt (44, 0.053 g. 0.25 mmol, CASRN 1064048-61-8) in DMF (2 mL) was added DIPEA (00.1 mL, 0.50 mmol). The reaction was irradiated in the microwave synthesizer at 140° C. for 30 min. The reaction mixture was cooled, concentrated and adsorbed onto silica and purified by $SiO_2$ chromatography eluting with 5% MeOH/DCM to afford 0.050 g (68%) of N—[(S)-1-(5-bromo-7-tent-butyl-quinoxalin-2-yl)-pyrrolidin-3-ylmethyl] methanesulfonamide (46).

step 2—Suzuki cross-coupling of 46 and 40 was carried out as described in step 6 of Example 2. The crude product was purified by $SiO_2$ chromatography eluting with 5% MeOH/DCM (500 mL) followed by 10% MeOH/DCM (500 mL) to afforded 0.047 g (89%) of N-{(S)-1-[7-tert-butyl-5-(5-fluoro-2-methoxy-pyridin-3-yl)-quinoxalin-2-yl]-pyrrolidin-3-ylmethyl}-methanesulfonamide (48).

step 3—Demethylation of 48 was carried out as described in step 7 of Example 2. The crude product was purified on a preparative $SiO_2$ TLC plate by sequentially developing with 100% EtOAc, then 5% MeOH/DCM to afford I-4.

Example 5

N-{4-[7-tert-Butyl-5-(2-oxo-1,2-dihydro-pyridin-3-yl)-quinoxalin-2-yl]-phenyl}-methanesulfonamide (I-6)

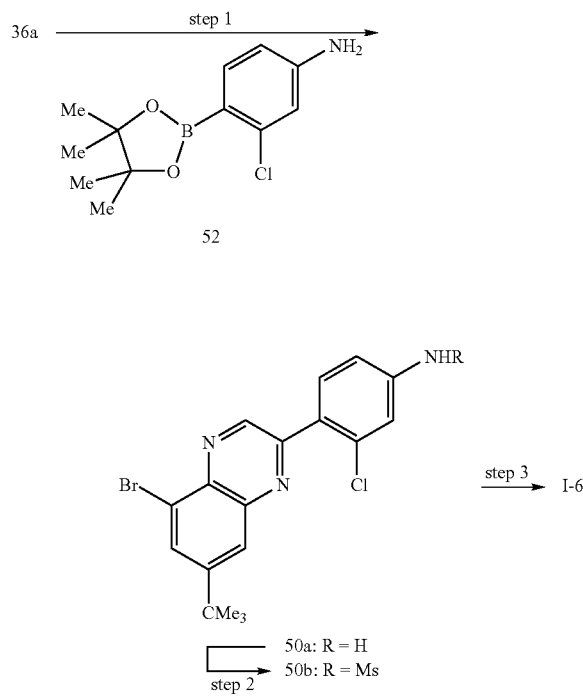

step 1—To 36a (0.216 g, 0.72 mmol), dissolved in MeOH and DCM (9 mL/3 mL) was added $Na_2CO_3$ (0.229 g, 2.2 mmol), 52 (0.146 g, 0.58 mmol, CASRN 877160-63-9) and $Pd(PPh_3)_4$ (0.083 g, 0.072 mmol). The reaction was irradiated in a microwave synthesizer at 115° C. for 30 min. The reaction was cooled, concentrated and partitioned between EtOAc and $H_2O$ (25 mL/25 mL). The aqueous layer was separated and washed with EtOAc (2×25 mL). The combined organic extracts were washed with brine (25 mL), dried ($Na_2SO_4$), filtered and concentrated. The crude product was purified by $SiO_2$ chromatography eluting with an EtOAc/hexane gradient (stepwise 0, 20 and 40% EtOAc) to afford 0.142 g (51%) of 50a.

step 2—To a solution of 50a (0.140 g, 0.36 mmol) and DCM was added pyridine (21 µL, 0.39 mmol) and solution was cooled to 0° C. (ice bath). Methane sulfonyl chloride (46 µL, 0.39 mmol) was added and after 15 min the ice bath was removed and the reaction warmed to RT and stirred for 3 h. The reaction was concentrated and partitioned between EtOAc (25 mL) and sat'd. aq. $NaHCO_3$ (25 mL). The aqueous layer was separated and washed with EtOAc (2×25 mL). The combined organic extracts were washed with brine (25 mL), dried ($Na_2SO_4$), filtered and concentrated. The crude product was purified by $SiO_2$ chromatography eluting with an EtOAc/hexane gradient (stepwise 0, 20 and 40% EtOAc) to afford 0.110 g (66%) of 50b.

step 3—A vial was charged with 50b (0.110 g, 0.24 mmol), MeOH and DCM (3 mL/1 mL) then $Na_2CO_3$ (0.075 g, 0.71 mmol), 30 (0.030 g, 0.28 mmol), and $Pd(PPh_3)_4$ (0.027 g, 0.024 mmol) were added. The reaction was irradiated in a microwave synthesizer at 115° C. for 30 min. The reaction was cooled, concentrated and partitioned between EtOAc and $H_2O$ (25 mL/25 mL). The aqueous layer was separated and washed EtOAc (2×25 mL). The combined organic extracts were washed with brine (25 mL), dried ($Na_2SO_4$), filtered and concentrated. The crude product was adsorbed onto $SiO_2$ and purified by $SiO_2$ chromatography eluting with 5% MeOH/DCM to afford 0.043 g (38%) of I-6.

I-8 was prepared analogously except in step 1, 52 was replaced with 4-amino-2-fluorophenyl boronic acid, pinacol ester (CASRN 819057-45-9).

I-9 was prepared analogously except in step 3, 30 was replaced with 2, 6 dimethoxy pyridine-3-boronic acid and the methyl ether was cleaved in accord with the procedure in step 7 of Example 1.

I-11 was prepared analogously except in step 1, 52 was replaced with 4-amino-2-fluorophenyl boronic acid, pinacol ester, in step 3, 30 was replaced with 2, 6 dimethoxy pyridine-3-boronic acid and the methyl ether was cleaved in accord with the procedure in step 7 of Example 2.

Example 6

N-{4-[7-tert-Butyl-3-methyl-5-(2-oxo-1,2-dihydro-pyridin-3-yl)-quinoxalin-2-yl]-phenyl}-methane-sulfonamide (I-10)

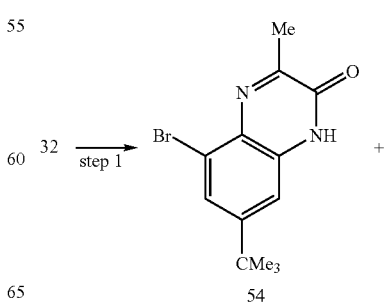

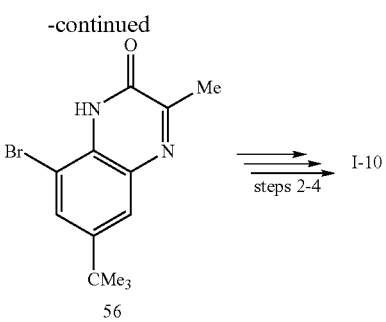

56 step 1—To a solution of 32 (2.5 g, 10.28 mmol) and EtOH (40 mL) was added pyruvic acid (0.86 mL, 12.34 mmol). The reaction was heated at 100° C. (reflux) and stirred for 2 h. The solution was cooled slowly to RT over night whereupon a precipitate formed. The crystals were collected on a glass frit but contained both isomers, and were therefore combined with the mother liquor and concentrated. The crude product was purified by SiO₂ chromatography eluting with 20% EtOAc/hexane to afford 0.694 g of 54 (23%) and 0.931 g of 56 (31%).

54 was converted I-10 in accord with steps 4-6 of example 2, except in step 6, 40 was replaced with 30 and step 7 was omitted. The crude product was adsorbed onto SiO₂ and purified by SiO₂ chromatography eluting with 5% MeOH/DCM to afford I-10.

Example 7

N-{4-[7-tert-Butyl-5-(6-methoxy-2-oxo-1,2-dihydro-pyridin-3-yl)-quinoxalin-2-yl]-3-chloro-phenyl}-methanesulfonamide (I-12)

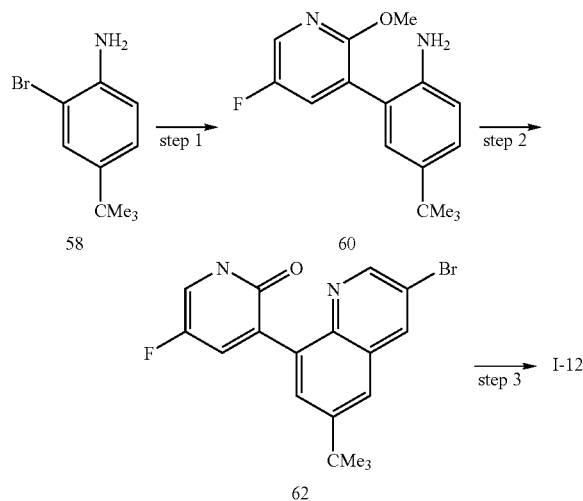

step 1—A microwave vial was charged with 58 (587 mg, 2.57 mmol), 5-fluoro-2-methoxy-pyridin-3-ylboronic acid (59, 660 mg, 3.86 mmol), Pd(PPh₃)₄ (148 mg, 0.12 mmol), Na₂CO₃ (818 mg, 7.8 mmol) and MeOH (0.7 mL)/DCM (3.5 mL), sealed and irradiated in a microwave synthesizer at 115° C. for 2 h. The reaction mixture was cooled to RT and diluted with EtOAc. The organic layer was washed with water, dried (MgSO₄), filtered and concentrated. The crude residue was purified by SiO₂ chromatography eluting with an EtOAc/hexane gradient to afford 460 mg (65%) of 60 as a brown oil.

step 2—A solution of Br₂ (191 mg, 1.6 mmol) in HOAc (5 mL) was added to a solution of α-bromoacrolein (230 mg, 1.71 mmol) in HOAc (5 mL) at RT until the appearance of a faint reddish color of excess bromine. After stirring at RT for 15 min, a solution of 60 (437 mg, 1.59 mmol) in HOAc (5 mL) was added. The reaction mixture was heated for 2 h at 100° C. The reaction mixture was carefully poured into a cold sat'd. aq. NaHCO₃, and then extracted with EtOAc. The organic layer was washed with brine, dried (MgSO₄), filtered and concentrated. The crude residue was purified by SiO₂ chromatography eluting with 1:1 hexanes/ethyl acetate to afford 260 mg (43%) of 62 as a brown oil step 3—A microwave vial was charged with 62 (60 mg, 0.16 mmol), 25 (52 mg, 0.241 mmol), Pd(PPh₃)₄ (10 mg, 0.008 mmol), and Na₂CO₃ (51 mg, 0.48 mmol) in a mixture of MeOH (0.1 mL) and DCM (0.5 mL), sealed and irradiated in a microwave synthesizer at 115° C. for 2 h. The reaction mixture was cooled to RT and diluted with EtOAc. The organic layer was washed with water, dried (MgSO₄), filtered and concentrated. The crude residue was purified by SiO₂ chromatography eluting with EtOAc to afford 32 mg (42%) of I-12 as a white off solid: MS (ES) (M+H)⁺=466.

Example 8

N-{1-[6-tert-Butyl-8-(5-fluoro-2-oxo-1,2-dihydro-pyridin-3-yl)-quinolin-3-yl]-piperidin-4-yl}-methanesulfonamide (I-13)

A vial was charged with 62 (70 mg, 0.187 mmol), 37 (44 mg, 0.205 mmol), Pd(OAc)₂ (4 mg, 0.018 mmol), NaO-tent-Bu (72 mg, 0.75 mmol) and P(tert-Bu)₃ (4 mg, 0.018 mmol) in toluene (3 mL), sealed and heated for 4 h at 100° C. The reaction mixture was cooled to RT and diluted with EtOAc. The organic layer was washed with water, dried (MgSO₄), filtered and concentrated. The crude residue was purified on a preparative SiO₂ TLC plate developed with 9:1 DCM/MeOH to afford 28 mg (32%) of I-13 as a brown oil: MS (ES) (M+H)⁺=473.

Example 9

N-{4-[6-tert-Butyl-5-methoxy-8-(2-oxo-1,2-dihydro-pyridin-3-yl)-quinolin-3-yl]-phenyl}-methanesulfonamide (I-14)

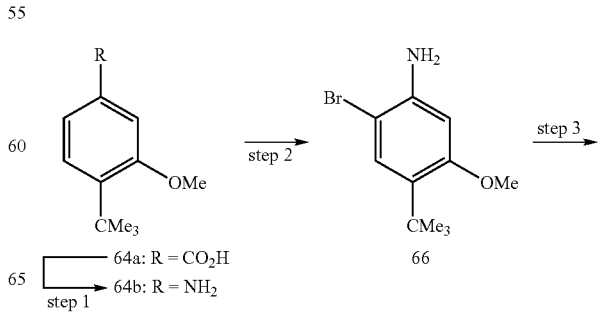

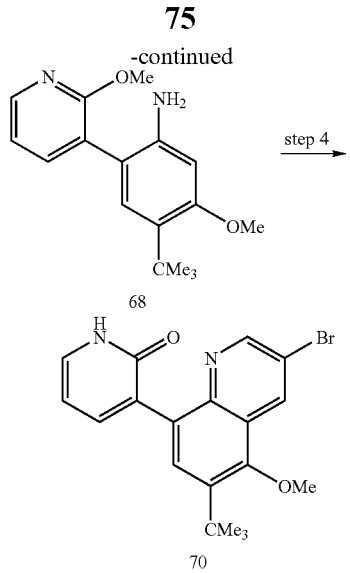

step 1—A mixture of 64a (6 g, 28.84 mmol, CASRN 79822-46-1), diphenylphosphoryl azide (8 g, 29.09 mmol), TEA (4.32 mL, 30.99 mmol) in tent-butanol (500 mL) was heated at reflux overnight. The reaction mixture was cooled to RT and the volatiles were evaporated. The crude material was treated with a 1:1 mixture of TFA and DCM (20 mL) at 0° C. After stirring at RT for 3 h, the reaction mixture was cooled to 0° C. and treated with 2M aq. NaOH. The reaction mixture was diluted with hexanes, separated, dried (MgSO$_4$), filtered and concentrated. The crude residue was purified by SiO$_2$ chromatography eluting with 1:4 EtOAc/hexane to afford 3.4 g (66%) of 64b as a brown oil.

step 2—NBS (498 mg, 2.7 mmol) was added to a solution of 64b (500 mg, 2.7 mmol) in MeCN (10 mL) at RT. The reaction mixture was stirred for 3 h at RT. The reaction mixture was diluted with EtOAc and washed with 1N NaOH, dried (MgSO$_4$), filtered and concentrated to afford 700 mg of 66 as brown oil.

step 3—A microwave vial was charged with 66 (700 mg, 2.71 mmol), 30 (612 mg, 4 mmol), Pd(PPh$_3$)$_4$ (231 mg, 0.2 mmol), and Na$_2$CO$_3$ (636 mg, 6 mmol), MeOH (1 mL) and DCM (9 mL), sealed and irradiated in a microwave synthesizer at 115° C. for 1 h. The reaction mixture was cooled to RT and diluted with EtOAc. The organic layer was washed with water, dried (MgSO$_4$), filtered and concentrated. The crude residue was purified by SiO$_2$ chromatography eluting with an EtOAc/hexane gradient to afford 420 mg (54%) of 68 as a brown oil.

step 4—A solution of Br$_2$ (191 mg, 1.6 mmol) in HOAc (5 mL) was added to a solution of α-bromoacrolein (230 mg, 1.71 mmol) in HOAc (5 mL) at RT until the faint reddish color of bromine persisted. After stirring at RT for 15 min, a solution of 68 (420 mg, 1.47 mmol) in HOAc (5 mL) was added. The reaction mixture was heated for 2 h at 100° C. The reaction mixture was carefully poured into a cold sat'd. aq. NaHCO$_3$, and then extracted with EtOAc. The organic layer was washed with brine, dried (MgSO$_4$), filtered and concentrated. The crude residue was purified by SiO$_2$ chromatography eluting with 1:1 hexanes/EtOAc to afford 150 mg (26%) of 70 as a brown oil: MS (ES) (M+H)$^+$=388.

step 5—A microwave vial was charged with 70 (150 mg, 0.387 mmol), 25 (125 mg, 0.581 mmol), Pd(PPh$_3$)$_4$ (45 mg, 0.038 mmol), Na$_2$CO$_3$ (123 mg, 1.16 mmol), MeOH (0.2 mL) and DCM (1.5 mL), sealed and irradiated in a microwave synthesizer at 115° C. for 1 h. The reaction mixture was cooled to RT and diluted with EtOAc. The organic layer was washed with water, dried (MgSO$_4$), filtered and concentrated. The crude residue was purified by SiO$_2$ chromatography eluting with a 95:5 DCM/MeOH to afford 40 mg (21%) of I-14 as a white off solid.

Example 10

N-{4-[6-tert-Butyl-8-(5-chloro-2-oxo-1,2-dihydro-pyridin-3-yl)-5-methoxy-quinolin-3-yl]-phenyl}-methanesulfonamide (I-15)

NCS (15 mg, 0.112 mmol) was added to a solution of I-14 (48 mg, 0.1 mmol) in MeCN (5 mL) and DMF (2 mL) warmed to 70° C. The reaction mixture was stirred at 70° C. for 5 h, then cooled to RT and diluted with EtOAc. The organic layer was washed with H$_2$O, dried (MgSO$_4$), filtered and concentrated. The crude residue was purified by SiO$_2$ chromatography eluting with an EtOAc/hexane gradient to afford 25 mg (49%) of I-15 as a white solid.

Example 11

N-{1-[6-tert-Butyl-5-methoxy-8-(2-oxo-1,2-dihydro-pyridin-3-yl)-quinolin-3-yl]-azetidin-3-ylmethyl}-methanesulfonamide (I-19) & N-{1-[6-tert-Butyl-4-chloro-5-methoxy-8-(2-oxo-1,2-dihydro-pyridin-3-yl)-quinolin-3-yl]-azetidin-3-ylmethyl}-methanesulfonamide (I-22)

step 1—A vial was charged with 70 (301 mg, 0.77 mmol), N-azetidin-3-ylmethyl-methanesulfonamide hydrochloride (200 mg, 0.934 mmol), Pd(OAc)$_2$ (18 mg, 0.08 mmol), NaO-tent-Bu (298 mg, 3.1 mmol), and P(tert-Bu)$_3$ (16 mg, 0.079 mmol) in toluene (3 mL), sealed and heated for 20 h at 100° C. The reaction mixture was cooled to RT and diluted with EtOAc. The organic layer was washed with sat'd. aq. NaHCO$_3$, dried (MgSO$_4$), filtered and concentrated. The crude residue was purified by SiO$_2$ chromatography eluting with an DCM/MeOH gradient to afford 95 mg (26%) of I-19 as a white off solid.

step 2—NCS (14 mg, 0.105 mmol) was added to a solution of I-19 (45 mg, 0.095 mmol) in MeCN (5 mL) at 70° C. The reaction mixture was stirred at 70° C. for 2 h. The reaction mixture was cooled to RT and diluted with EtOAc. The organic layer was washed with 1N NaOH, dried (MgSO$_4$), filtered and concentrated. The crude residue was purified on a preparative SiO$_2$ TLC plate developed with 9:1 DCM/MeOH to afford 13 mg (27%) of I-22 as a semi solid.

Example 12

N—{(S)-1-[6-tert-Butyl-5-methoxy-8-(2-oxo-1,2-dihydro-pyridin-3-yl)-quinolin-3-yl]-pyrrolidin-3-ylmethyl}-methanesulfonamide (I-18)

N-pyrrolidin-3-ylmethyl-methanesulfonamide (72)—TEA (1.05 mL, 7.5 mmol) was added to a solution of (R)-3-(aminomethyl)-1-N-Boc-pyrrolidine (1 g, 5 mmol) in DCM (25 mL) at 0° C. Methanesulfonyl chloride (0.43 mL, 5.5 mmol) was then added. After stirring at 0° C. for 2 h, the reaction mixture was diluted with water. The organic phase was separated, dried (MgSO$_4$), filtered and concentrated. The crude material was treated with 1M HCl in MeOH (25 mL) at RT and stirred at RT for 20 h. The volatiles were removed under reduced pressure to afford 0.95 g of 72 as a white solid.

step 1—A vial was charged with 70 (301 mg, 0.77 mmol), 72 (200 mg, 0.778 mmol), Pd(OAc)$_2$ (18 mg, 0.08 mmol), NaO-tert-Bu (298 mg, 3.1 mmol), and P(tert-Bu)$_3$ (16 mg, 0.079 mmol) in toluene (3 mL), sealed and heated for 20 h at 100° C. The reaction mixture was cooled to RT and diluted with EtOAc. The organic layer was washed with sat'd. aq. NaHCO$_3$, dried (MgSO$_4$), filtered and concentrated. The crude residue was purified by SiO$_2$ chromatography eluting with 9:1 DCM/MeOH to afford 60 mg (16%) of I-18 and 60 mg (25%) of 3-(6-tert-butyl-5-methoxy-quinolin-8-yl)-1H-pyridin-2-one [(M+H)$^+$=309] as white solids.

Example 13

N-{4-[6-tert-Butyl-8-(2,4-dioxo-3,4-dihydro-2H-pyrimidin-1-yl)-5-methoxy-quinolin-3-yl]-phenyl}-methanesulfonamide (I-21)

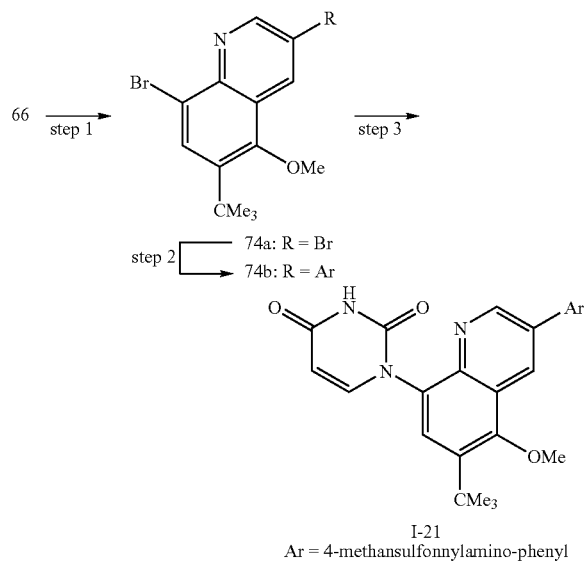

I-21
Ar = 4-methansulfonnylamino-phenyl step 1—A solution of Br$_2$ (126 mg, 1.05 mmol) in HOAc (5 mL) was added to a solution of α-bromoacrolein (148 mg, 1.1 mmol) in HOAc (5 mL) at RT until a faint reddish color of bromine persists. After stirring at RT for 15 min, a solution of 66 (260 mg, 1.01 mmol) in HOAc (5 mL) was added. The reaction mixture was heated for 4 h at 100° C. The reaction mixture was carefully poured into a cold sat'd. aq. NaHCO$_3$, and then extracted with EtOAc. The organic layer was washed with brine, dried (MgSO$_4$), filtered and concentrated. The crude residue was purified by SiO$_2$ chromatography eluting with a hexane/EtOAc gradient to afford 170 mg (45%) of 74a as a brown oil.

step 2—A vial was charged with 74a (850 mg, 2.27 mmol), 25 (539 mg, 2.5 mmol), Pd(PPh$_3$)$_4$ (263 mg, 0.227 mmol), Na$_2$CO$_3$ (725 mg, 6.83 mmol), MeOH (8 mL) and DCM (5 mL), sealed and irradiated in a microwave synthesizer at 120° C. for 1 h. The reaction mixture was cooled to RT and diluted with EtOAc. The organic layer was washed with water, dried (MgSO$_4$), filtered and concentrated. The crude residue was purified by SiO$_2$ chromatography eluting with EtOAc to afford 600 mg (57%) of 74b as a white off solid: MS (ES) (M+H)$^+$=464.

step 3—A vial was charged with 74b (200 mg, 0.431 mmol), uracil (72 mg, 0.642 mmol), N-(2-cyanophenyl)picolinamide (19 mg, 0.085 mmol), CuI (8 mg, 0.042 mmol), K$_3$PO$_4$ (183 mg, 0.86 mmol), DCM and MeOH and then degassed. DMSO (1.5 mL) was added. The vial was sealed and irradiated in a microwave synthesizer at 150° C. for 5 h. The reaction mixture was cooled to RT and diluted with EtOAc. The organic layer was washed with 1N NaHSO$_4$, dried (MgSO$_4$), filtered and concentrated. The crude residue was purified by SiO$_2$ chromatography eluting with EtOAc to afford 17 mg (8%) of I-21 as a semi solid.

N—{(S)-1-[6-tert-Butyl-5-methoxy-8-(6-methoxy-2-oxo-1,2-dihydro-pyridin-3-yl)-quinolin-3-yl]-pyrrolidin-3-ylmethyl}-methanesulfonamide (I-55) is prepared from 74a employing a Suzuki coupling with 115 and demethylation in accord with the procedure in steps 2 and 3 of example 24.

Example 14

N-{4-[6-tert-Butyl-8-(2,4-dioxo-1,2,3,4-tetrahydro-pyrimidin-5-yl)-5-methoxy-quinolin-3-yl]-phenyl}-methanesulfonamide (I-25)

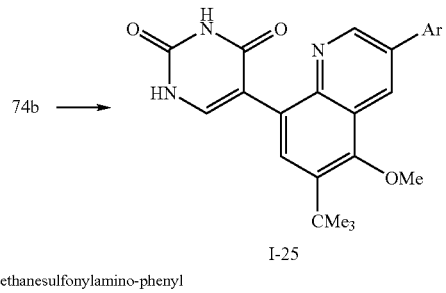

I-25
Ar = 4-methanesulfonylamino-phenyl

A 5 mL microwave vial was charged with 74b (98.7 mg, 0.213 mmol), 2,4-dioxo-1,2,3,4-tetrahydro-pyrimidin-5-yl boronic acid (67.9 mg, 0.436 mmol, CASRN 70523-22-7), Na$_2$CO$_3$ (119.8 mg, 1.13 mmol), and Pd(PPh$_3$)$_4$ (27.8 mg, 0.024 mmol), MeOH (1.6 mL) and DCM (0.4 mL), sealed and irradiated in a microwave synthesizer at 115° C. for 60 min. After cooling to RT the reaction mixture was poured into sat'd. aq. NaHCO$_3$ (30 mL) and extracted with EtOAc (3×20 mL). The combined extracts were washed with sat'd. aq. NaHCO$_3$ (2×40 mL), brine (40 mL), dried (Na$_2$SO$_4$), filtered and concentrated. The crude product was purified by SiO$_2$ chromatography eluting with a MeOH/DCM gradient (2 to 10% MeOH) to afford 15 mg (14%) of I-25 as a light yellow solid.

I-23 was prepared analogously except 2,4-dioxo-1,2,3,4-tetrahydro-pyrimidin-5-yl boronic acid was replaced with 59 and the methyl ether was cleaved in accord with the procedure in step 7 of example 2. The crude product was purified by SiO$_2$ chromatography eluting with a MeOH/DCM gradient (2 to 5% MeOH) to afford I-23 as an off-white solid.

I-24 was prepared analogously except 2,4-dioxo-1,2,3,4-tetrahydro-pyrimidin-5-yl boronic acid was replaced with 2-methoxy-6-methyl-pyridin-3-yl boronic acid (CASRN 1000802-75-4) and the methyl ether was cleaved in accord with the procedure in step 7 of example 2. The crude product precipitated as yellow crystals.

I-26 was prepared analogously except 2,4-dioxo-1,2,3,4-tetrahydro-pyrimidin-5-yl boronic acid was replaced with 3-fluoro-pyridin-4-yl boronic acid. The crude product precipitated as yellow crystals. The crude product was purified by SiO$_2$ chromatography eluting with a MeOH/DCM gradient (2 to 5% MeOH) to afford I-26 as an off-white solid.

I-34 was prepared analogously except 2,4-dioxo-1,2,3,4-tetrahydro-pyrimidin-5-ylboronic acid was replaced with 115 and the methyl ether was cleaved in accord with the procedure in step 7 of example 2.

Example 15

N-{4-[6-tert-Butyl-5-methoxy-8-(2-oxo-tetrahydro-pyrimidin-1-yl)-quinolin-3-yl]-phenyl}-methane-sulfonamide (I-27)

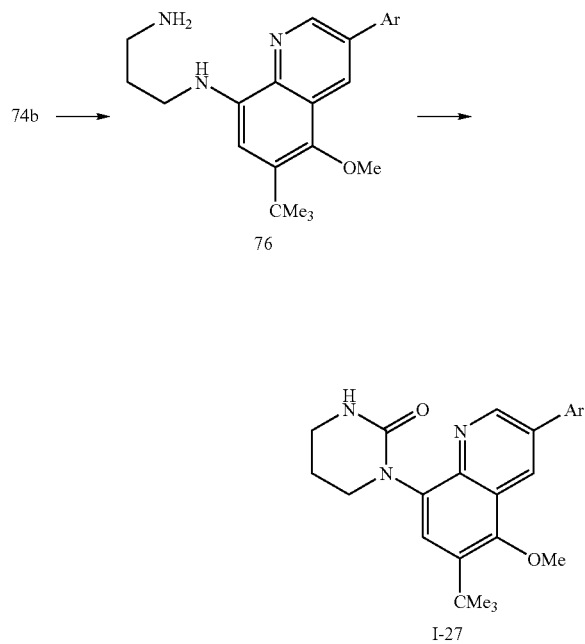

Ar = 4-methansulfonylamino-phenyl

A vial was charged with 74b (80 mg, 0.172 mmol), 1,3-propanediamine (300 μL), D,L-proline (8 mg, 0.069 mmol), CuI (8 mg, 0.036 mmol), K$_2$CO$_3$ (96 mg, 0.695 mmol) and degassed DMSO (0.5 mL) was added. The reaction mixture was heated for 48 h at 150° C. The reaction mixture was cooled to RT and diluted with EtOAc. The organic layer was washed with water, dried (MgSO$_4$), filtered and concentrated. The crude residue dissolved in THF (5 mL) and treated with carbonyl diimidazole (350 mg). After stirring at RT for 4 h, the reaction was diluted with EtOAc. The organic layer was washed with water, dried (MgSO$_4$), filtered and concentrated. The amine was not completely cyclized. Thus, the material was dissolved in dioxane (15 mL) and irradiated in a microwave reactor at 150° C. for 30 min. The reaction mixture was cooled to RT and concentrated. The crude residue was purified on a preparative SiO$_2$ TLC plate developed with 95:5 DCM/MeOH to afford 15 mg (18%) of I-27 as a light yellow solid.

Example 16

N-{4-[6-tert-Butyl-5-methoxy-8-(3-oxo-2,3-dihydro-pyridazin-4-yl)-quinolin-3-yl]-phenyl}-methane-sulfonamide (76)

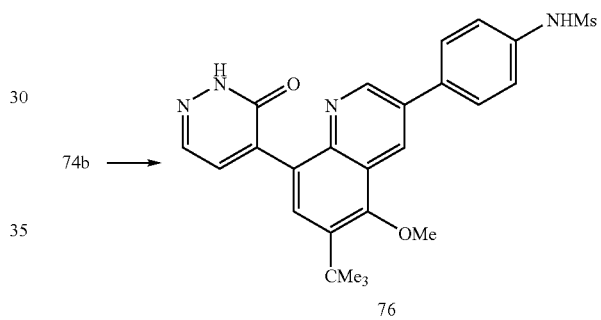

B-(2,3-dihydro-3-oxo-4-pyridazinyl)-boronic acid (78): step a—A 1 L round-bottom flask was charged with 4-chloro-5-hydrazinyl-3(2H)-pyridazinone (8.0 g, 50 mmol, CASRN 6959-56-4), CuSO$_4$.5H$_2$O (26.12 g, 10.5 mmol) and H$_2$O (300 mL) and the mixture was stirred and heated at reflux overnight. The reaction was cooled to 0° C. and an aq. solution of NaOH was added until the pH was 4. The aqueous layer was thrice extracted with EtOAc (500 mL each). The combined extracts were dried (Na$_2$SO$_4$), filtered and evaporated. The remaining aqueous phase was adjusted to pH of 2 with 37% HCl and the solution extracted six times with EtOAc. The extracts were combined, dried (Na$_2$SO$_4$), filtered and evaporated to afford 4.75 g of 4-chloro-2H-pyridazin-3-one (75)

step b—A microwave vial was charged with 75 (0.400 g, 3 mmol), bis-(pinacolato)diboron (0.934 g, 4 mmol), dicyclohexyl[2',4',6'-tris(1-methylethyl)[1,1'-biphenyl]-2-yl]-phosphine (X-Phos, 0.058 g, 0.12 mmol), Pd$_2$(dba)$_3$ (0.056 g, 0.061 mmol) and KOAc (0.902 g, 9 mmol) and the flask was evacuated and back-filled with Ar and sealed. Dioxane (6 mL) was added and the reaction heated at 110° C. overnight. The reaction mixture was cooled to RT and extracted with EtOAc (120 mL). The organic extract was washed sequentially with H$_2$O (10 mL) and brine (10 mL), dried (Na$_2$SO$_4$), filtered and evaporated. The crude product was triturated with Et$_2$O to afford 0.217 g of 78.

Palladium catalyzed coupling of 74b and 78 is carried out as described in Example 14 to afford 76.

Example 17

N-{4-[6-tert-Butyl-8-(2,4-dioxo-tetrahydro-pyrimidin-1-yl)-5-methoxy-quinolin-3-yl]-phenyl}-methanesulfonamide (I-28)

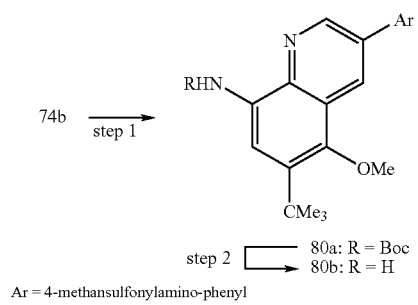

Ar = 4-methansulfonylamino-phenyl step 1—A dried microwave tube was purged with argon and charged with Pd$_2$(dba)$_3$·CHCl$_3$ (0.11 g, 0.106 mmol), 2-di-tert-butylphosphino-2',4',6'-tri-isopropyl-1,1'-biphenyl (0.136 g, 0.321 mmol), sodium tert-butoxide (0.10 g, 1.041 mmol), 74b (0.33 g, 0.712 mmol), and tert-butylcarbamate (0.10 g, 0.855 mmol). Toluene (3.5 mL) as added and the resulting mixture was degassed by bubbling argon through the solution for 1 h. The tube was capped and the reaction mixture was stirred at RT for 2 d then diluted with EtOAc and washed with sat'd. aq. NH$_4$Cl. The aqueous layer was back extracted once with EtOAc. The combined organic layers were dried (Na$_2$SO$_4$), filtered, and evaporated. The residue was purified by SiO$_2$ flash chromatography eluting with hexanes/EtOAc (7.5/2.5) to afford 0.315 g (89% yield) of 80a.

step 2—HCl (6 mL, 4M solution in dioxane) was added at RT to a solution of 80a (0.315 g, 0.631 mmol) in DCM (5 mL). The resulting mixture was stirred at RT for 4 h then evaporated. The residue was partitioned between sat'd. aq. NaHCO$_3$ and EtOAc. The aqueous layer was back extracted twice with EtOAc. The combined organic layers were dried (Na$_2$SO$_4$), filtered, and evaporated to afford 80b which was used in the next step without purification.

step 3—Acrylic acid (0.09 mL, 1.304 mmol) was added at RT in 3 portions (0.02, 0.02, 0.05 mL) to a solution of 80b (theoretically 0.631 mmol) in toluene (2.5 mL). After the first addition, the reaction mixture was stirred at 120° C. for 2 h. After the second addition, the reaction mixture was stirred at 120° C. for 1 h and after the third addition, the reaction mixture was stirred at 120° C. overnight. The reaction mixture was cooled to RT and evaporated. The residue was taken in glacial HOAc (2 mL) and urea (0.095 g, 1.576 mmol) was added. The reaction mixture was stirred at 120° C. for 6 h then cooled to RT and evaporated. The dark brown residue was partitioned between EOAc and sat'd. aq. NaHCO$_3$. The aqueous layer was back extracted twice with EtOAc. The combined organic layers were dried (Na$_2$SO$_4$), filtered, and evaporated. The residue was adsorbed onto SiO$_2$ and purified by SiO$_2$ chromatography (12 g SiO$_2$) eluting with a DCM/EtOAc gradient (50 to 80% EtOAc) to give 0.07 g of I-28 as greenish gray powder. The powder was taken into a minimal amount of DCM and the insoluble material was filtered and rinsed with a small amount of DCM to give 0.04 g of I-28 as a light gray powder.

Example 18

N-{4-[8-(2,4-Dioxo-tetrahydro-pyrimidin-1-yl)-5-methoxy-6-trifluoromethyl-quinolin-3-yl]-phenyl}-methanesulfonamide (I-29)

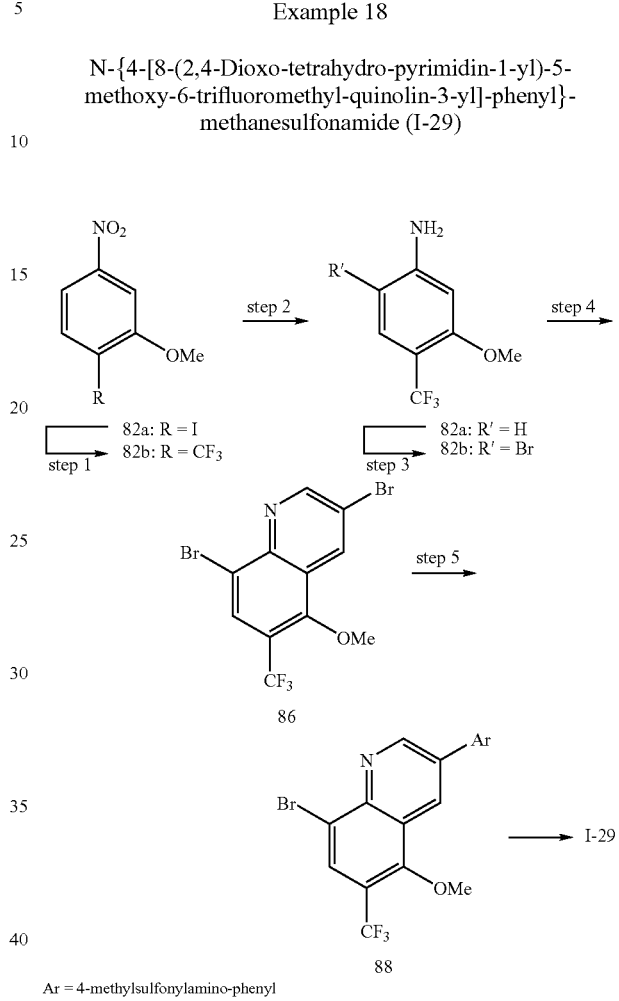

Ar = 4-methylsulfonylamino-phenyl step 1—A mixture of Cu(I) (10.03 g) and CsF (21.40 g) was finely ground in a mortar while in a glove bag under nitrogen atmosphere to afford a free-flowing powder and transferred to an oven dried 250 mL round bottom flask fitted with a stir bar and septum. The flask was then charged with 2-iodo-5-nitroanisole (15.17 g) and sulfolane (30 mL) and stirred rapidly at 45° C. To the mixture was added dropwise over 4 h using a syringe pump trimethyl(trifluoromethyl)silane (20 mL) and the resulting mixture stirred at RT overnight. The reaction was diluted with EtOAc (500 mL) and stirred in some CELITE® 512. The reaction mixture was filtered though a pad of CELITE. The filtrate was diluted to 1 L with EtOAc and washed with 1 L of 10% aqueous NH$_4$OH, 1 L of 1.0M HCl and 500 mL of brine. The organic phase was dried (MgSO$_4$), filtered and concentrated in vacuo. The amber residue was diluted with DCM and purified by flash chromatography (770 g Supelco VersaPak™ SiO$_2$ column) and eluted with a DCM/hexane gradient (0 to 40% DCM) in 10 column volumes to afford 8.61 g of 82b as a yellow crystalline solid.

step 2—A 500 mL Parr hydrogenation flask was charged with 82b (8.60 g) and 10% Pd/C (1.75 g). The flask was purged with nitrogen and EtOH (150 mL) was added carefully. The mixture was purged with nitrogen for 5 min. The reduction was carried out using a Parr shaker under 57 psi of hydrogen pressure at 55° for 18 h. The reaction mixture was cooled and the catalyst filtered through a glass-fiber filter and washed through with IPA. The solvent was removed in vacuo. The crude was diluted with DCM purified by flash chromatography (200 g Analogix™ SF65 SiO$_2$ column) and eluted with an EtOAc/hexane gradient (0 to 40% EtOAc) over 15 column volumes to afford 7.18 g of 84a as a waxy off-white solid.

step 3—A 100 mL round bottom flask fitted with a stir bar and septum was charged with 84a (3.01) g and maintained nitrogen atmosphere. To the flask was added anhydrous dioxane (25 mL) and HOAc (7.5 mL). The solution was stirred rapidly in an ice bath and a solution of bromine and dioxane (20 mL, 0.135 g Br$_2$/mL) was added dropwise over 30 min using a syringe pump. A beige precipitate formed and the mixture thickened. The ice bath was removed and the reaction mixture stirred at RT for 1 h. The reaction mixture was poured into a mixture of 1.0 M NaOH (150 mL) and 2.0 M Na$_2$CO$_3$ (150 mL) and extracted with DCM (3×100 mL). The combined extracts were washed sequentially with 0.5 M Na$_2$CO$_3$ (150 mL) and brine (150 mL), dried (Na$_2$SO$_4$), filtered and concentrated in vacuo. The resulting pale yellow liquid slowly solidified and darkened to afford 84b (4.10 g) black crystalline solid.

step 4—A 100 mL round bottom flask fitted with a stir bar and septum was charged with HOAc (50 mL) then 2-bromoacrolein (1.91 g) was added. To the stirred mixture was added dropwise Br$_2$ dropwise until the red color persisted (ca. 720 μL). To this solution was added a solution of 84b (3.48 g) HOAc (15 mL). A thick precipitate formed and stirring was continued at 100° C. for 1 h. The precipitate dissolved to give a clear dark amber solution after 10 min. A second precipitate formed after 30 min. The reaction was cooled to RT and poured into a stirred ice cold solution of 2.0 M aq. NaOH (550 mL). To the mixture was slowly added 2.0 M aq. Na$_2$CO$_3$ [vigorous foaming] until the solution was pH ca. 8 and the resulting solution extracted with DCM (3×250 mL). The combined extracts were washed brine (500 mL), dried (Na$_2$SO$_4$), filtered and concentrated in vacuo to afford a dark resin that was purified by flash chromatography (385 g Supelco VersaPak™ SiO$_2$ column) and eluted with a DCM/hexane gradient (0 to 100% DCM) over 10 column volumes. LC-MS and TLC analysis indicated the compound was not pure. The product was re-chromatographed (100 g Supelco VersaPak® SiO$_2$ column) and eluted with an EtOAc/hexane gradient (0 to 100% EtOAc) over 30 column volumes to afford 938 mg of 86 as an off-white solid.

step 5—A 20 mL vial fitted with a stir bar and septum cap was charged 86 (850 mg) and N-4-(4,4,5,5-tetramethyl-1,3,2-dioxaborolan-2-yl)phenylmethanesulfonamide (661 mg, CASRN 616880-14-9), dioxane (10 mL) and an aqueous solution of Cs$_2$CO$_3$ (2.3 mL, of Cs$_2$CO$_3$ 0.956 g/mL). The reaction mixture was sparged with nitrogen for 10 min then (dppf)PdCl$_2$.DCM (74 mg) was added. The reaction was sparged with nitrogen for 5 min, sealed and stirred at 65° for 110 min. The reaction was cooled and poured into DCM (100 mL) and 0.5 M aq. Na$_2$CO$_3$ (50 mL). The phases were separated and washed sequentially with H$_2$O (50 mL) and brine (50 mL) dried (MgSO$_4$), filtered and concentrated in vacuo. The product was purified by flash chromatography (100 g Supelco VersaPak® SiO$_2$ column) eluting with an EtOAc/DCM gradient (0 to 100% EtOAc) over 15 column volumes to afford 538 mg of 88 as a light amber solid.

The conversion of 88 to I-29 was carried out in accord with steps 1 to 3 of example 17.

N-{4-[5-Methoxy-8-(6-methyl-2-oxo-1,2-dihydro-pyridin-3-yl)-6-trifluoromethyl-quinolin-3-yl]-phenyl}-methanesulfonamidehydrobromide (I-49) was prepared analogously except in step 5, N-4-(4,4,5,5-tetramethyl-1,3,2-dioxaborolan-2-yl)phenylmethanesulfonamide was replaced with 2-methoxy-6-methyl-pyridin-3yl boronic acid. Demethylation of the pyridinyl O-methyl ether can be carried out in accord with the procedure in step 7 of example 2.

N-{4-[5-Methoxy-8-(6-methoxy-2-oxo-1,2-dihydro-pyridin-3-yl)-6-trifluoromethyl-quinolin-3-yl]-phenyl}-methanesulfonamide was prepared analogously except in step 5, N-4-(4,4,5,5-tetramethyl-1,3,2-dioxaborolan-2-yl)phenylmethanesulfonamide was replaced with 115. Demethylation of the pyridinyl O-methyl ether can be carried out in accord with the procedure in step 7 of example 2.

N-{4-[8-(2,4-Dioxo-3,4-dihydro-2H-pyrimidin-1-yl)-5-methoxy-6-trifluoromethyl-quinolin-3-yl]-phenyl}-methanesulfonamide (I-51) was prepared from 88 utilizing the procedure in step 3 of example 13.

Example 19

N—{(S)-3-[6-tert-Butyl-8-(dioxo-tetrahydro-pyrimidin-1-yl)-5-methoxy-quinolin-3-yl]-cyclopentyl}-methanesulfonamide (I-31)

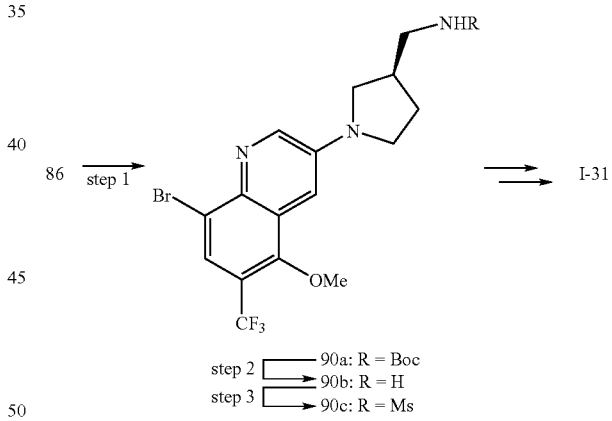

step 1—A dried microwave tube was purged with argon and charged with 86 (0.47 g, 1.26 mmol), (S)-1-pyrrolidin-3-ylmethyl-carbamic acid tent-butyl ester (0.38 g, 1.897 mmol, CASRN 173340-26-6), sodium tert-butoxide (0.18 g, 1.873 mmol), xantphos (0.146 g, 0.252 mmol), and Pd$_2$(dba)$_3$ (0) (0.115 g, 0.126 mmol). The tube was purged with argon, and 1 mL of toluene was added. The reaction mixture was degassed for 15 min by bubbling argon through the mixture and the resulting mixture was stirred at 100° C. overnight, cooled to RT and partitioned between EtOAc and sat'd. aq. NH$_4$Cl. The aqueous layer was back extracted twice with EtOAc. The combined organic extracts were dried (Na$_2$SO$_4$), filtered, and evaporated. The residue was purified by SiO$_2$ chromatography (40 g SiO$_2$) eluting with an EtOAc/hexane gradient (10 to 30% EtOAc), to afford 0.28 g (45%) of 90a.

step 2—To a solution of 90a (0.32 g, 0.65 mmol) in DCM (2 mL) at RT was added HCl (2 mL, 4M solution in dioxane). The resulting orange mixture was stirred at RT overnight then evaporated. The bright orange solid was partitioned between EtOAc and sat'd. aq. NaHCO₃. The aqueous layer was back extracted twice with EtOAc. The combined organic extracts were dried (Na₂SO₄), filtered, and evaporated to afford 0.25 g of crude 90b which was used in the next reaction with further purification.

step 3—To a mixture of crude 90b (0.25 g, 0.637 mmol) and pyridine (0.062 g, 0.765 mmol) in 3 mL of DCM cooled to 0° C. was added methanesulfonyl chloride (0.055 mL, 0.716 mmol). The resulting mixture was stirred at RT for 2 h then partitioned between EtOAc and 1M aq. NaOH. The aqueous layer was back extracted twice with EtOAc. The combined organic extracts were dried (Na₂SO₄), filtered, and evaporated. The residue was purified by SiO₂ chromatography (22 g SiO₂) eluting with EtOAc/hexane (4/1) to afford 0.12 g (40%) of 90c.

Introduction of the dioxo-tetrahydro-pyrimidin-1-yl was carried out in accord with the procedures described in steps 1 to 3 of example 18 to afford I-31.

N—{(S)-1-[6-tert-Butyl-8-(2,4-dioxo-3,4-dihydro-2H-pyrimidin-1-yl)-5-methoxy-quinolin-3-yl]-pyrrolidin-3-yl-methyl}-methanesulfonamide (I-52) is prepared from 90c utilizing the procedures for introduction of 2,4-dioxo-3,4-dihydro-2H-pyrimidin-1-yl moiety described in steps 1-3 of example 23.

N—{(S)-1-[6-tert-Butyl-5-methoxy-8-(6-methyl-2-oxo-1,2-dihydro-pyridin-3-yl)-quinolin-3-yl]-pyrrolidin-3-ylmethyl}-methanesulfonamide, HBr salt was prepared analogously except the 6-methyl-2-oxo-1,2-dihydro-pyridin-3-yl moiety was introduced into the 8-position of 90c as described in step 7 of example 1.

Example 20

N-{4-[8-(Dioxo-tetrahydro-pyrimidin-1-yl)-5-methoxy-6-(2,2,2-trifluoro-ethyl)-quinolin-3-yl]-phenyl}-methanesulfonamide (I-30)

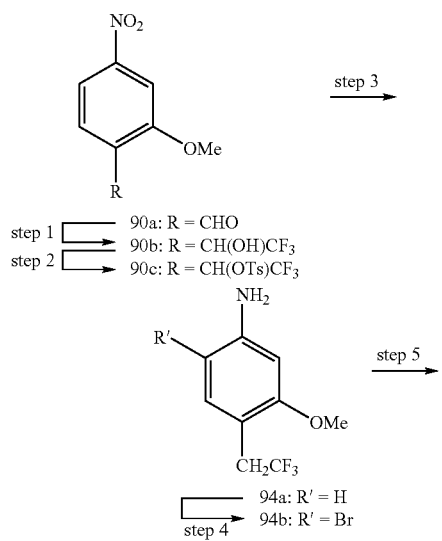

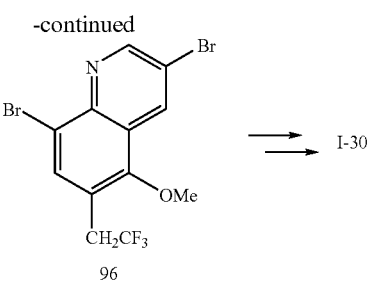

step 1—A 250 mL round bottom flask fitted with a stir bar and cap was charged with 92a (9.93 g) and anhydrous DME (100 mL) and stirred to obtain a clear yellow solution. To this solution was added sequentially CF₃SiMe₃ (9.0 mL) and CsF (792 mg). The reaction mixture was sonicated for 20 min, and then stirred at RT for an additional 40 min. A 2.0 M HCl solution (100 mL) was added and the resulting mixture stirred at RT for 1 h. EtOAc (200 mL) was added and the phases were separated. The organic phase was washed with sat'd. aq. NaHCO₃ (150 mL) and brine (150 mL), dried (MgSO₄), filtered and concentrated in vacuo. The crude product was purified by flash chromatography (385 g Supelco VersaPak™ SiO₂ column) eluting with a DCM/hexane gradient (0 to 100% DCM) over 5 column volumes. The recovered product was dissolved in DCM (100 mL) and hexane (200 mL) was added. Approximately ⅔ of the solvent was slowly removed in a rotary evaporator. The resulting precipitate was filtered, washed with hexane, and dried under high vacuum to afford 13.10 g of 92b as a white solid.

step 2—A 1 L round bottom flask fitted with a stir bar, reflux condenser, and nitrogen inlet and charged with 92b (13.01 g) and maintained under a nitrogen atmosphere. Anhydrous THF (300 mL) was added and the mixture stirred to obtain a clear yellow solution. To the solution was added NaH (2.25 g, 60 wt % dispersion in mineral oil) at RT. The mixture was sonicated for 20 min, stirred at RT for an additional 10 min. A solution of p-toluenesulfonyl chloride (11.86 g) and dry THF (100 mL) was added at RT and stirred at 50° C. for 90 min. The solution was cooled and poured into 0.5 M aq. NaHCO₃ (1 L). The reaction mixture was diluted with EtOAc (500 mL) and the organic phase separated, washed with brine (500 mL), dried (MgSO₄), filtered and concentrated in vacuo. The crude product was dissolved in DCM and chromatographed (385 g Supelco VersaPak™ SiO₂ column) eluting with a DCM/hexane gradient (0 to 100% DCM) over 10 column volumes. The light yellow resin slowly crystallized to afford 20.36 g of 92c as a white solid.

step 3—A Parr hydrogenation flask was charged with 92c (20.35 g) and dissolved in hot EtOH (200 mL) and the solid washed into the flask with 50 mL of EtOH. The solution was purged with nitrogen for 5 min while keeping the solution warm. To the solution was added 10% Pd/C (4.02 g) and the flask was flushed with nitrogen. The solution was hydrogenated on a Parr shaker under 55 psi of hydrogen at 50° C. for 1.5 h. The catalyst was removed by filteration through a glass-fiber filter and washed with hot EtOH (100 mL). The filtrate was concentrated in a rotary evaporator. The tosylate salt precipitated as a white solid. The residue was partitioned between 1.0 M aq. NaOH (500 mL) and Et₂O (300 mL). The phases were separated and the aqueous phase was extracted with Et$_2$O (3×300 mL). The combined organic extracts were washed with brine (450 mL), dried (MgSO$_4$), filtered and concentrated in vacuo. The residue was purified by flash chromatography (385 g Supelco VersaPak™ SiO$_2$ column) eluting with DCM to obtain 9.04 g of 94a as an off-white solid.

step 4—A 250 mL round bottom flask fitted with a stir bar and septum was charged with 94a (8.16 g) and maintained nitrogen atmosphere. To the flask was added dry dioxane (100 mL) and HOAc (23 mL) and the solution cooled to between 5-10° C. with an ice bath. A solution of Br$_2$ (7.03 g) in dioxane (45 mL) was added dropwise over 30 min using a syringe pump. A beige precipitate formed. The solution was warmed to RT and stirred 1 h the poured into 1.0 M NaOH (500 mL) and extracted with DCM (3×300 mL). The combined extracts were washed with brine (450 mL), dried (MgSO$_4$), filtered and concentrated in vacuo to afford 11.42 g of 94b as a pale olive solid.

step 5—A 40 ml, vial was charged with 2-bromoacrolein (2.71 g), fitted with a stir bar and septum and HOAc (25 mL) was added. The solution was cooled in an ice/water bath and Br$_2$ was added dropwise until the red color persisted (ca. 1.0 mL). Several drops of 2-bromoacrolein were until the solution was again colorless. This solution was poured into a stirred solution of 94b (5.67 g) and HOAc (25 mL) and the resulting mixture stirred at 100° C. for 2 h. The solution was cooled, diluted with H$_2$O (250 mL) and extracted with EtOAc (3×100 mL). The combined extracts were washed sequentially with 2.0 M aq. NaOH (200 mL) and brine (150 mL), dried (MgSO$_4$), filtered and concentrated in vacuo. The crude product was purified by chromatography (385 g Supelco VersaPak™ SiO$_2$ column) eluting with DCM to obtain 2.69 g of 96 as a light orange solid.

Introduction of the 4-methanesulfonylaminophenyl substituent at the 3 position was carried out in accord with the procedure described in step 5 of example 19 to afford N-{4-[8-Bromo-5-methoxy-6-(2,2,2-trifluoro-ethyl)-quinolin-3-yl]-phenyl}-methanesulfonamide (97). Introduction of the dioxo-tetrahydro-pyrimidin-1-yl at the 8 position of 97 was carried out in accord with the procedures described in steps 1 to 3 of example 18 to afford I-30.

N-{4-[5-Methoxy-8-(6-methyl-2-oxo-1,2-dihydro-pyridin-3-yl)-6-(2,2,2-trifluoro-ethyl)-quinolin-3-yl]-phenyl}-methanesulfonamide hydrobomide salt (I-53) is prepared from 96 utilizing the procedure described in step 5 of example 19 to introduce the methanesulfonylamino-phenyl moiety and subsequently using the Suzuki coupling/demethylation sequence described in steps 3 and 4 of example 9 except in step 3,2-methoxy-pyridin-3-yl boronic acid was replaced by 2-methoxy-6-methyl-pyridin-3-yl boronic acid.

N-{4-[5-Methoxy-8-(6-methoxy-2-oxo-1,2-dihydro-pyridin-3-yl)-6-(2,2,2-trifluoro-ethyl)-quinolin-3-yl]-phenyl}-methanesulfonamide (I-54) is prepared analogously except in step 3,2-methoxy-pyridin-3-ylboronic acid was replaced by with 115. Demethylation afforded the HBr salts in both cases.

N-{4-[8-(2,4-Dioxo-3,4-dihydro-2H-pyrimidin-1-yl)-5-methoxy-6-(2,2,2-trifluoro-ethyl)-quinolin-3-yl]-phenyl}-methanesulfonamide (I-56) was prepared analogously except the 2,4-dioxo-3,4-dihydro-2H-pyrimidin-1-yl at the 8 position of 97 was carried out in accord with the procedures described in steps 1 to 3 of example 23.

Example 21

N-{4-[6-[1,1-di(methyl-d$_3$)ethyl-2,2,2-d$_3$]-5-methoxy-8-(6-methoxy-2-oxo-1,2-dihydro-pyridin-3-yl)-quinolin-3-yl]-phenyl}-methanesulfonamide (I-32)

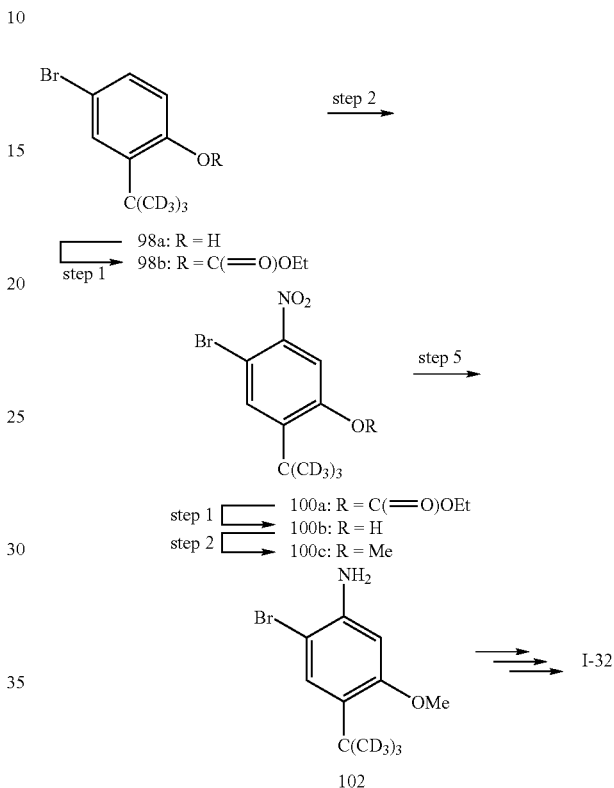

step 1—A solution of CD$_3$OD (25 mL) and 4-bromophenol (8.5 g, 49.2 mmol) was stirred at RT for 30 min to exchange the phenolic proton and then the CD$_3$OD was removed in vacuo. The resulting solid was dissolved in CDCl$_3$ (10 mL) and (CD$_3$)$_3$COD (4 mL) and warmed to 60° C. Concentrated D$_2$SO$_4$ (10 mL) was added in five 2 mL portions over 50 min. The reaction mixture was maintained at 60° C. overnight and then poured over ice (50 mL) and extracted with EtOAc (2×75 mL). The combined organics were extracted with 2N aqueous KOH (3×300 mL), washed with 1N aqueous HCl (75 mL) and brine (25 mL), dried (MgSO$_4$), filtered and concentrated in vacuo. The residue was purified by SiO$_2$ chromatography eluting with an EtOAc/hexane gradient (0 to 10% EtOAc over 40 min) to afford 5.83 g of 98a as a brown oil: ES MS (M−H) 236.1.

step 2—To a solution of 2-(D$_9$-tert-butyl)-4-bromophenol (98a, 35.1 g, 147 mmol) and TEA (17.9 g, 177 mmol) in Et$_2$O (285 mL) maintained at 0° C. in an ice bath was added dropwise over 10 min ethyl chloroformate (18.4 g, 16.3 ml, 169 mmol). A white precipitate was observed after about 5 min. The reaction was maintained at 0° C. with vigorous stirring for 3 h. The mixture was diluted with sat'd. aq. NH$_4$Cl (100 mL), and the layers were separated. The aqueous layer is washed with Et$_2$O (100 mL), dried (MgSO$_4$), filtered and concentrated in vacuo. The residue is purified by SiO$_2$ chromatography eluting with an EtOAc/hexane gradient (0 to 10% EtOAc over 45 min) to 36.5 g of 98b as a brown oil: ES MS (M+H) 310.1.

step 3—To a solution of 98b (36 g, 116 mmol) in concentrated sulfuric acid (147 g, 80 mL, 1.5 mol) cooled to 0° C. was added dropwise over 10 min 70% HNO$_3$ (8.77 g, 6.22 mL, 139 mmol). The reaction was maintained at 0° C. for 2 h and then poured over ice (ca. 500 g). The aqueous solution was extracted with 1:1 EtOAc/hexanes (3×200 mL), and the combined organic extracts were washed with brine, dried (MgSO$_4$), filtered and concentrated onto SiO$_2$ (100 g). The product was purified by SiO$_2$ chromatography eluting with an EtOAc/hexane gradient (0 to 10% EtOAc over 45 min) to afford 35.8 g of 100a as a yellow solid: ES MS (M+H) 355.1.

step 4—Solid pellets of KOH (8.29 g, 148 mmol) were added over the course of 1 min to a solution of 100a (35.0 g, 98.5 mmol) in MeOH (800 mL) the resulting solution placed in a RT water bath overnight. The MeOH was removed in vacuo and the residue dissolved in DCM (150 mL). The organic solution was washed with 2 N HCl (200 mL) and the aqueous layer was back-extracted with DCM (50 mL). The combined extracts were washed with brine, dried (MgSO$_4$), filtered and concentrated in vacuo to afford 27.8 g of 100b as a viscous orange liquid that was used in the next step without any further purification: ES MS (M−H) 281.1.

step 5—Iodomethane (17.4 g, 7.67 mL, 123 mmol) was added dropwise to a suspension of 100b (27.8 g, 98.2 mmol) and K$_2$CO$_3$ (20.4 g, 147 mmol) in acetone (110 mL) at RT. The red suspension was stirred vigorously at RT for 16 h. Ice water (500 mL) was added which produced a fine yellow precipitates. The mixture is stirred for 30 min, filtered and the solid washed with H$_2$O (150 mL). The solid was dried under vacuum at 40° C. overnight to afford 24.8 g of 100c which was used without further purification: ES MS (M+H) 297.1.

step 6—A 1 L three-necked flask was charged with 100c (24 g, 80.8 mmol), iron powder (22.5 g, 404 mmol) and NH$_4$Cl (21.6 g, 404 mmol), EtOH (200 mL) and H$_2$O (200 mL). The flask is fitted with a condenser, and the yellow suspension was heated to 70° C. and stirred vigorously for 15 h with a mechanical stirrer. The reaction was cooled to RT and filtered through CELITE. The CELITE pad was washed with MeOH (ca. 100 mL). Most of the MeOH and EtOH were removed in vacuo. The aqueous mixture was extracted with EtOAc (3×100 mL). The combined extracts were dried (MgSO$_4$), filtered and concentrated in vacuo which afforded 21.1 g of 102 as a light brown oil that solidified upon standing and which was used without any further purification: ES MS (M+H) 267.1.

The conversion of 102 to I-32 was carried out in accord with procedures described in steps 2 though 5 in Example 9 except in step 3, 2,6-methoxy-pyridin-3-yl boronic acid was used in place of 59: $^1$H NMR (300 MHz, DMSO-d$_6$) δ d 10.0 (br s, 1H), 9.12 (d, J=2.3 Hz, 1H), 8.54 (d, J=2.3 Hz, 1H), 7.88 (d, J=8.6 Hz, 2H), 7.60 (s, 1H), 7.36 (d, J=8.6 Hz, 1H), 6.31 (br s, 1H), 4.00 (s, 3H), 3.87 (s, 3H), 3.04 (s, 3H).

Example 22

N-{4-[6-tert-Butyl-5-methoxy-8-(6-methoxy-2-oxo-1,2-dihydro-pyridin-3-yl)-quinolin-3-yl]-phenyl}-methanesulfonamide (I-34)

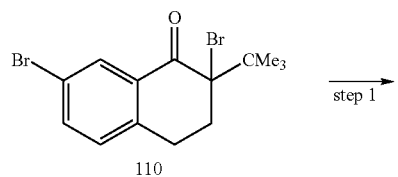

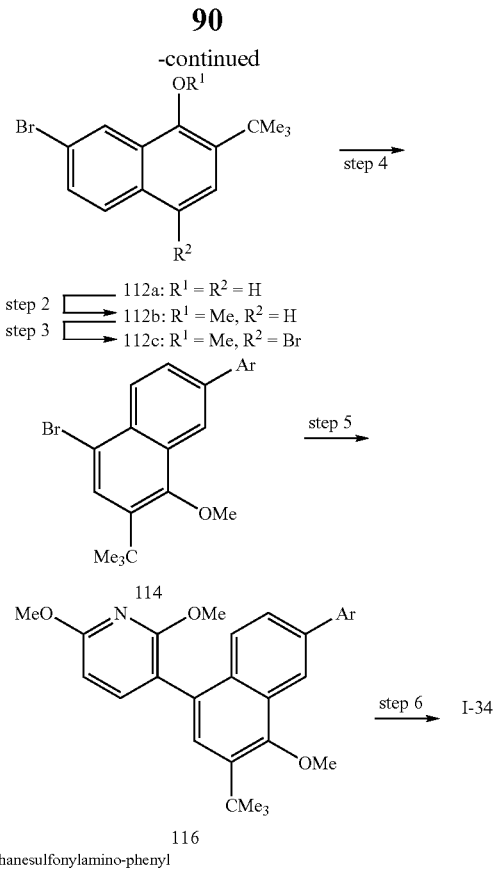

Ar = 4-methanesulfonylamino-phenyl 2,7-Dibromo-2-tert-butyl-3,4-dihydro-2H-naphthalen-1-one (110): step a—A solution of (7-bromo-3,4-dihydronaphthalen-1-yloxy)trimethylsilane (6.85 g, 11.5 mmol, CASRN 309929-09-7) and DCM (23.0 mL) was cooled to −40° C. 2-Chloro-2-methylpropane (1.12 g, 1.32 mL, 12.1 mmol) was added and the solution stirred under nitrogen. A solution of TiCl$_4$ (2.19 g, 1.27 mL, 11.5 mmol) in DCM (6 mL) was added dropwise while maintaining the solution at −40° C. Soon after addition was complete TLC indicated ca. 50% conversion. The reaction was stirred at RT over the weekend then poured onto ice. The mixture was partitioned between EtOAc and H$_2$O and aqueous layer was neutralized with satd. aq. NaHCO$_3$. The mixture was filtered through a plug of celite to a remove chunky white precipitate. The organic layer was separated, washed with brine, dried (MgSO$_4$), filtered and concentrated. The crude product was applied to a hexane equilibrated SiO$_2$ column and eluted with an EtOAc/hexane gradient (0 to 5% EtOAc) to afford 3.26 g (quantitative) of 7-bromo-2-tert-butyl-3,4-dihydro-2H-naphthalen-1-one (109) a yellow solid.

step b—To a solution of 109 (3 g, 10.7 mmol) and HOAc (40 mL) stirred at RT under N$_2$ was added dropwise via cannula a solution of bromine (1.88 g, 605 μL, 11.7 mmol) in HOAc (20.0 mL) over 20 min. The solution was stirred for 1 h at RT then warmed reaction to 50° C. and stirred 1 h. An aliquot of neat bromine (100 μL) was added and heating continued. The total heating time was 2.5 h. The reaction mixture was poured over ice, partitioned between EtOAc and H$_2$O and aqueous phase was neutralized with satd. aq. NaHCO$_3$. The organic layer was separated, washed with brine, dried (MgSO$_4$), filtered and concentrated. The product was purified by SiO$_2$ chromatography eluting with hexanes to afford 3.8 g (quantitative) of 110.

step 1—A round-bottom flask was charged with 110 (3.8 g, 10.6 mmol), LiBr (275 mg, 3.17 mmol), Li$_2$CO$_3$ (780 mg, 10.6 mmol) and DMF (44.0 mL) and Ar was bubbled through the white suspension for 10 min. The suspension was heated at 100° C. for 1 h under N$_2$. The reaction was cooled to RT, diluted with EtOAc, thrice washed with water then with brine, dried (MgSO$_4$), filtered and concentrated to afford 112a as light brown viscous oil which was used without additional purification.

step 2—To a solution of 112a (2.9 g, 10.4 mmol) and K$_2$CO$_3$ (3.59 g, 26.0 mmol) in DMF (29.7 mL) was added MeI (1.77 g, 779 µL, 12.5 mmol) and the mixture was capped and stirred at 25° C. overnight. The mixture was diluted with EtOAc and water and the aqueous phase was neutralized with 1N HCl. The organic layer was separated, washed with brine, dried (MgSO$_4$), filtered and concentrated to afford 112b which was used without additional purification.

step 3—To a solution of 112b (1.6 g, 5.46 mmol) and HOAc (30 mL) maintained under nitrogen was added dropwise via addition funnel a solution of bromine (872 mg, 281 µL, 5.46 mmol) in HOAc (20 mL). The mixture stirred at RT overnight. The mixture was diluted with EtOAc and water and aqueous phase was neutralized with sat'd. aq. NaHCO$_3$. The organic layer was separated, washed with brine, dried (MgSO$_4$), filtered and concentrated to afford 112c which was used without additional purification step 4—A 2-5 mL microwave tube was charged with 112c (1 g, 2.69 mmol), 25 (578 mg, 2.69 mmol), Na$_2$CO$_3$ (855 mg, 8.06 mmol) MeOH (7.14 mL), toluene (3.57 mL) and H$_2$O (1.79 mL). The mixture was degassed with argon for 10 min then Pd(PPh$_3$)$_4$ (155 mg, 134 µmol) was added. Degassing was continued for another 5 min then the vial was sealed and heated thermally for 1.5 h at 115° C. The mixture was cooled, partitioned between EtOAc and water and the aqueous phase was neutralized with 1N HCl. The organic layer was separated, washed with brine, dried (MgSO$_4$), filtered and concentrated in vacuo. The crude product was purified by SiO$_2$ chromatography and eluted with an EtOAc/hexane gradient (20 to 50% EtOAc) to afford 0.67 g (54%) of 114 as a white solid.

step 5—A 2-5 mL microwave tube was charged with 114 (0.08 g, 173 µmol), 2,6-dimethoxypyridin-3-ylboronic acid (115, 34.8 mg, 190 µmol), and Na$_2$CO$_3$ (55.0 mg, 519 µmol), MeOH (1.5 mL), toluene (750 µL) and H$_2$O (165 µL). The mixture was degassed with argon for 10 min then Pd(PPh$_3$)$_4$ (10.0 mg, 8.65 µmol) was added and degassing continued for another 5 min. The vial was sealed and irradiated in a microwave reactor for 20 min at 115° C. The mixture was cooled, diluted with EtOAc and H$_2$O and the aqueous phase was neutralized with 1N HCl. The organic layer was separated, washed with brine, dried (MgSO$_4$), filtered and concentrated in vacuo. The crude product was purified on a preparative SiO$_2$ TLC plate developed with 40% EtOAc/hexane to afford 82 mg (92%) of 116 as a light brown foam.

step 6—A vial was charged with 116 (0.082 g), HBr (53.1 mg, 35.6 µL, 315 mmol) and HOAc (0.75 mL), flushed with argon and sealed. The sealed mixture was heated at 55° C. for 6 h. The reaction was cooled, diluted with EtOAc and poured onto ice. The resulting solution was neutralized with satd. aq. NaHCO$_3$. The organic phase was washed with brine, dried (MgSO4), filtered and concentrated in vacuo. The crude product was purified on a SiO$_2$ plate developed with 50% EtOAc/hexane to afford 44 mg of I-34

Example 23

N-{4-[6-tert-Butyl-8-(2,4-dioxo-3,4-dihydro-2H-pyrimidin-1-yl)-5-methoxy-quinolin-3-yl]-phenyl}-methanesulfonamide (I-35)

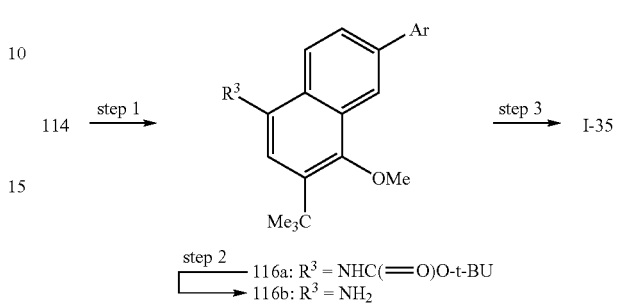

step 1—A 10-20 mL microwave tube was charged with 114 (0.35 g, 0.757 mmol), tent-butyl carbamate (124 mg, 1.06 mmol) and sodium tert-butoxide (107 mg, 1.11 mmol) and toluene (6.00 mL) which produced a white suspension. The mixture was flushed with argon for 10 min. The extremely viscous mixture was diluted with toluene (4 mL), then Pd$_2$(dba)$_3$ (104 mg, 114 µmol) and 2-di-tert-butylphosphino-2',4',6'-triisopropylbiphenyl (145 mg, 341 µmol) were added and argon was bubbled through the mixture for 5 min. The reaction was stirred over the weekend at RT in a sealed vial. The mixture was partitioned between EtOAc and H$_2$O and the aqueous solution was neutralized with 1N HCl. The organic layer was separated, washed with brine, dried (MgSO$_4$), filtered and concentrated in vacuo. The crude product was purified by SiO$_2$ chromatography eluting with an EtOAc/hexane gradient (20-60% EtOAc) to afford 196 mg (52%) of 116a.

step 2—A 25 mL pear-shaped flask was charged with 116a (0.196 g, 197 µmol), DCM (1.5 mL) and 4 M HCl in dioxane (491 µL, 1.97 mmol) then stirred at RT for 3 h. Once all starting material disappeared, the solution was diluted, poured over ice and neutralized with satd. aq. NaHCO$_3$. The mixture was concentrated and purified by SiO$_2$ chromatography eluting with an EtOAc/hexane gradient (20-50% EtOAc) to afford 116b which used without further purification.

step 3—A small flask was covered with foil charged with cyanatosilver (135 mg, 903 µmol) and heated overnight at 50° C. under high vacuum. To the resulting solid was added sequentially dry toluene (1.29 mL), (E)-3-methoxyacryloyl chloride (65.3 mg, 542 µmol). The resulting slurry was heated under nitrogen to 120° C. for 30 min. The mixture was cooled to RT then immersed in an ice-bath and the solid was allowed to settle. In a separate dry flask, 116b (0.072 g, 181 µmol) was dissolved in DMF (1.03 mL) and cooled to 0° C. To the DMF solution was added dropwise over 10 min the supernatant from the cyanatosilver flask. A light brown heterogeneous mixture formed after addition which was stirred 30 min in ice bath. The mixture was diluted with EtOAc, washed sequentially with H$_2$O and brine. The presence of the intermediate urea was confirmed by NMR as a mixture of cis and trans isomers. The urea was taken up in EtOH (1.03 mL) and an 11% H$_2$SO$_4$ solution in H$_2$O (1.03 mL) was added. The resulting mixture was sealed in a vial and heated to 120° C. for 1.5 hr until the solution was homogenous. The mixture was cooled, poured over ice and diluted with EtOAc. The organic phase was diluted with EtOAc, washed sequentially with H$_2$O and brine, dried (MgSO$_4$), filtered and concentrated. The

Example 24

N—{(S)-1-[7-tert-Butyl-8-methoxy-5-(6-methoxy-2-oxo-1,2-dihydro-pyridin-3-yl)-naphthalen-2-yl]-pyrrolidin-3-ylmethyl}-methanesulfonamide (I-36)

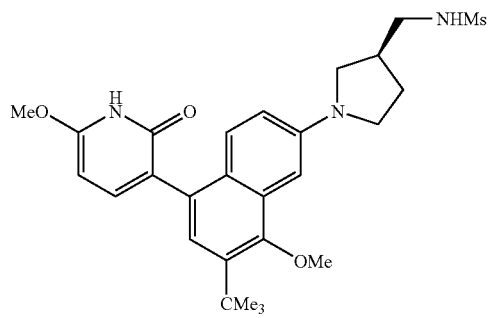

step 1—A 10-20 mL microwave tube was charged with (S)-72 (184 mg, 1.03 mmol) and toluene (4.69 mL) to afford a brown solution. To this was added 112c (349 mg, 938 µmol) and toluene (4.69 mL). Argon was bubbled through the solution for 10 min then Pd$_2$(dba)$_3$ (85.9 mg, 93.8 µmol) and XANTPHOS (109 mg, 188 µmol) was added. Degassing was continued for 5 min then sodium tert-butoxide (135 mg, 1.41 mmol) was added quickly, the solution flushed with argon and sealed. The solution was irradiated in a microwave synthesizer at 100° C. for 10 min then stirred overnight at RT. Some DMSO was added to dissolve the solids and the vial heated thermally for 3 h. The mixture was cooled, diluted with EtOAc and water and aqueous layer was neutralized with 1N HCl. The organic layer was separated, washed with brine, dried (MgSO$_4$), filtered and concentrated in vacuo. The crude product was purified on a preparative SiO$_2$ TLC plate developed twice with 50% EtOAc/hexane to afford 92 mg of 118. The product was used without additional purification.

step 2—A 2-5 mL microwave tube was charged with 118 (85 mg, 181 µmol), 115 (39.8 mg, 217 µmol), Na$_2$CO$_3$ (57.6 mg, 543 µmol), MeOH (0.4 µl), toluene (0.2 µL) and H$_2$O (0.2 µL). The mixture was bubbled with argon for 10 min then Pd(PPh$_3$)$_4$ (10.5 mg, 9.05 µmol) was added. Argon was bubbled through the solution another 5 min. The vial was sealed and irradiated in a microwave reactor at 115° C. for 20 min. The mixture was cooled, diluted with EtOAc and water and aqueous layer was neutralized with 1N HCl. The organic layer was separated, washed with brine, dried (MgSO$_4$), filtered and concentrated in vacuo. The crude product was purified by SiO$_2$ chromatography eluting with an EtOAc/hexane gradient (25-50% EtOAc) to afford 56.6 mg of 120.

step 3—Demethylation of the ether to afford the pyridone was carried out as described in step 6 of example 22. The crude product was purified by SiO$_2$ chromatography eluting with an EtOAc/hexane gradient (50 to 75% EtOAc) to afford I-36 as an off white solid.

Example 25

N-{4-[6-(1-Difluoromethyl-cyclopropyl)-5-methoxy-8-(6-methyl-2-oxo-1,2-dihydro-pyridin-3-yl)-quinolin-3-yl]-phenyl}-methanesulfonamide (I-37)

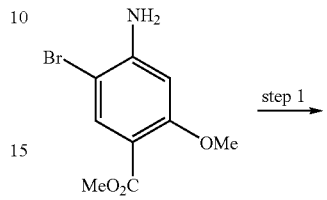

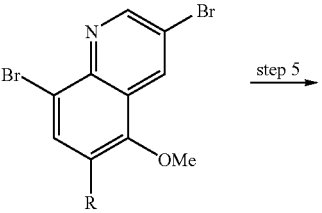

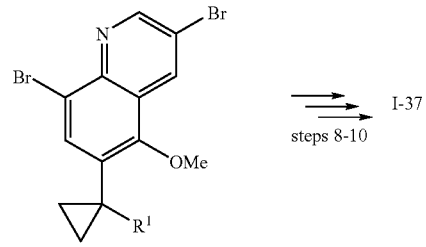

step 1—Bromine (4.48 mL, 86.9 mmol) in HOAc (50 mL) was added to a solution of 2-bromoacrylaldehyde (11.7 g, 86.9 mmol, CASRN 111049-68-4) in HOAc (100 mL) at RT until the solution showed faint Br$_2$ color. To this solution was added methyl 4-amino-5-bromo-2-methoxybenzoate (22.6 g, 86.9 mmol) and the resulting solution was gradually heated to 100° C. After the temperature reached 100° C., stirring was continued for 15 min then the solution was cooled and concentrated in vacuo. The reaction mixture was neutralized with satd. aq. NaHCO$_3$ and the resulting solid was filtered and washed with water. The solid was washed with ether followed by 10% MeOH/DCM to afford 11.04 g of 122a. The filtrate was absorbed onto SiO$_2$ and purified on a flash column eluting with a DCM/hexane gradient (50 to 100% DCM to afford an additional 3.46 g of 122a.

step 2—To a heterogeneous solution 122a (11.05 g, 29.5 mmol) in DCM (550 mL) at 0° C. was added dropwise DIBAL (9.22 g, 64.38 mmol). When the addition was finished the reaction was complete. The reaction was quenched with aq. Rochelle salt and partitioned between H₂O and DCM. The organic layer was washed with H₂O and dried (Na₂SO₄), filtered and concentrated in vacuo. The crude product was adsorbed onto SiO₂ and purified by flash chromatography eluting with a DCM/MeOH gradient (0 to 10% MeOH) to afford 9.5 g of 122b.

step 3—A solution of 122b (7.82 g, 22.5 mmol), CBr₄ (8.97 g, 1.2 eq) and Ph₃P (7.09 g, 1.2 eq) and DCM (250 mL) was stirred at RT overnight. The following morning 0.5 eq each of CBr₄ and PPh₃ were added. After 1 h, the reaction was complete. The crude reaction mixture was concentrated in vacuo. The crude product was adsorbed onto SiO₂ and purified by flash chromatography eluting with DCM/hexane gradient (0 to 100% DCM) to afford 7.62 g of 122c as a white solid.

step 4—A solution of 122c (8.00 g, 19.1 mmol), KCN (12.4 g, 191 mmol), DCM (156 mL) and H₂O (140 mL) was heated at reflux for 15 min. The reaction mixture was diluted with H₂O and extracted with DCM. The organic layers were dried (Na₂SO₄), and concentrated in vacuo. The residue was dry loaded onto a SiO₂ flash chromatography column and purified by flash chromatography eluting with a MeOH/DCM gradient (0 to 5% MeOH) to afford 122d as a white solid.

step 5—A mixture of 122d (5.02 g, 14.1 mmol), 1,2-dibromoethane (3.18 g, 1.46 mL, 16.9 mmol) and DMF (60 mL) was cooled to 0° C. and NaH (1.69 g, 42.3 mmol, 60% mineral oil dispersion) was added. The mixture was warmed to RT and stirred for 1 h. The reaction mixture was diluted with H₂O and extracted with DCM. The organic layer was washed twice with H₂O, dried (Na₂SO₄), filtered and concentrated in vacuo. The crude product was dried loaded onto a SiO₂ and purified by flash chromatography eluting with a DCM/hexane gradient (0 to 100% DCM) to afford 1.91 g of 124a.

step 6—To a solution of 124a (0.28 g, 0.733 mmol) in DCM (14 mL) was added DIBAL (870 µL, 0.879 mmol, 1M in DCM) dropwise at −78° C. The reaction mixture was stirred at −78° C. for 1 h. The reaction was quenched with aq. Rochelle salt and extracted with DCM. The organic layer was washed with H₂O, dried (Na₂SO₄), filtered and concentrated in vacuo. The crude material was purified by flash chromatography to afford 0.22 g of 124b as white solid was obtained.

step 7—To a solution of 124b (0.63 g, 1.64 mmol) in DCM (14.3 mL) was added DAST 1.05 g, 6.54 mmol) and the resulting solution was stirred at for 72 h. The reaction mixture was diluted with H₂O and extracted with DCM. The organic layer was washed with H₂O and dried (Na₂SO₄), filtered and concentrated in vacuo. The crude product was purified by SiO₂ chromatography eluting with a DCM/hexane gradient (50 to 100% DCM) to afford 0.60 g of 124c as a white solid.

Step 8 to 10 were carried out in accord with procedures in steps 4-6 of example 22, except in step 5, 115 was replaced with 75.

N-{4-[6-(1-Difluoromethyl-cyclopropyl)-5-methoxy-8-(6-methyl-2-oxo-1,2-dihydro-pyridin-3-yl)-quinolin-3-yl]-phenyl}-methanesulfonamide (I-38) was prepared analogously except in step 5, 115 was replaced 75.

N-{4-[6-(1-Difluoromethyl-cyclopropyl)-8-(2,4-dioxo-3,4-dihydro-2H-pyrimidin-1-yl)-5-methoxy-quinolin-3-yl]-phenyl}-methane sulfonamide (I-39) was prepared from 124c in accord with steps 1 to 3 of example 23 to introduce the uracil.

Example 26

N—{(S)-1-[6-tert-Butyl-5-methoxy-8-(1-methyl-2,4-dioxo-1,2,3,4-tetrahydro-pyrimidin-5-yl)-quinolin-3-yl]-pyrrolidin-3-ylmethyl}-methanesulfonamide
(I-40)

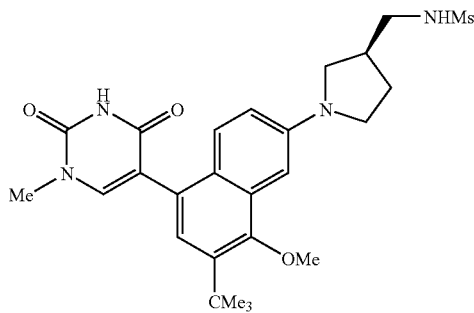

2,4-Dimethoxy-5-(4,4,5,5-tetramethyl-1,3,2-dioxaborolan-2-yl)pyrimidine (117)—A 250 mL round-bottomed flask was charged with 5-bromo-2,4-dimethoxypyrimidine (1.23 g, 5.62 mmol), PdCl₂(dppf).CH₂Cl₂ (229 mg, 281 µmol), bis-(pinacolato)diboron (1.71 g, 6.74 mmol), KOAc (1.65 g, 16.8 mmol) and DMF. The light yellow solution was heated to 100° C. and stirred for 1 h. The reaction mixture was poured into 50 mL of H₂O and extracted with EtOAc/toluene (1:1, 3×50 mL). The organic layers were combined, washed with H₂O (1×50 mL), satd. aq. NaCl (50 mL). The organic layer was dried (Na₂SO₄), dried, filtered and concentrated in vacuo to afford a 7:3 mixture of 117 (1.67 g, 78%) and recovered bromide. The dark solid was used in the next step without further purification.

step 1—A 10 mL screw-capped tube was charged with N—[(S)-1-(5-bromo-7-tert-butyl-8-methoxy-naphthalen-2-yl)-pyrrolidin-3-ylmethyl]-methanesulfonamide (118, 0.188 g, 400 µmol), PdCl₂(dppf).CH₂Cl₂ (16.3 mg, 20.0 µmol), Cs₂CO₃ (391 mg, 1.2 mmol) and 117 (182 mg, 480 µmol), dioxane (3.2 mL) and H₂O (799 µL) to afford a dark brown solution. The reaction mixture was heated to 100° C. and stirred for 30 min. The reaction mixture was poured into 50 mL of H₂O and extracted with EtOAc (3×50 mL). The organic layers were combined, washed with H₂O (50 mL) and brine (50 mL). The organic layers were dried (Na₂SO₄), filtered and concentrated in vacuo. The crude material was purified by SiO₂ chromatography eluting with a MeOH/DCM gradient (0% to 5% MeOH) to afford 0.077 g (36%) of 120 as a solid.

step 2—A 10 mL screw-capped tube was charged with 120 (0.055 g, 104 µmol), MeI (250 mg, 0.11 mL, 1.76 mmol) and DCM (0.11 mL). The light yellow solution was stirred for 5 h and then evaporated. The crude material was purified by SiO₂ chromatography eluting with a DCM/hexane gradient (0 to 6% MeOH) to afford 0.022 g (40%) of (S)-N-((1-(6-tert-butyl-5-methoxy-8-(4-methoxy-1-methyl-2-oxo-1,2-dihydropyrimidin-5-yl)quinolin-3-yl)pyrrolidin-3-yl)methyl) methanesulfonamide (122) as a solid.

step 3—A 10 mL screw-capped tube was charged with 122 (0.021 g, 39.6 µmol), HBr (16.0 mg, 10.8 µL, 198 µmol) and HOAc. After 4 h the reaction mixture was poured into satd.

aq. NaHCO₃ (50 mL) and extracted with EtOAc (3×20 mL). The organic extract was dried (Na₂SO₄), filtered and evaporated to 0.020 g (98%) of I-40 as a yellow solid.

N-{4-[6-tert-Butyl-5-methoxy-8-(1-methyl-2,4-dioxo-1,2,3,4-tetrahydro-pyrimidin-5-yl)-quinolin-3-yl]-phenyl}-methanesulfonamide was prepared from 114 using the procedures in step 1 to 3 of this example.

Example 27

N-{4-[6-tert-Butyl-8-(5-chloro-6-methyl-2-oxo-1,2-dihydro-pyridin-3-yl)-5-methoxy-quinolin-3-yl]-phenyl}-methanesulfonamide (I-42)

Neutralization of I-24 hydro bromide (34 mg, 0.059 mmol) with satd. aq. NaHCO₃ afforded the free base which was extracted with EtOAc. The EtOAc extract was dried (MgSO₄), filtered and concentrated. The residue was dissolved in MeCN (1 mL) and DMF (1 mL) and warmed to 60° C. NCS (8 mg, 0.06 mmol) was then added to the reaction mixture. After stirring at 60° C. for 1.5 h, the reaction mixture was cooled to RT and diluted with EtOAc. The organic layer was washed with water, dried (MgSO₄), filtered and concentrated. The crude residue was purified by SiO₂ chromatography eluting with 9:1 DCM/MeOH to afford 8 mg (49%) of I-42 as a white solid. MS m/z (ES): 527 (M+H)⁺.

Example 28

3-[3-(6-Amino-pyridin-3-yl)-6-tert-butyl-5-methoxy-quinolin-8-yl]-1H-pyridin-2-one (I-43)

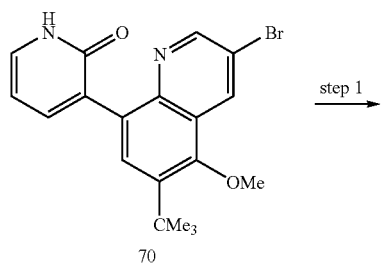

70 step 1 →

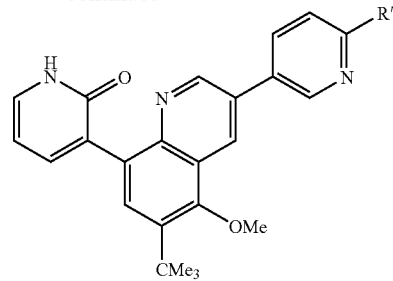

step 2
I-43: R' = NH₂
I24: R' = NHMs step 1—A tube was charged with 70 (208 mg, 0.582 mmol), 2-amino-pyridin-5-yl boronic acid (227 mg, 0.84 mmol), Pd(PPh₃)₄ (61 mg, 0.052 mmol), Na₂CO₃ (286 mg, 2.69 mmol), MeOH (1.6 mL) and DCM (0.5 mL), sealed and irradiated in a microwave reactor at 115° C. for 1 h. The reaction mixture was cooled to RT and diluted with EtOAc. The organic layer was washed with satd. aq. NaHCO₃ (30 mL). The organic phase was separated and the aqueous phase re-extracted with EtOAc (3×30 mL). The combined organic extracts were dried (MgSO₄), filtered and concentrated. The crude residue was purified by SiO₂ chromatography eluting with a DCM/MeOH gradient to afford 173 mg (71%) of I-43 as a white solid.

5-{5-[6-tert-butyl-5-methoxy-8-(2-oxo-1,2-dihydro-pyridin-3-yl)-quinolin-3-yl]-pyridin2-yl}methansulfonamide (124) can be prepared be sulfonylation of I-43 with methansulfonyl chloride according to the procedure in step 2 of example 5.

Example 29

N-{4-[6-tert-Butyl-5-methoxy-8-(6-methyl-2-oxo-1,2-dihydro-pyridin-3-yl)-quinolin-3-yl]-butyl}-methanesulfonamide (I-44)

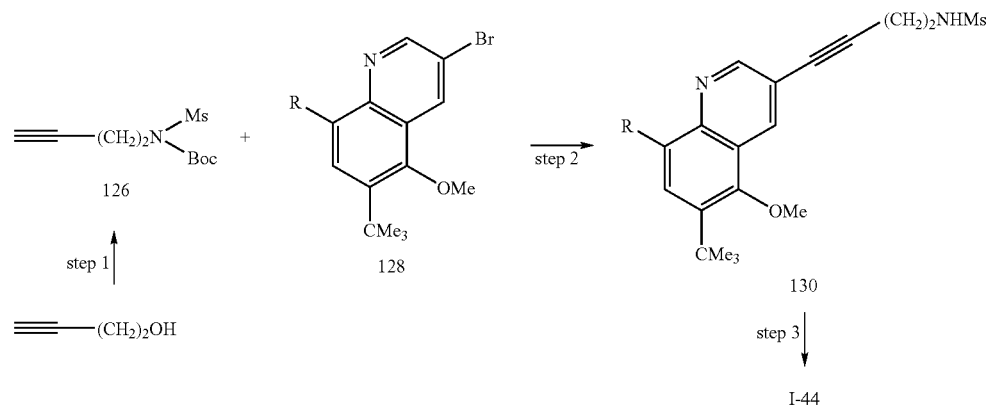

R = 6-methyl-2-oxo-1,2-dihydro-pyridin-3-yl 3-(3-Bromo-6-tert-butyl-5-methoxy-quinolin-8-yl)-6-methyl-1H-pyridin-2-one (128) can be prepared as in accord with the procedures used in steps 1 to 4 of example 9 to prepare 70 except in step 3, 30 is replaced with 75.

step 1—A mixture of 1-butynol (0.5 g, 7.13 mmol), MsN-HBoc (2.09 g, CASRN 147741-16-4), PPh₃ (2.8 g) in THF (30 mL) was cooled in an ice bath and DEAD (1.86 g) was added. The mixture was stirred overnight then concentrated in vacuo. The residue was triturated with Et₂O and the solid was filtered. The filtrate was concentrated and the process repeated. The crude product was purified by SiO₂ chromatography eluting with an EtOAc/hexane gradient (0 to 10% EtOAc) to afford 1.0 g of 126.

step 2—A tube was charged with 128 (0.25 g, 0.62 mmol), 126 (0.3 g, 1.25 mmol), CuI (12 mg), Pd(PPh₃)₄ (0.072 mg), TEA (0.5 mL) and DMF, sealed and heated to 90° C. overnight. The tube was cooled and the reaction mixture diluted with EtOAc, washed sequentially with H₂O and brine, dried (Na₂SO₄), filtered and concentrated in vacuo. The crude product was purified by SiO₂ chromatography eluting with an EtOAc/hexane gradient (50 to 100% EtOAc). The residue was dissolved in DCM and TFA (1 mL) was added and the resulting solution was stirred at RT overnight. The solvents were evaporated and the residue purified by SiO₂ chromatography eluting with an EtOAc/hexane gradient (50 to 100% EtOAc), then rechromatographed eluting with a MeOH/EtOAc gradient (0 to 8% MeOH) to afford 80 mg of 130.

step 3—A Parr flask was charged with 130 (60 mg, 128 μmol), Pd/C (13.7 mg) and a mixture of EtOAc and MeOH and hydrogenated under 50 psi of hydrogen for 20 h. An additional aliquot of Pd/C (13 mg) was added and hydrogenation continued for 72 h. The reaction mixture was filtered through CELITE, washed with DCM and the filtrate was concentrated in vacuo. The crude product was purified by SiO₂ chromatography eluting with MeOH/EtOAc gradient (0 to 10% MeOH) to afford 30 mg of I-44.

N-{3-[6-tert-Butyl-5-methoxy-8-(6-methyl-2-oxo-1,2-dihydro-pyridin-3-yl)-quinolin-3-yl]-propyl}-methanesulfonamide was prepared analogously except in step 2 the palladium catalyzed amination was carried out 3-propynyl methansulfonamide in place of 126.

N-{(E)-4-[6-tert-Butyl-5-methoxy-8-(6-methyl-2-oxo-1,2-dihydro-pyridin-3-yl)-quinolin-3-yl]-but-3-enyl}-methanesulfonamide was prepared analogously except in step 1 butynol was replaced with but-3-en-1-ol and hydrogenation (step 3) was omitted.

Example 30

N-{3-[6-tert-Butyl-5-methoxy-8-(6-methyl-2-oxo-1,2-dihydro-pyridin-3-yl)-quinolin-3-yloxy]-propyl}-methanesulfonamide (I-45)

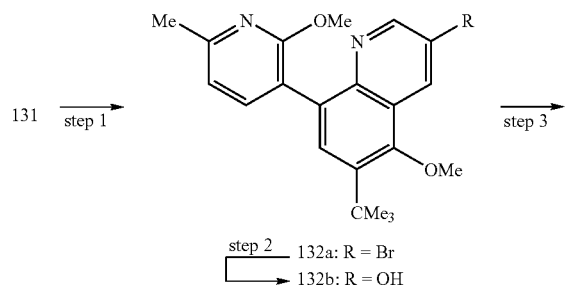

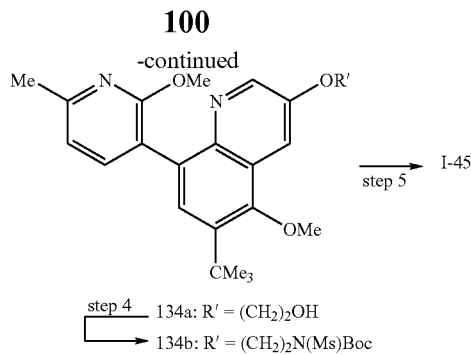

3-(6-Bromo-3-tert-butyl-4-methoxy-naphthalen-1-yl)-6-ethyl-1H-pyridin-2-one (131) was prepared in accord with steps 1 to 4 of example 8 except in step 3, 75 was used in place of 80.

step 1—A solution of 70 was dissolved in DMF and trimethyloxonium tetrafluoroborate was stirred at RT for 3 d. The resulting solution was washed sequentially with H₂O and brine, dried (Na₂SO₄), filtered and evaporated in vacuo. The crude product was purified by SiO₂ chromatography eluting with an EtOAc/hexane gradient (0 to 5% EtOAc) to afford 132a.

step 2—A round-bottomed flask was charged with 132a (0.1 g, 241 μmol), KOH (135 mg, 2.41 mmol), 2-di-tent-butylphosphino-3,4,5,6-tetramethyl-2',4',6' tri-isopropyl-1,1' biphenyl (23.2 mg, 48.2 μmol), dioxane and water to give a colorless suspension. The mixture was sparged with nitrogen for 30 min and Pd₂(dba)₃ was added and sparging with N₂ continued for another 10 min. The reaction vessel was capped and heated at 100° C. for 20 h. The reaction mixture was poured into EtOAc (50 mL) and washed sequentially with H₂O (20 mL) and brine (20 mL). The organic extracts were dried (Na₂SO₄), filtered and concentrated. The crude material was purified by SiO₂ chromatography eluting with an EtOAc/hexane (30 to 60% EtOAc) to afford 70 mg (82.5%) of 132b.

step 3—A flask was charged with 132b (120 mg, 340 μmol), 2-bromoethanol (213 mg, 1.7 mmol), K₂CO₃ (94.1 mg, 681 μmol) and MeCN (5 mL) to afford a colorless solution. The reaction mixture was heated to 70° C. and stirred for 20 h. The reaction mixture was poured into EtOAc (50 mL) and washed with H₂O (20 mL). The EtOAc layer was washed with brine, dried (Na₂SO₄), filtered and concentrated in vacuo. The crude material was purified by SiO₂ chromatography eluting with an EtOAc/hexane gradient to afford 100 mg (74.1%) of 134a.

step 4—A flask was charged with 134a (100 mg, 252 μmol), tert-butyl methylsulfonylcarbamate (73.9 mg, 378 μmol), PPh₃ (99.2 mg, 378 μmol) and THF (5 ml) and the solution was cooled in ice-bath. To the solution was added DEAD and reaction mixture was stirred RT for 20 h. The crude reaction mixture was concentrated in vacuo. The crude material was purified by SiO₂ chromatography eluting with an EtOAc/hexane gradient (20 to 60% EtOAc). The upper spot was (120 mg) was a 1:1 mixture of the product 134b and starting material BocNHMs (non UV, hard to separate from each other) and 40 mg of 134a was recovered.

step 5—A round-bottom flask was charged with 134b (60 mg, 105 μmol) from the previous step, HBr (74.5 mg, 921 μmol) and HOAc (0.5 mL). The mixture was heated at 60° C. for 3 h. The solution was cooled, diluted with H₂O (5 mL) and 4N NaOH (1 mL). The resulting solution was extracted with EtOAc (50 mL). The organic layer was washed sequentially with H₂O and brine, dried (Na₂SO₄), filtered and concentrated in vacuo. The crude material was purified by SiO₂ chromatography eluting with an EtOAc/hexane gradient (50% to 100% EtOAc) followed by a SiO₂ chromatography eluting with 10% MeOH/EtOAc to afford 30 mg (62.4%) of I-45.

Example 32

N—{(S)-1-[6-tert-Butyl-5-methoxy-8-(6-methoxymethyl-2-oxo-1,2-dihydro-pyridin-3-yl)-quinolin-3-yl]-pyrrolidin-3-ylmethyl}-methanesulfonamide (I-59)

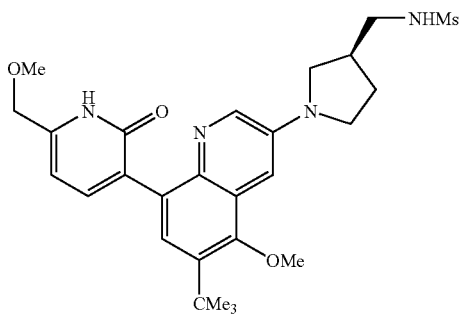

step 1—A NaH dispersion (226 mg, 5.64 mmol, 60% mineral oil dispersion) was triturated with hexanes (3×10 mL) and dried under a stream of N₂ then suspended in THF (23.5 mL) and cooled to 0° C. A solution of 3-bromo-2-methoxy-6-(hydroxymethyl)pyridine (0.88 g, 3.79 mmol) in THF (10 mL) was added drop-wise and the mixture was stirred for 30 min. To the solution was added MeI (1.00 g, 441 µl, 7.05 mmol) and the mixture was warmed to RT. After 1 h the crude reaction mixture was concentrated in vacuo and the mixture was poured into H₂O (100 mL) and extracted with EtOAc (3×50 mL). The combined extracts were washed sequentially with H₂O, brine, dried, filtered and concentrated to afford 3-bromo-2-methoxy-6-methoxymethyl-pyridine (136) as a light yellow oil.

step 2—A round-bottomed flask was charged with 136 (0.88 g, 3.79 mmol), PdCl₂(dppf).CH₂Cl₂ (155 mg, 190 µmol), bis-(pinacolato)diboron (1.16 g, 4.55 mmol), KOAc (1.12 g, 11.4 mmol) and DMF. The light yellow solution was heated to 100° C. and stirred for 1 h. The reaction mixture was cooled, poured onto 50 mL H₂O and extracted with EtOAc/toluene (1:1, 3×50 mL). The organic combined extracts were combined, washed sequentially with H₂O (50 mL) and brine (50 mL). The extracts were dried (Na₂SO₄), filtered and concentrated in vacuo afford and 2-methoxy-6-(methoxymethyl)-3-(4,4,5,5-tetramethyl-1,3,2-dioxaborolan-2-yl)pyridine (138) which was used without further purification.

step 3—A 10 mL screw-capped tube was charged 118 (0.103 g, 219 µmol), PdCl₂(dppf).CH₂Cl₂ (8.94 mg, 10.9 µmol), Cs₂CO₃ (214 mg, 657 µmol), 138 (183 mg, 263 µmol), dioxane (1.75 mL) and H₂O (438 µL), sealed and heated to 100° C. for 30 min. The reaction mixture was cooled, poured into H₂O (50 mL) and extracted with EtOAc (3×50 mL). The combined extracts were washed sequentially with H₂O (50 mL) and brine (50 mL). The organic layers were dried (Na₂SO₄), filtered and concentrated in vacuo. The crude material was purified by SiO₂ chromatography eluting with an EtOAc/hexane gradient (10 to 100% EtOAc) to afford 0.073 (61%) of (S)-N-((1-(6-tert-butyl-5-methoxy-8-(2-methoxy-6-(methoxymethyl)pyridin-3-yl)quinolin-3-yl)pyrrolidin-3-yl)methyl)methanesulfonamide (138) as a yellow foam.

step 4—Demethylation of 138 to afford I-32 was carried out in accord with the procedure in step 7 of example 2.

Example 33

N-{4-[6-tert-Butyl-8-(5-fluoro-6-methoxy-2-oxo-1,2-dihydro-pyridin-3-yl)-5-methoxy-quinolin-3-yl]-phenyl}-methanesulfonamide (I-47)

step 1—To a flask containing 2,3,6-trifluoropyridine (2 g, 15 mmol) was added MeOH (5 mL) followed by methanolic NaOMe (5 mL, 25% NaOMe in MeOH). An exothermic reaction occurred and some solid formed. The reaction was stirred for 10 min and diluted with H₂O. The solid was filtered and washed with H₂O. The solid was dissolved in EtOAc, washed sequentially with water and brine, dried (Na₂SO₄), filtered and concentrated in vacuo to afford 1.5 g (69%) of 3,6-difluoro-2-methoxy-pyridine (140). The recovered material was used without further purification.

step 2—To a solution of benzyl alcohol (1.12 g, 10.3 mmol) in THF was added NaH (0.413 g, 10.3 mmol, 60% mineral oil dispersion) and stirred for 30 min. To this solution was added 140 (1.5 g, 10.3 mmol) and the resulting solution was irradiated in the microwave synthesizer at 100° C. for 1 h. The reaction was cooled, diluted with H₂O, extracted with EtOAc (2×50 mL). The combined extracts were washed with brine, dried (Na₂SO₄), filtered and concentrated. The crude product was purified by SiO₂ chromatography to afford 1 g (41%) of 6-benzyloxy-3-fluoro-2-methoxy-pyridine (142).

step 3—A solution 142 (1 g, 4.29 mmol) in DMF (10 mL) was cooled in ice-bath and NBS (0.763 g, 4.29 mmol) was added. The colorless mixture was stirred for 2 h and then quenched with H₂O. The mixture was extracted with EtOAc (2×50 mL). The combined extracts were washed sequentially with H₂O and brine, dried (Na₂SO₄), filtered and concentrated in vacuo. The crude product was purified by SiO₂ chromatography to afford 0.5 g of 6-benzyloxy-5-bromo-3-fluoro-2-methoxy-pyridine (144).

step 3—N-{4-[6-tert-Butyl-5-methoxy-8-(4,4,5,5-tetramethyl-[1,3,2]dioxaborolan-2-yl)-quinolin-3-yl]-phenyl}-methanesulfonamide (146) can be prepared by condensation of 74b and bis-(pinacolato)diboron in accord with the procedure described in step b of example 16.

step 4—A microwave vial was charged with 146 (1 equiv.), 144 (1 equiv.), Pd(PPh₃)₄ (0.1 equiv.), Na₂CO₃ (3 equiv.), MeOH (9 mL) and DCM (3 mL), sealed and irradiated in a microwave synthesizer at 115° C. for 15 min. The reaction mixture was diluted with EtOAc, washed sequentially with H₂O and brine. The extracts were dried (Na₂SO₄), filtered and concentrated in vacuo. The crude product was purified by SiO₂ chromatography eluting with an EtOAc/hexane gradient (0 to 20% EtOAc) to afford 0.100 g of N-(4-(8-(2-(benzyloxy)-5-fluoro-6-methoxypyridin-3-yl)-6-tert-butyl-5-methoxyquinolin-3-yl)phenyl)methanesulfonamide (148).

step 5—A mixture of 148 (0.100 g, 0.162 mmol), Pd/C (30 mg) and EtOAc was stirred under one atmosphere hydrogen for 20 h. The catalyst was filtered and washed with EtOAc. The filtrate was concentrated and the crude product purified

Example 34

N-{4-[3-tert-Butyl-1-(6-methyl-2-oxo-1,2-dihydropyridin-3-yl)-isoquinolin-6-yl]-phenyl}-methanesulfonamide (I-48)

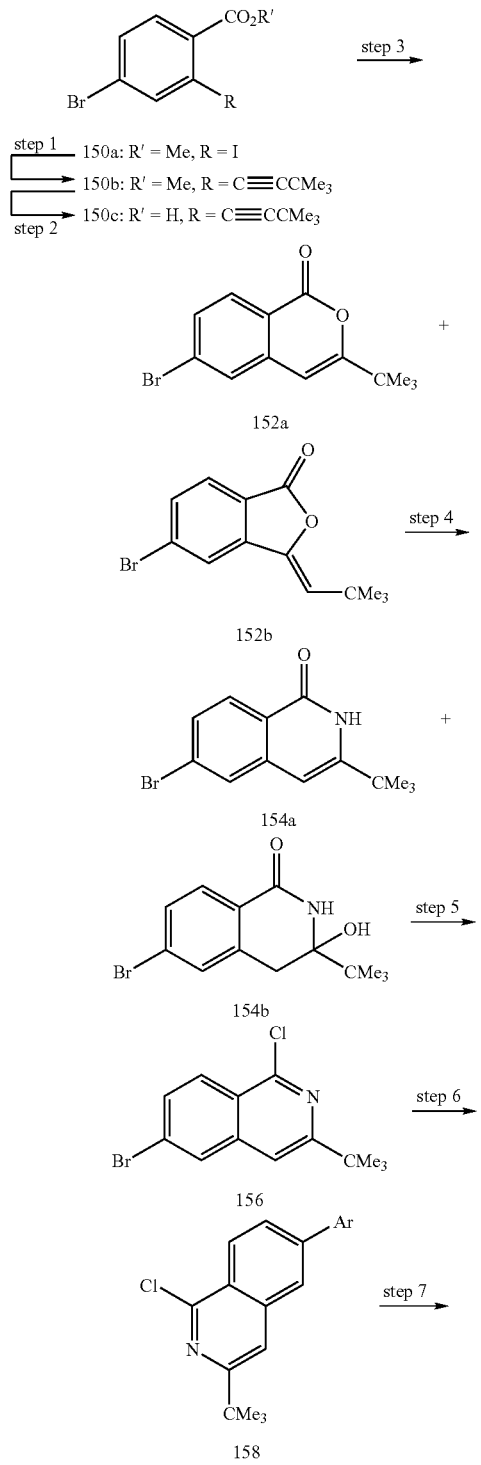

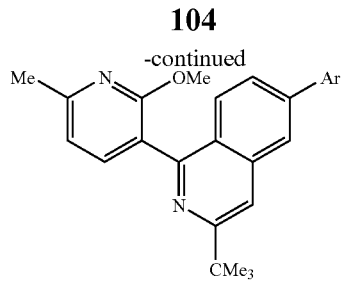

step 1—To a solution 150a (5.93 g, 17.4 mmol), Pd(PPh$_3$)$_2$Cl$_2$ (610 mg, 870 mmol), CuI (0.331 g, 1.74 mmol) and THF (178 mL) was added TEA (14.1 g, 19.4 mL, 139 mmol). The reaction mixture was degassed with Ar and then 3,3-dimethylbut-1-yne was added to the mixture. The mixture was stirred at RT overnight then diluted with ether and washed with H$_2$O. The organic extract was washed with 2N HCl and sat. AQ. NaHCO$_3$, dried (Na$_2$SO$_4$), filtered and concentrated. The crude material was purified by SiO$_2$ chromatography eluting with an EtOAc/hexane (0 to 10% EtOAc) to afford 150b. NMR indicated the product contained 10% of starting material.

step 2—Hydrolysis of 150b with methanolic NaOH under standard conditions afforded 150c.

step 3—A solution of 150c (4.58 g, 16.3 mmol), PdCl$_2$(MeCN)$_2$ (1.63 mmol), TEA (5.88 g, 8.1 mL, 58.1 mmol) and THF (320 mL) was stirred at RT overnight. The reaction mixture was diluted with Et$_2$O and washed sequentially with 10% HCl, H$_2$O and sat. NaHCO$_3$. The organic extract was dried (Na$_2$SO$_4$), filtered and concentrated in vacuo. The crude product was purified by SiO$_2$ chromatography eluting with a DCM/hexane gradient to afford 2.47 g (53.9%) of 152a and a second fraction which was a mixture of 152a and 152b.

step 4—A flask was charged with EtOH and saturated with ammonia. To the solution was added 152a (2.47 g, 8.79 mmol) and the solution irradiated in a microwave synthesizer at 130° C. for 5 h. The reaction was cooled to RT and a white solid precipitated which was filtered and dried to afford 1.849 g of 154a. The filtrate was concentrated to afford 0.562 g of a 1:1 mixture of 154a and 154b.

step 5—A mixture of 154a (0.5 g, 1.78 mmol) and POCl$_3$ (5 mL) was heated at 120° C. for 10 min. After cooling to RT the mixture was neutralized with satd. aq. NaHCO$_3$. The reaction mixture was extracted with EtOAc and the combined extracts were washed with satd. aq. NaHCO$_3$, dried (Na$_2$SO$_4$), filtered and concentrated in vacuo. The crude material was dry-loaded on a SiO$_2$ column and eluted with an EtOAc/hexane gradient (0 to 5% EtOAc) to afford 0.5 g (93.8%) of 156.

step 6—A vial was charged with 156 (0.5 g 1.67 mmol) and 25 (0.395 g, 1.84 mmol), Na$_2$CO$_3$ (532 mg, 5.02 mmol), Pd(PPh$_3$)$_4$ (0.193 g, 0.167 μmol) dioxane (3 mL) and H$_2$O (1 mL). The reaction mixture was heated to 80° C. and stirred for overnight. The reaction mixture was filtered through glass fiber paper and the filtrate partitioned between H$_2$O and EtOAc. The organic layer was washed with brine and dried (Na$_2$SO$_4$), filtered and concentrated in vacuo. The crude product was purified by SiO$_2$ chromatography eluting with an EtOAc/hexane gradient (0 to 50% EtOAc) to afford 0.38 g (58.4%) of 158 (Ar=4-methanesulfonylamino-phenyl)

step 7—A vial was charged with 158 (0.38 g, 977 μmol), 75 (326 mg, 1.95 mmol), Na$_2$CO$_3$ (311 mg, 2.93 mmol), Pd(PPh$_3$)$_4$ (0.113 g, 97.7 μmol) and DME. The reaction mixture was heated to 80° C. and stirred overnight. After 18 h, some 158 was still present. The reaction mixture was filtered through glass fiber paper and the filtrate was concentrated in vacuo. The crude material was purified by SiO$_2$ chromatography eluting with an EtOAc/hexane gradient (0 to 50% EtOAc) to afford 0.120 g (25.8%) of 160.

step 8—Demethylation of 160 (0.12 g) was carried out in accord with the procedure described in step 7 of example 2 to afford 0.10 g (85.9%) of I-48. The product precipitated and was purified by washing with H$_2$O and Et$_2$O.

Example 35

N-{4-[6-tert-Butyl-5-methoxy-8-(2-oxo-1,2-dihydropyridin-3-yl)-cinnolin-3-yl]-phenyl}-methanesulfonamide (161)

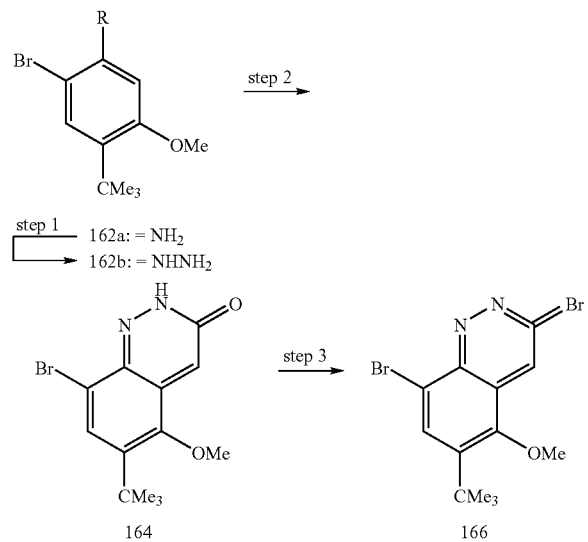

step 1—Using the literature procedure (*J. Organomet. Chem.* 2009 694:2493) 162a (1 equiv) is combined with NaNO$_2$ (3 equiv) and HCl in H$_2$O at 0° C. The reaction is allowed to warm to RT and stirred for 1 h. The reaction is recooled to 0° C. and SnCl$_2$ (5 equiv) is added. The reaction is warmed to RT overnight. The reaction is diluted with DCM and washed with 2 N KOH to remove tin salts. The organic layer is dried and concentrated in vacuo. The residue is further purified by passage through a short plug of SiO$_2$ to afford 162b.

step 2—A solution of 162b (1 equiv), diethoxyacetyl chloride (1 equiv, prepared from diethoxyacetic acid and SOCl$_2$), and TEA (2 equiv) in DCM is maintained at RT overnight. The reaction is washed with satd. aq. NH$_4$Cl, dried and concentrated in vacuo. The resulting residue is dissolved in conc. H$_2$SO$_4$ at 0° C. and then the reaction is warmed to RT and stirred for 20 h. The reaction is neutralized with satd. aq. NaHCO$_3$ and extracted with DCM. The organic layer is dried and concentrated in vacuo and the residue is purified by SiO$_2$ chromatography to afford 164.

step 3—Using the procedure described in step 3 of example 36, a solution 164 (1 equiv) and POBr$_3$ (3 equiv) in DMF affords dibromocinnoline 166.

The conversion of 166 to 161 is accomplished by sequential palladium-catalyzed coupling with 25 and 30.

Example 36

N-{4-[6-tert-Butyl-5-methoxy-8-(2-oxo-1,2-dihydropyridin-3-yl)-isoquinolin-3-yl]-phenyl}-methanesulfonamide (174)

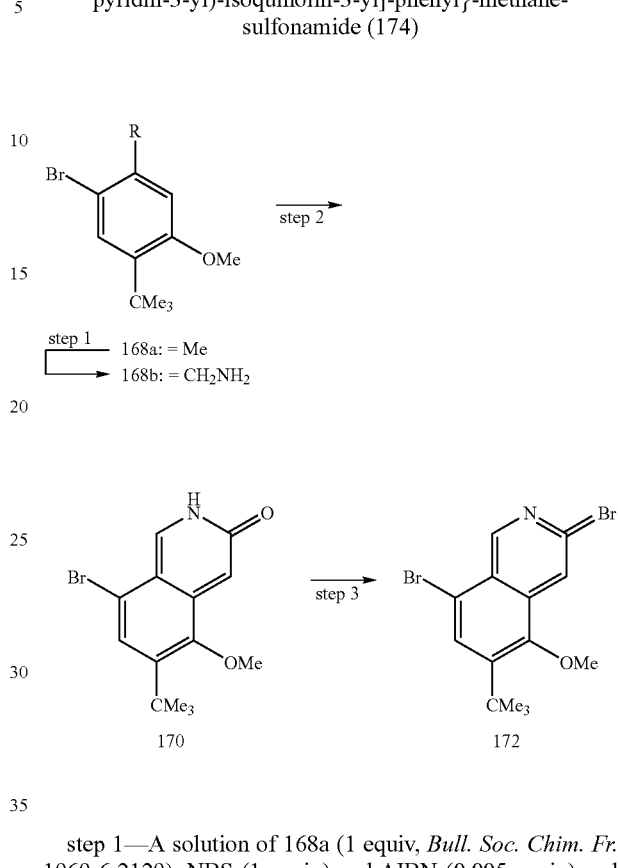

step 1—A solution of 168a (1 equiv, *Bull. Soc. Chim. Fr.* 1969 6:2129), NBS (1 equiv) and AIBN (0.005 equiv) and benzene is heated at reflux for 14 h. The reaction is cooled to RT and the solid precipitate is removed by filtration. The benzene is removed in vacuo and the resulting residue is dissolved in NH$_3$/MeOH (4 M) and stirred at RT overnight. The solvents are removed in vacuo and the residue is purified by SiO$_2$ chromatography to afford 168b.

step 2—A solution of 168b (1 equiv), diethoxyacetyl chloride (1 equiv, prepared from diethoxyacetic acid and SOCl$_2$), and Et$_3$N (2 equiv) in DCM is stirred at RT for 3 h. The reaction is washed with satd. aq. NH$_4$Cl, dried and concentrated in vacuo. The resulting residue is dissolved in conc. H$_2$SO$_4$ at 0° C. and then the reaction is allowed to warm to RT and is maintained for 28 h. The reaction is neutralized with satd. aq. NaHCO$_3$ and extracted with DCM. The organic layer is dried and concentrated in vacuo and the residue is purified by SiO$_2$ chromatography to afford 170.

step 3—Using the literature procedure (*Chem. Lett.* 2007 36(8):1036) a solution of 170 (1 equiv) and POBr$_3$ (3 equiv) in DMF is maintained at 90° C. for 2 h. The solution is cooled to RT, made basic with 1 N KOH solution, extracted with DCM. The combined extracts are washed with H$_2$O, dried, filtered and concentrated in vacuo. The residue is purified with SiO$_2$ chromatography to afford 172.

The conversion of 172 to 174 is accomplished by sequential palladium-catalyzed coupling with 25 and 30.

Example 38

N-{4-[6-tert-Butyl-8-(6-hydroxymethyl-2-oxo-1,2-dihydro-pyridin-3-yl)-5-methoxy-quinolin-3-yl]-phenyl}-methanesulfonamide (I-41)

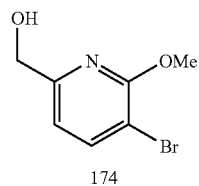

174

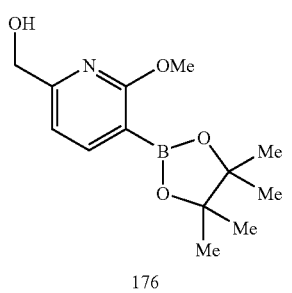

176

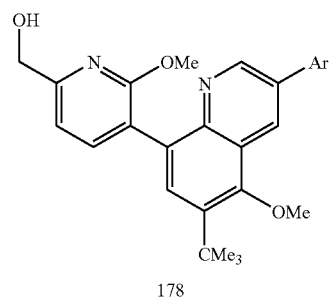

178

Ar = 4-methanesulfonylamino-phenyl step 1—6-Hydroxymethyl-2-methoxy-3-(4,4,5,5-tetramethyl-1,3,2-dixaborolan-2-yl)pyridine (176, CASRN 1206776-83-1) was prepared from 174 in accord with the procedure example 26 except 174 was used in place of 2,4-dimethoxy-5-bromo-pyrimidine.

step 2—A vial was charged with 74b (0.125 g, 0.27 mmol) 176 (71 mg, 0.27 mmol), PdCl$_2$(dppf.).CH$_2$Cl$_2$ (0.011 g, 0.05 mmol), Cs$_2$CO$_3$ (0.269 g, 0.809 mmol), dioxane (2 mL) and H$_2$O (0.5 mL), degassed, sealed and heated at 100° C. for 1 h. The product was cooled, partitioned between EtOAc and H$_2$O. The organic extract was washed with brine, dried (MgSO$_4$), filtered and concentrated in vacuo to afford 178 which was used without further purification.

step 3—Demethylation of 178 was carried out in accord with the procedure in step 7 of example 2. The crude product was purified on a preparative TLC plate developed with 10% MeOH/DCM to afford 3 mg of I-41.

Example 39

N—{(S)-1-[6-tert-Butyl-8-(6-methoxy-2-oxo-1,2-dihydro-pyridin-3-yl)-quinolin-3-yl]-pyrrolidin-3-ylmethyl}-methanesulfonamide (I-60)

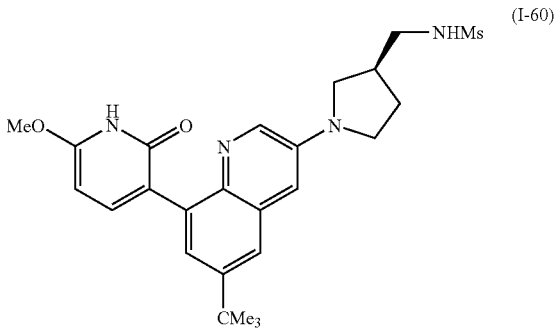

6-tent-butyl-3,8-dibromoquinoline (180) is prepared from 2-bromo-4-tert-butyl naphthalene using acrolein and bromine in accord with the procedure in step 2 of example 7. Introduction of 1-pyrrolidin-3-ylmethyl methansulfonamide moiety can be carried out with (S)-1-pyrrolidin-3-ylmethyl-carbamic acid tent-butyl ester in accord with the procedures in steps 1 to 3 of example 19. Introduction of the pyridine ring is carried out by a Suzuki condensation of the bromoquinoline intermediate with 115 in accord with the procedure in step 2 of example 24 and subsequent demethylation of the methyl pyridinyl ether in accord with the procedure in step 6 of example 22 to afford I-60.

Example 40

N-{4-[6-tert-Butyl-8-(dioxo-tetrahydro-pyrimidin-1-yl)-quinolin-3-yl]-phenyl}-methanesulfonamide (I-61)

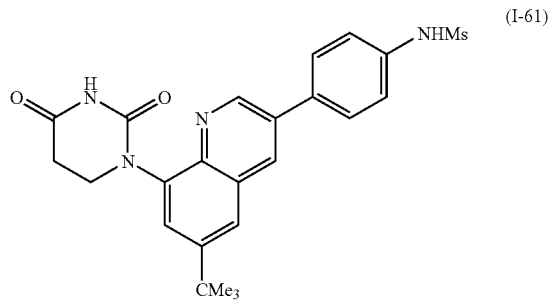

The title compound is prepared from 180 by introduction of the methansulfonylaminophenyl moiety utilizing a Suzuki coupling I accord with the procedure in step 2 of example 13. Elaboration of the dioxo-tetrahydro-pyrimidin-1-yl substituent is carried out in accord with the procedures steps 1 to 3 of example 17 to afford I-61.

Example 41

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570-Con1 at the end of the reaction was directly proportional to the amount of light emitted by the scintillant.

The N-terminal 6-histidine tagged HCV polymerase, derived from HCV Con1 strain, genotype 1b (NS5B570n-Con1) contains a 21 amino acid deletion at the C-terminus relative to the full-length HCV polymerase and was purified from E. coli strain BL21(DE) pLysS. The construct, containing the coding sequence of HCV NS5B Con1 (GenBank accession number AJ242654) was inserted into the plasmid construct pET17b, downstream of a T7 promoter expression cassette and transformed into E. coli. A single colony was grown overnight as a starter culture and later used inoculate 10 L of LB media supplemented with 100 µg/mL ampicillin at 37° C. Protein expression was induced by the addition of 0.25 mM isopropyl-β-D-thiogalactopyranoside (IPTG) when optical density at 600 nM of the culture was between 0.6 and 0.8 and cells were harvested after 16 to 18 h at 30° C. NS5B570n-Con1 was purified to homogeneity using a three-step protocol including subsequent column chromatography on Ni-NTA, SP-Sepharose HP and Superdex 75 resins.

Each 50 µL enzymatic reaction contained 20 nM RNA template derived from the complementary sequence of the Internal Ribosome Entry Site (cIRES), 20 nM NS5B570n-Con1 enzyme, 0.5 µCi of tritiated UTP (Perkin Elmer catalog no. TRK-412; specific activity: 30 to 60 Ci/mmol; stock solution concentration from $7.5 \times 10^{-5}$ M to $20.6 \times 10^{-6}$ M), 1 µM each ATP, CTP, and GTP, 40 mM Tris-HCl pH 8.0, 40 mM NaCl, 4 mM DTT (dithiothreitol), 4 mM $MgCl_2$, and 5 µl of compound serial diluted in DMSO. Reaction mixtures were assembled in 96-well filter plates (cat #MADVN0B, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 µl of scintillant (Microscint 20, Perkin-Elmer) was added to each reaction well.

The amount of light emitted from the scintillant was converted to counts per minute (CPM) on a Topcount® plate reader (Perkin-Elmer, Energy Range: Low, Efficiency Mode Normal, Count Time: 1 min, Background Subtract: none, Cross talk reduction: Off).

Data was analyzed in Excel® (Microsoft) and Activity-Base® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50% ($IC_{50}$) was calculated by fitting equation (i) to the data where "Y"

$$Y = \% \text{ Min} + \frac{(\% \text{ Max} - \% \text{ Min})}{\left[1 + \frac{x}{(IC_{50})^S}\right]} \quad (i)$$

corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

Example 42

HCV Replicon Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The Renilla luciferase gene was introduced into the first open reading frame of a genotype 1b replicon construct NK5.1 (N. Krieger et al., J. Virol. 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, EMBO 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of Renilla luciferase expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express Renilla luciferase reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using the R. luciferase Assay system (Promega cat no. E2820). All the reagents described in the following paragraph were included in the manufacturer's kit, and the manufacturer's instructions were followed for preparations of the reagents. The cells were washed once with 100 µl of phosphate buffered saline (pH 7.0) (PBS) per well and lysed with 20 µL of 133 R. luciferase Assay lysis buffer prior to incubation at room temperature for 20 min. The plate was then inserted into the Centro LB 960 microplate luminometer (Berthold Technologies), and 100 µL of R. luciferase Assay buffer was injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) was used for the cytotoxicity assay. Ten microliter of WST-1 reagent was added to each well of the transparent plates including wells that contain media alone as blanks Cells were then incubated for 2 h at 37° C., and the OD value was measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

TABLE III

| Compound Number | HCV Replicon Activity $IC_{50}$ (μM) | Cytotoxic Activity $CC_{50}$ (μM) |
|---|---|---|
| I-18 | 0.0052 | 30.3 |
| I-21 | 0.0003 | — |
| I-48 | 0.0274 | — |
| I-60 | 0.0818 | — |

Example 43

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula (I) wherein:

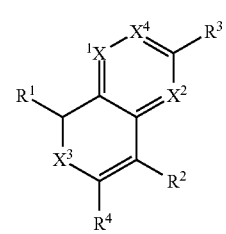

$X^1$ is N and $X^2$, $X^3$ and $X^4$ are $CR^5$;

$R^1$ is (a) a heteroaryl radical selected from the group consisting of pyridinyl, 2-oxo-1,2-dihydro-pyridin-3-yl, 3-oxo-3,4-dihydro-pyrazin-2-yl, 3-oxo-2,3-dihydro-pyridazin-4-yl, 2-oxo-1,2-dihydro-pyrimidin-4-one-5-yl, 6-oxo-1,6-dihydro-[1,2,4]triazin-5-yl, 2-oxo-2(H)-pyridin-1-yl, 6-oxo-6H-pyridazin-1-yl, 6-oxo-6H-pyrimidin-1-yl and 2-oxo-2H-pyrazin-1-yl said heteroaryl being optionally substituted by halogen, $C_{1-6}$ alkyl, $C_{1-3}$ haloalkyl, $C_{1-6}$ hydroxyalkyl, $C_{1-3}$ alkoxy-$C_{1-3}$ alkyl $C_{1-6}$ alkoxy, $X^6$—$(CH_2)_{1-6}CO_2H$ or $X^6$—$(CH_2)_{2-6}NR^gR^h$ wherein $X^6$ is O or $NR^g$; or, (b) a heterocyclic radical selected from the group consisting of 2-oxo-tetrahydro-pyrimidin-1-yl, 2-oxo-imidazolidin-1-yl, 2-oxo-piperidin-1-yl, 2-oxo-pyrrolidin-1-yl, 2,4-dioxo-1,2,3,4-tetrahydro-pyrimidin-5-yl, 2,5-dioxo-imidazolidin-1-yl and 2,4-dioxo-tetrahydro-pyrimidin-1-yl;

$R^2$ is hydrogen, $C_{1-6}$ alkoxy, $C_{1-6}$ alkyl, $C_{1-6}$ haloalkyl, $C_{1-6}$ haloalkoxy or halogen;

$R^3$ is (a) aryl, (b) heteroaryl, (c) $NR^aR^b$, (d) halogen wherein said aryl or said heteroaryl are optionally independently substituted with one to three substitutents selected from the group consisting of hydroxy, $C_{1-6}$ alkoxy, $C_{1-6}$ alkyl, $C_{1-6}$ hydroxyalkyl, halogen, $(CH_2)_n NR^cR^d$, cyano, $C_{1-6}$ alkoxycarbonyl, carbamoyl, N-alkylcarbamoyl, N,N-dialkylcarbamoyl, $(CH_2)_{0-3} CO_2H$, $SO_2NH_2$, $C_{1-6}$ alkylsulfinyl and $C_{1-6}$ alkylsulfonyl or (e) —X—$[C(R^6)_2]_{2-6}NR^eR^f$ wherein X is O or $NR^7$, $R^7$ is hydrogen or $C_{1-3}$ alkyl, $R^6$ is independently in each occurrence hydrogen, $C_{1-3}$ alkyl or two $R^6$ residues on the same carbon are $C_{2-5}$ alkylene or two $R^6$ residues on different carbons are $C_{1-4}$ alkylene;

$R^a$ and $R^b$ along with the nitrogen to which they are attached are a cyclic amine independently substituted by one to three groups independently selected from $C_{1-6}$ alkyl, halogen or $(CH_2)_nNR^eR^f$;

$R^c$ and $R^d$ are independently hydrogen, $C_{1-6}$ alkyl, $C_{1-6}$ haloalkyl, $C_{1-6}$ acyl, $SO_2R^8$ wherein $R^8$ is (a) $C_{1-6}$ alkyl, (b) $C_{1-6}$ haloalkyl, (c) $C_{3-7}$ cycloalkyl, (d) $C_{3-7}$ cycloalkyl-$C_{1-3}$ alkyl, (e) $C_{1-6}$ alkoxy-$C_{1-6}$ alkyl or (f) $SO_2[C(R^9)_2]_{0-6}NR^kR^l$, $C_{1-3}$ alkylcarbamoyl or $C_{1-3}$ dialkylcarbamoyl;

$R^e$ and $R^f$, are independently hydrogen, $C_{1-6}$ alkyl, $C_{1-6}$ haloalkyl, $C_{1-6}$ acyl, $SO_2R^8$ wherein $R^8$ is (a) $C_{1-6}$ alkyl, (b) $C_{1-6}$ haloalkyl, (c) $C_{3-7}$ cycloalkyl, (d) $C_{3-7}$ cycloalkyl-$C_{1-3}$ alkyl, (e) $C_{1-6}$ alkoxy-$C_{1-6}$ alkyl or (f) $SO_2[C(R^9)_2]_{0-6} NR^kR^l$;

$R^i$ and $R^j$ are (i) independently hydrogen, $C_{1-3}$ alkyl or $(CH_2)_{2-6}NR^gR^h$ or (ii) together with the nitrogen to which they are attached are $(CH_2)_2X^5(CH_2)_2$, wherein $X^5$ is O or $NR^k$ and $R^k$ is hydrogen, $C_{1-3}$ alkyl, $C_{1-3}$ acyl or $C_{1-3}$ alkylsulfonyl;

$R^4$ is hydrogen, $CF_3$, $CH_2CF_3$, $C_{3-5}$ cycloalkyl, halogen, $C_{1-6}$ alkoxy, $C_{1-3}$ haloalkoxy, $CHR^{4a}R^{4b}$ or $CR^{4a}R^{4b}R^{4c}$ wherein
(i) $R^{4a}$, $R^{4b}$ and $R^{4c}$ are independently selected from $C_{1-3}$ alkyl, $CD_3$, $C_{1-2}$ alkoxy, $C_{1-2}$ fluoroalkyl, $C_{1-3}$ hydroxyalkyl, cyano or hydroxy; or,
(ii) when taken together, $R^{4a}$ and $R^{4b}$ together are $C_{2-4}$ alkylene and $R^{4c}$ is hydrogen, $C_{1-3}$ alkyl, $C_{1-2}$ alkoxy, halogen, $C_{1-3}$ hydroxyalkyl, cyano or $C_{1-2}$ fluoroalkyl or $R^{4a}$ and $R^{4b}$ together with the carbon to which they are attached are 3-oxetanyl, or tetrahydrofuran-2-yl;

$R^5$ is independently in each occurrence hydrogen, halogen, $C_{1-6}$ alkoxy, or $C_{1-6}$ alkyl;

$R^8$, $R^g$ and $R^h$ are independently in each occurrence hydrogen or $C_{1-3}$ alkyl;

$R^k$ and $R^l$ are (i) independently in each occurrence hydrogen or $C_{1-6}$ alkyl or (ii) together with the nitrogen to which they are attached $R^k$ and $R^l$ form a cyclic amine;

n is independently in each occurrence zero, one, two or three; or, a pharmaceutically acceptable salt thereof.

2. A compound according to claim 1 wherein $X^1$ is N and $X^2$, $X^3$ and $X^4$ are $CR^5$, $R^1$ is 2,6-dioxo-tetrahydro-pyrimidin-1-yl, 2,5-dioxo-imidazolidin-1-yl or 2,4-dioxo-tetrahydro-pyrimidin-1-yl; and $R^3$ is (a) phenyl substituted at least by $(CH_2)_nNR^cR^d$ at the 4-position and wherein n is zero or (b) $NR^aR^b$.

3. A compound according to claim 1 wherein $R^3$ is (a) phenyl substituted at least by $(CH_2)_nNR^cR^d$ at the 4-position and wherein n is zero or (b) $NR^aR^b$.

4. A compound according to claim 3 wherein $R^3$ is phenyl substituted at least by $(CH_2)_nNR^cR^d$ at the 4-position and wherein n is zero and $R^1$ is 6-oxo-1,6-dihydro-[1,2,4]triazin-5-yl.

5. A compound according to claim 3 wherein $R^3$ is phenyl substituted at least by $(CH_2)_nNR^cR^d$ at the 4-position and wherein n is zero and $R^1$ is 2-oxo-tetrahydro-pyrimidin-1-yl.

6. A compound according to claim 3 wherein $R^1$ is 2-oxo-1,2-dihydro-pyridin-3-yl optionally substituted by halogen, $C_{1-6}$ alkyl, $C_{1-3}$ haloalkyl or $C_{1-6}$ alkoxy and $R^3$ is phenyl substituted at least by $(CH_2)_nNR^cR^d$ at the 4-position wherein n is zero or one.

7. A compound according to claim 6 wherein $R^4$ is trifluoromethyl or $CR^{4a}R^{4b}R^{4c}$ and (a) $R^{4a}$, $R^{4b}$ and $R^{4c}$ are independently $CH_3$ or $CD_3$ or $R^{4a}$ and $R^{4b}$ together are $C_2$ alkylene and (b) $R^{4c}$ is $C_{1-3}$ alkyl, $C_{1-2}$ alkoxy, halogen, $C_{1-3}$ hydroxyalkyl, cyano or $C_{1-2}$ fluoroalkyl.

8. A compound according to claim 3 wherein $R^3$ is $NR^aR^b$ and $R^4$ is trifluoromethyl or $CR^{4a}R^{4b}R^c$ and (a) $R^{4a}$, $R^{4b}$ and $R^{4c}$ are independently $CH_3$ or $CD_3$ or $R^{4a}$ and $R^{4b}$ together are $C_2$ alkylene and (b) $R^{4c}$ is $C_{1-3}$ alkyl, $C_{1-2}$ alkoxy, halogen, $C_{1-3}$ hydroxyalkyl, cyano or $C_{1-2}$ fluoroalkyl.

9. A compound according to claim 5 wherein $NR^aR^b$ together is a cyclic amine substituted by $(CH_2)_nNR^eR^f$ wherein n is zero, one or two; and $R^e$ and $R^f$ are independently hydrogen, $C_{1-6}$ alkyl, $C_{1-6}$ haloalkyl, $SO_2R^8$ wherein $R^8$ is (a) $C_{1-6}$ alkyl, (b) $C_{1-6}$ haloalkyl, (c) $C_{3-7}$ cycloalkyl, (d) $C_{3-7}$ cycloalkyl-$C_{1-3}$ alkyl, (e) $C_{1-6}$ alkoxy-$C_{1-6}$ alkyl.

10. A compound according to claim 1 selected from the list consisting of:
N-{4-[6-tert-butyl-2-methoxy-8-(2-oxo-1,2-dihydro-pyridin-3-yl)-quinolin-3-yl]-phenyl}-methanesulfonamide;
N-{4-[6-tert-butyl-8-(5-fluoro-2-oxo-1,2-dihydro-pyridin-3-yl)-quinolin-3-yl]-phenyl}-methanesulfonamide;
N-{1-[6-tert-butyl-8-(5-fluoro-2-oxo-1,2-dihydro-pyridin-3-yl)-quinolin-3-yl]-piperidin-4-yl}-methanesulfonamide;
N-{-4-[6-tert-butyl-5-methoxy-8-(2-oxo-1,2-dihydro-pyridin-3-yl)-quinolin-3-yl]-phenyl}-methanesulfonamide;
N-{4-[6-tert-butyl-8-(5-chloro-2-oxo-1,2-dihydro-pyridin-3-yl)-5-methoxy-quinolin-3-yl]-phenyl}-methanesulfonamide;
3-(3-bromo-6-tert-butyl-5-methoxy-quinolin-8-yl)-1H-pyridin-2-one;
3 (6 tea butyl 5 methoxy quinolin-8-yl)-1H pyridin-2-one;
N-{(S)-1-[6-tert-butyl-5-methoxy-8-(2-oxo-1,2-dihydro-pyridin-3-yl)-quinolin-3-yl]-pyrrolidin-3-ylmethyl}-methanesulfonamide;
N-{1-[6-tert-butyl-5-methoxy-8-(2-oxo-1,2-dihydro-pyridin-3-yl)-quinolin-3-yl]-azetidin-3-ylmethyl}-methanesulfonamide;
N-{4-[6-tert-butyl-8-(2,4-dioxo-3,4-dihydro-2H-pyrimidin-1-yl)-5-methoxy-quinolin-3-yl]-phenyl}-methane sulfonamide;
N-{1-[6-tert-butyl-4-chloro-5-methoxy-8-(2-oxo-1,2-dihydro-pyridin-3-yl)-quinolin-3-yl]azetidin-3-ylmethyl}-methanesulfonamide;

N-{4-[6-tert-butyl-8-(5-fluoro-2-oxo-1,2-dihydro-pyridin-3-yl)-5-methoxy-quinolin-3-yl]-phenyl}-methanesulfonamide;

N-{4-[6-tert-butyl-5-methoxy-8-(6-methyl-2-oxo-1,2-dihydro-pyridin-3-yl)-quinolin-3-yl]-phenyl}-methanesulfonamide;

N-{4-[6-tert-butyl-8-(2,4-dioxo-1,2,3,4-tetrahydro-pyrimidin-5-yl)-5-methoxy-quinolin-3-yl]-phenyl}-methanesulfonamide;

N-{-4-[6-tert-butyl-8-(3-fluoro-pyridin-4-yl)-5-methoxy-quinolin-3-yl]-phenyl}-methanesulfonamide;

N-{4-[6-tert-butyl-5-methoxy-8-(2-oxo-tetrahydro-pyrimidin-1-yl)-quinolin-3-yl]-phenyl}-methanesulfonamide;

N-{4-[6-tert-butyl-8-(dioxo-tetrahydro-pyrimidin-1-yl)-5-methoxy-quinolin-3-yl]-phenyl}-methanesulfonamide;

N-{4-[8-(2,4-dioxo-tetrahydro-pyrimidin-1-yl)-5-methoxy-6-trifluoromethyl-quinolin-3-yl]-phenyl}-methanesulfonamide;

N—{(S)-1-[6-tert-butyl-8-(2,4-dioxo-3,4-dihydro-2H-pyrimidin-1-yl)-5-methoxy-quinolin-3-yl]-pyrrolidin-3-ylmethyl}-methanesulfonamide;

N-{4-[6-[1,1-di(methyl-$d_3$)ethyl-2,2,2-$d_3$]-5-methoxy-8-(2-oxo-1,2-dihydro-pyridin-3-yl)-quinolin-3-yl]-phenyl}-methanesulfonamide; and, N-{4-[8-(dioxo-tetrahydro-pyrimidin-1-yl)-5-methoxy-6-(2,2,2-trifluoro-ethyl)-quinolin-3-yl]-phenyl}-methanesulfonamide; or, a pharmaceutically acceptable salt thereof.

11. A compound according to claim 1 selected from the list consisting of:

N-{4-[6-tert-butyl-5-methoxy-8-(6-methoxy-2-oxo-1,2-dihydro-pyridin-3-yl)-quinolin-3-yl]-phenyl}-methanesulfonamide;

N-{-4-[6-tert-butyl-8-(6-methyl-2-oxo-1,2-dihydro-pyridin-3-yl)-quinolin-3-yl]-phenyl}-methanesulfonamide;

N-{4-[6-tert-butyl-8-(6-methyl-2-oxo-1,2-dihydro-pyridin-3-yl)-quinolin-3-yl]-phenyl}-methanesulfonamide;

2-[6-tert-butyl-5-methoxy-8-(2-oxo-1,2-dihydro-pyridin-3-yl)-quinolin-3-yl]-benzoic acid;

N-{4-[6-tert-butyl-5-methoxy-8-(2-oxo-1,2-dihydro-pyridin-3-yl)-quinolin-3-yl]-2-fluoro-phenyl}-methanesulfonamide;

N—{(S)-1-[6-tert-butyl-8-(6-methyl-2-oxo-1,2-dihydro-pyridin-3-yl)-quinolin-3-yl]-pyrrolidin-3-ylmethyl}-methanesulfonamide;

N-{-4-[6-tert-butyl-5-methoxy-8-(2-oxo-1,2-dihydro-pyridin-3-yl)-quinolin-3-yl]-morpholin-2-ylmethyl}-methanesulfonamide;

N-{1-[6-tert-butyl-8-(6-methyl-2-oxo-1,2-dihydro-pyridin-3-yl)-quinolin-3-yl]-piperidin-3-ylmethyl}-methanesulfonamide;

2-[6-tert-butyl-8-(6-methyl-2-oxo-1,2-dihydro-pyridin-3-yl)-quinolin-3-yl]-5-methanesulfonylamino-benzoic acid methyl ester;

2-[6-tert-butyl-8-(6-methyl-2-oxo-1,2-dihydro-pyridin-3-yl)-quinolin-3-yl]-5-methanesulfonylamino-benzoic acid;

N-{4-[6-tert-butyl-8-(6-methyl-2-oxo-1,2-dihydro-pyridin-3-yl)-quinolin-3-yl]-morpholin-2-ylmethyl}-methanesulfonamide;

N-{1-[6-tert-butyl-8-(6-methyl-2-oxo-1,2-dihydro-pyridin-3-yl)-quinolin-3-yl]-3-methyl-pyrrolidin-3-ylmethyl}-methanesulfonamide;

N-(3-{[6-tert-butyl-5-methoxy-8-(6-methyl-2-oxo-1,2-dihydro-pyridin-3-yl)-quinolin-3-yl]-methanesulfonylamino}-propyl)-methanesulfonamide;

prop-2-ene-1-sulfonic acid {4-[6-tert-butyl-5-methoxy-8-(6-methoxy-2-oxo-1,2-dihydro-pyridin-3-yl)-quinolin-3-yl]-phenyl}-amide;

2,3-dihydroxy-propane-1-sulfonic acid {4-[6-tert-butyl-5-methoxy-8-(6-methoxy-2-oxo-1,2-dihydro-pyridin-3-yl)-quinolin-3-yl]-phenyl}-amide;

N-{5-[6-tert-butyl-8-(6-methyl-2-oxo-1,2-dihydro-pyridin-3-yl)-quinolin-3-yl]-furan-2-ylmethyl}-methanesulfonamide;

N-{1-[6-tert-butyl-8-(6-methyl-2-oxo-1,2-dihydro-pyridin-3-yl)-quinolin-3-yl]-4,4-dimethyl-pyrrolidin-3-ylmethyl}-methanesulfonamide;

N-{1-[6-tert-butyl-5-methoxy-8-(6-methoxy-2-oxo-1,2-dihydro-pyridin-3-yl)-quinolin-3-yl]-3-methyl-pyrrolidin-3-ylmethyl}-methanesulfonamide;

N-{4-[6-tert-butyl-8-(6-hydroxymethyl-2-oxo-1,2-dihydro-pyridin-3-yl)-5-methoxy-quinolin-3-yl]-phenyl}-methanesulfonamide;

N-{4-[6-tert-butyl-8-(5-fluoro-2-methoxy-6-oxo-1,6-dihydro-pyridin-3-yl)-5-methoxy-quinolin-3-yl]-phenyl}-methanesulfonamide;

N—{(S)-1-[6-tert-butyl-5-methoxy-8-(6-methoxymethyl-2-oxo-1,2-dihydro-pyridin-3-yl)-quinolin-3-yl]-pyrrolidin-3-ylmethyl}-methanesulfonamide; and, N—{(S)-1-[6-tert-butyl-8-(6-hydroxymethyl-2-oxo-1,2-dihydro-pyridin-3-yl)-5-methoxy-quinolin-3-yl]-pyrrolidin-3-ylmethyl}-methanesulfonamide; or, a pharmaceutically acceptable salt thereof.

12. A compound wherein said compound is N-{4-[6-tert-butyl-5-methoxy-8-(3-methyl-5-oxo-1,5-dihydro-[1,2,4]triazol-4-yl)-quinolin-3-yl]-phenyl}-methanesulfonamide.

13. A composition comprising a compound according to claim 1 admixed with at least one pharmaceutically acceptable carrier, diluent or excipient.

* * * * *

UNITED STATES PATENT AND TRADEMARK OFFICE
CERTIFICATE OF CORRECTION

PATENT NO. : 8,026,253 B2  
APPLICATION NO. : 12/797308  
DATED : September 27, 2011  
INVENTOR(S) : Javier de Vicente Fidalgo et al.

It is certified that error appears in the above-identified patent and that said Letters Patent is hereby corrected as shown below:

Under Column 114, line 55, please delete "3 (6 tea butyl 5 methoxy quinolin-8-yl)-1H pyridin-2-one;".

Signed and Sealed this
Fifteenth Day of November, 2011

David J. Kappos
*Director of the United States Patent and Trademark Office*